(12) United States Patent
Garrels et al.

(10) Patent No.: US 12,281,468 B2
(45) Date of Patent: Apr. 22, 2025

(54) SANITIZATION SYSTEM

(71) Applicant: Kohler Co., Kohler, WI (US)

(72) Inventors: Clayton Garrels, Sheboygan, WI (US); William Kuru, Plymouth, WI (US)

(73) Assignee: Kobler Co., Kohler, WI (US)

(*) Notice: Subject to any disclaimer, the term of this patent is extended or adjusted under 35 U.S.C. 154(b) by 685 days.

(21) Appl. No.: 17/478,466

(22) Filed: Sep. 17, 2021

(65) Prior Publication Data

US 2022/0112704 A1  Apr. 14, 2022

Related U.S. Application Data

(60) Provisional application No. 63/142,837, filed on Jan. 28, 2021, provisional application No. 63/090,995, filed on Oct. 13, 2020.

(51) Int. Cl.
*E03D 9/00*  (2006.01)
*A47K 13/30*  (2006.01)
(Continued)

(52) U.S. Cl.
CPC ............ *E03D 9/005* (2013.01); *A47K 13/302* (2013.01); *A61L 9/14* (2013.01); *A61L 9/20* (2013.01);
(Continued)

(58) Field of Classification Search
CPC ....................................................... E03D 9/005
(Continued)

(56) References Cited

U.S. PATENT DOCUMENTS 4,063,316 A  12/1977  Hunninghaus
4,536,899 A  8/1985  Schnyder
(Continued)

FOREIGN PATENT DOCUMENTS

CA  2079299 A1  3/1994
CN  2758343 Y  2/2006
(Continued)

OTHER PUBLICATIONS

Extended European Search Report from European Patent Application No. 21199988.3, Dated Feb. 17, 2022, 8 pages.
(Continued)

*Primary Examiner* — Lauren A Crane
(74) *Attorney, Agent, or Firm* — Lempia Summerfield Katz LLC

(57) ABSTRACT

A plume cleaning system for a toilet is integrated with a toilet. In one example, a plume cleaner assembly adjacent to a toilet seat is independently removable with respect to the toilet seat. The plume cleaner assembly may include a plume cleaner, apertures, and a fan positioned to draw plume air through the plurality of apertures for treatment by the plume cleaner and expel the treated plume air out of the plume cleaner assembly in a direction at an angle to the apertures. In another example, a plume cleaner assembly with the toilet seat may include at least a fan, an electrostatic collector, and a mist generator. In another example, a plume cleaner assembly is integrated in a tank of the toilet to generate a sanitization fluid that is channeled into the toilet bowl through an overflow tube and/or rim channels.

17 Claims, 44 Drawing Sheets

(51) Int. Cl.
*A61L 9/14* (2006.01)
*A61L 9/20* (2006.01)

(52) U.S. Cl.
CPC ...... *A61L 2209/111* (2013.01); *A61L 2209/12* (2013.01)

(58) Field of Classification Search
USPC .......................................................... 4/213
See application file for complete search history.

(56) References Cited

U.S. PATENT DOCUMENTS

| | | | |
|---|---|---|---|
| 4,586,201 A * | 5/1986 | Todd, Jr. ................ | E03D 9/052 4/213 |
| 4,745,639 A | 5/1988 | Wileman, III | |
| 4,790,036 A | 12/1988 | Vogeli et al. | |
| 4,790,039 A | 12/1988 | Speer | |
| 4,873,729 A | 10/1989 | Micallef | |
| 4,944,045 A | 7/1990 | Agelatos et al. | |
| 4,953,238 A | 9/1990 | Shifferly | |
| 5,031,252 A | 7/1991 | Oyama | |
| 5,105,479 A | 4/1992 | Ross | |
| 5,288,306 A | 2/1994 | Aibe et al. | |
| 5,355,537 A | 10/1994 | Redford | |
| 5,539,937 A | 7/1996 | Barefoot | |
| 5,727,262 A | 3/1998 | Littlejohn | |
| 6,076,197 A | 6/2000 | Yeung | |
| 6,163,893 A | 12/2000 | Lo | |
| 6,330,723 B1 | 12/2001 | Orgias | |
| 6,622,315 B1 | 9/2003 | Feygin et al. | |
| 6,701,538 B2 | 3/2004 | Hunnicutt, Jr. et al. | |
| 7,028,346 B2 | 4/2006 | Ermini | |
| 7,103,925 B2 | 9/2006 | Toth | |
| 7,596,818 B2 | 10/2009 | Sutton | |
| 7,730,559 B2 | 6/2010 | Gallizia | |
| 7,976,600 B1 | 7/2011 | Safuto | |
| 8,069,501 B2 | 12/2011 | Casson et al. | |
| 8,136,171 B2 | 3/2012 | Huang | |
| 8,239,973 B1 * | 8/2012 | Character ............ | A47K 13/307 4/219 |
| 8,381,321 B2 | 2/2013 | Nishizaki et al. | |
| 8,607,472 B2 | 12/2013 | Ishii et al. | |
| 8,709,137 B2 | 4/2014 | Chan et al. | |
| 8,769,729 B2 | 7/2014 | Nishimura et al. | |
| 8,776,278 B1 | 7/2014 | Dorra | |
| 8,813,383 B2 | 8/2014 | Liu et al. | |
| 8,993,988 B2 | 3/2015 | Nathan et al. | |
| 9,078,936 B1 | 7/2015 | Denby, Jr. | |
| 9,192,686 B2 | 11/2015 | Graydon | |
| 9,421,291 B2 | 8/2016 | Robert et al. | |
| 9,481,990 B2 | 11/2016 | Sollami | |
| 9,506,696 B2 | 11/2016 | Seibt | |
| 9,532,687 B2 | 1/2017 | Sollami | |
| 9,538,886 B2 | 1/2017 | Ros Marín | |
| 9,572,902 B2 | 2/2017 | Nathan et al. | |
| 9,642,505 B2 | 5/2017 | Bayley et al. | |
| 9,757,486 B2 | 9/2017 | Dobrinsky et al. | |
| 9,808,132 B2 | 11/2017 | Smith | |
| 9,861,239 B1 | 1/2018 | Robinson | |
| 9,877,623 B2 | 1/2018 | Sollami | |
| 10,100,501 B2 | 10/2018 | Figurski et al. | |
| 10,145,094 B2 | 12/2018 | Komatsu et al. | |
| 10,172,498 B2 | 1/2019 | Bayley et al. | |
| 10,206,548 B1 | 2/2019 | Hall et al. | |
| 10,299,641 B2 | 5/2019 | Käppeli et al. | |
| 10,369,239 B2 | 8/2019 | Dobrinsky et al. | |
| 10,398,793 B2 | 9/2019 | Foster | |
| 10,455,992 B2 | 10/2019 | Satermo | |
| 10,548,439 B2 | 2/2020 | Gagnon et al. | |
| 10,557,259 B2 | 2/2020 | Park et al. | |
| 10,563,388 B2 | 2/2020 | Nogoshi et al. | |
| 10,570,599 B2 | 2/2020 | Nogoshi et al. | |
| 10,584,469 B2 | 3/2020 | Nogoshi et al. | |
| 10,590,639 B2 | 3/2020 | Nogoshi et al. | |
| 10,597,857 B2 | 3/2020 | Nogoshi et al. | |
| 10,743,727 B2 | 8/2020 | Viöl et al. | |
| 10,767,357 B2 | 9/2020 | Kazes | |
| 10,787,801 B1 | 9/2020 | Lovins | |
| 10,918,748 B2 | 2/2021 | Childress et al. | |
| 2006/0021121 A1 | 2/2006 | Moussa | |
| 2008/0052952 A1 | 3/2008 | Nelson | |
| 2008/0060119 A1 | 3/2008 | Pinizzotto | |
| 2010/0101008 A1 | 4/2010 | Casson | |
| 2012/0227171 A1 | 9/2012 | Lopez | |
| 2013/0283629 A1 | 10/2013 | Bueker | |
| 2014/0294680 A1* | 10/2014 | Sevy .................. | A61L 9/14 422/121 |
| 2015/0306533 A1* | 10/2015 | Matlin .................. | F24F 8/158 96/417 |
| 2016/0059244 A1 | 3/2016 | Rexach et al. | |
| 2016/0237669 A1 | 8/2016 | Mullens | |
| 2017/0107709 A1 | 4/2017 | Kausch et al. | |
| 2017/0254526 A1* | 9/2017 | Hall .................. | F21V 3/00 |
| 2017/0341602 A1 | 11/2017 | Seibt | |
| 2018/0064833 A1 | 3/2018 | Childress et al. | |
| 2018/0325336 A1 | 11/2018 | Chang | |
| 2019/0117802 A1 | 4/2019 | Hishinuma et al. | |
| 2019/0125917 A1* | 5/2019 | Kim .................. | B01D 53/885 |
| 2019/0336629 A1 | 11/2019 | Dobrinsky et al. | |
| 2019/0338148 A1 | 11/2019 | Maa et al. | |
| 2019/0387934 A1 | 12/2019 | Desheng | |
| 2020/0015642 A1 | 1/2020 | Yu | |
| 2020/0030472 A1 | 1/2020 | Kim et al. | |
| 2020/0046179 A1 | 2/2020 | Satermo | |
| 2020/0054179 A1 | 2/2020 | Ruehle | |
| 2020/0173156 A1 | 6/2020 | Kazes | |
| 2020/0199860 A1 | 6/2020 | Giertz et al. | |
| 2020/0263407 A1 | 8/2020 | Berger | |
| 2020/0313547 A1 | 10/2020 | Higashida et al. | |
| 2020/0337509 A1 | 10/2020 | Ho | |

FOREIGN PATENT DOCUMENTS

| | | |
|---|---|---|
| CN | 201033893 Y | 3/2008 |
| CN | 204520482 U | 8/2015 |
| CN | 103356115 B | 10/2015 |
| CN | 205286231 U | 6/2016 |
| CN | 205935117 U | 2/2017 |
| CN | 206026213 U | 3/2017 |
| CN | 108915054 A | 11/2018 |
| CN | 110130450 A | 8/2019 |
| CN | 110446446 A | 11/2019 |
| CN | 209989887 U | 1/2020 |
| CN | 210130772 U | 3/2020 |
| CN | 210408238 U | 4/2020 |
| CN | 210520885 U | 5/2020 |
| CN | 210797776 U | 6/2020 |
| CN | 210842794 U | 6/2020 |
| CN | 211158095 U | 8/2020 |
| CN | 211271243 U | 8/2020 |
| DE | 10258120 A1 | 6/2004 |
| DE | 102017001723 A1 | 8/2018 |
| EP | 0447395 B1 | 4/1993 |
| FR | 3044537 A1 | 6/2017 |
| GB | 2478729 A | 9/2011 |
| GB | 2505863 A | 3/2014 |
| JP | H0661319 B2 | 3/1988 |
| JP | H0725072 U | 5/1995 |
| JP | H0725073 U | 5/1995 |
| JP | 2822740 B2 | 11/1998 |
| JP | 2001169962 A | 6/2001 |
| JP | 3812322 B2 | 6/2006 |
| JP | 3976074 B2 | 9/2007 |
| JP | 4013067 B2 | 9/2007 |
| JP | 2007224714 A | 9/2007 |
| JP | 2012019809 A | 2/2012 |
| JP | 5192709 B2 | 2/2013 |
| JP | 2013244248 A | 12/2013 |
| JP | 5810277 B2 | 10/2015 |
| JP | 2016148187 A | 8/2016 |
| JP | 2016158960 A | 9/2016 |
| JP | 6072309 B2 | 1/2017 |
| JP | 6099219 B2 | 3/2017 |
| JP | 6300180 B2 | 3/2018 |

(56) References Cited

FOREIGN PATENT DOCUMENTS

| | | |
|---|---|---|
| JP | 6459157 B2 | 1/2019 |
| JP | 2019166279 A | 10/2019 |
| JP | 6703394 B2 | 5/2020 |
| KR | 19990008653 U | 3/1999 |
| KR | 20010007902 A | 2/2001 |
| KR | 20010025444 A | 4/2001 |
| KR | 20010025690 A | 4/2001 |
| KR | 200316420 Y1 | 6/2003 |
| KR | 20040045179 A | 6/2004 |
| KR | 100568252 B1 | 4/2006 |
| KR | 20090053003 A | 5/2009 |
| KR | 20110124832 A | 11/2011 |
| KR | 20120025841 A | 3/2012 |
| KR | 20130096570 A | 8/2013 |
| KR | 101365125 B1 | 2/2014 |
| KR | 101671743 B1 | 11/2016 |
| KR | 20160135502 A | 11/2016 |
| KR | 101728672 B1 | 4/2017 |
| KR | 101796266 B1 | 11/2017 |
| KR | 101953557 B1 | 3/2019 |
| NL | 2021182 B1 | 1/2020 |
| WO | 2008024005 A2 | 2/2008 |
| WO | 2000027269 A1 | 5/2008 |
| WO | 2010089925 A1 | 8/2010 |
| WO | 2010089927 A1 | 8/2010 |
| WO | 2014024552 A1 | 2/2014 |
| WO | 2014129755 A1 | 8/2014 |
| WO | 2016156861 A1 | 10/2016 |

OTHER PUBLICATIONS

Chinese Office Action from Chinese Patent Application No. 202111187613.7, dated Aug. 3, 2024, 13 pages (including English summary).

Chinese Office Action from Chinese Patent Application No. 202111187613.7, dated Jan. 11, 2024, 13 pages (including English summary).

* cited by examiner

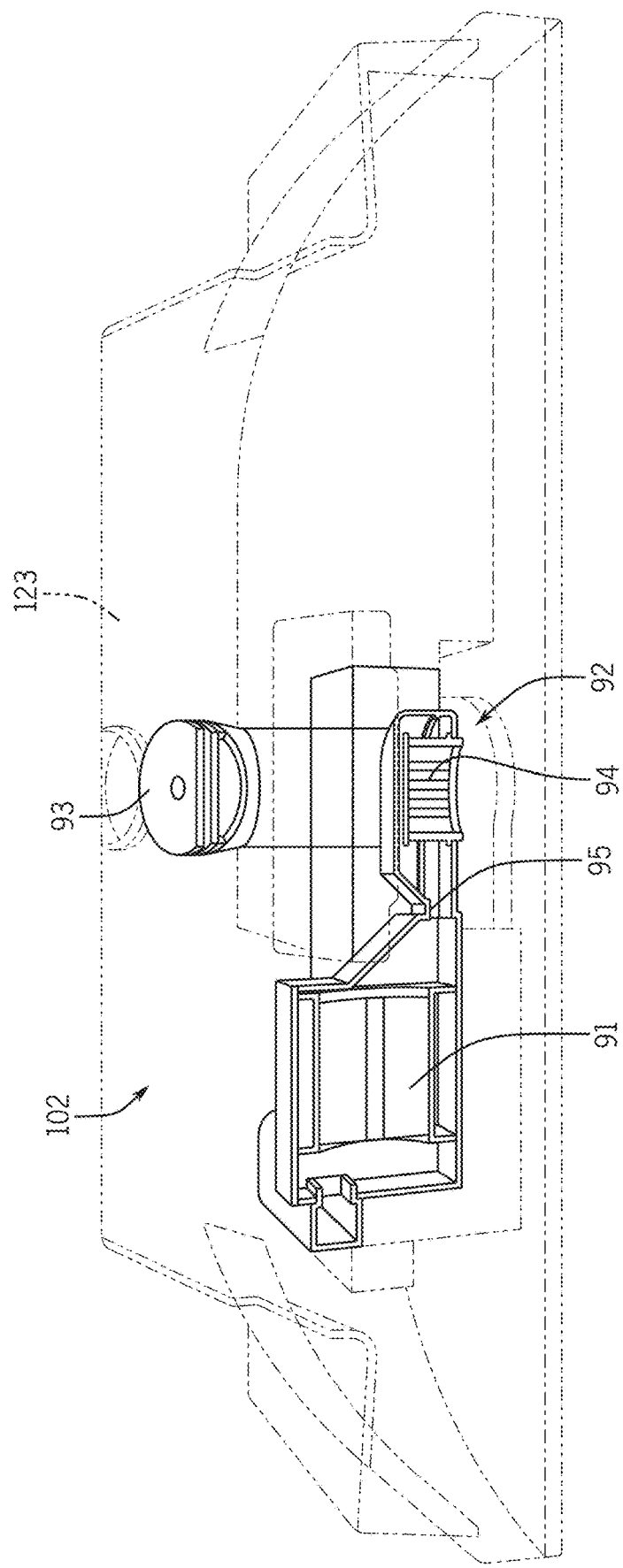

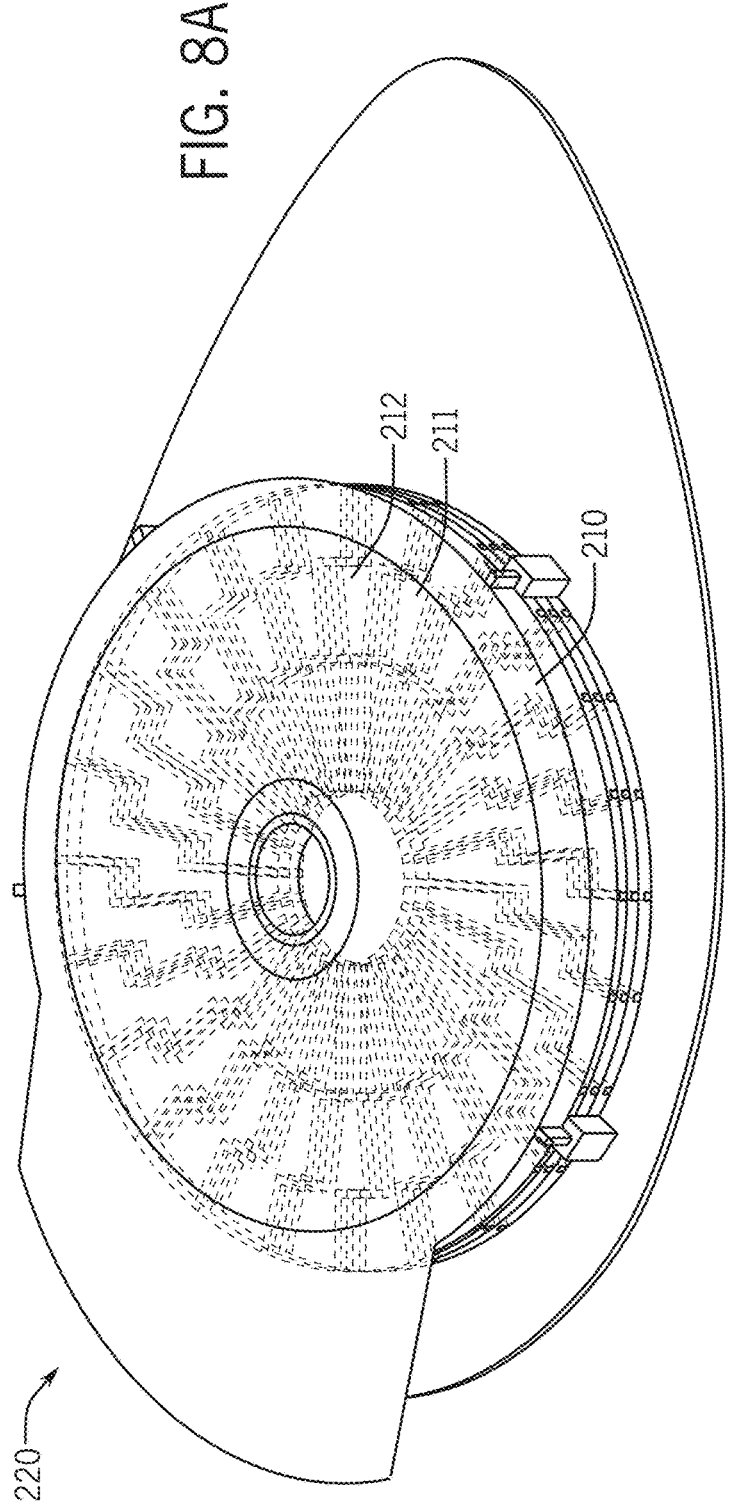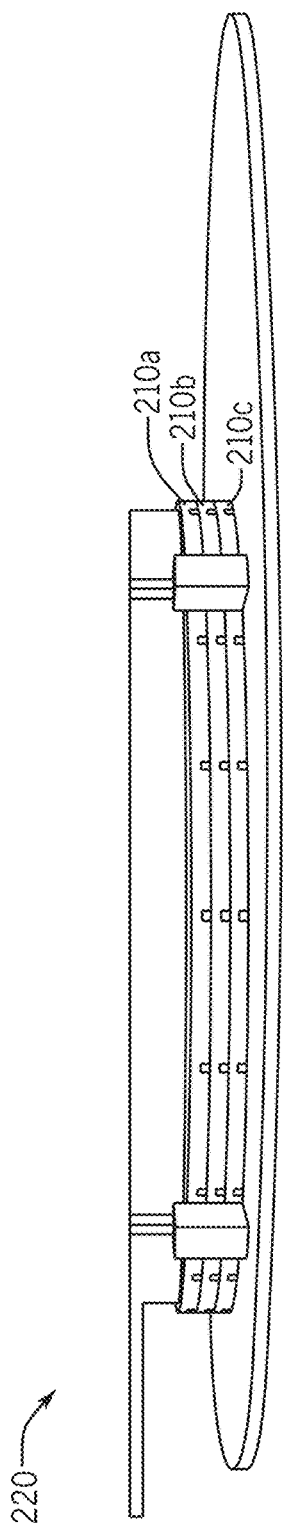

S201

Generate a mist from a liquid at a mist generator.

S203

Draw a cloud of air including at least a portion of the mist through a fan inlet.

S205

Provide the cloud of air to an electrostatic collector.

S207

Collect particles from the cloud of air at the electrostatic collector.

S209

Recirculate the cloud from the electrostatic collector to the mist generator.

FIG. 36

SANITIZATION SYSTEM

CROSS-REFERENCE TO RELATED APPLICATIONS

This application claims priority benefit to U.S. Provisional Utility Application Ser. No. 63/090,995 entitled "CLEAN SEAT," filed on Oct. 13, 2020, and U.S. Provisional Utility Application Ser. No. 63/142,837 entitled "SANITIZATION SYSTEM," filed on Jan. 28, 2021. The entire disclosure of each is hereby incorporated by reference.

FIELD

The present application relates generally to a sanitization system for use in a bathroom (e.g., a toilet, fan, hair dryer, or other appliance).

BACKGROUND

Generally, air includes very small particles or droplets that are suspended in the air. These aerosols are particularly prevalent in enclosed spaces, and even more prevalent in enclosed spaces with water usage. For example, in a bathroom, aerosols may be expelled from several places, not the least of which is the toilet.

Aerosols may be removed from the air that humans breath by the human body's respiratory system. However, some aerosols may be toxic or even carry a virus into the human body. The problem of aerosols may be mitigated through sanitization of the air. In addition, from use, scale (e.g., urine scale), minerals, bacteria, and other undesirable deposits (e.g., biofilm) build-up on the surfaces of toilets and, in particular, on the inner surfaces of the bowl. Moreover, these deposits may become lodged in small imperfections in the inner surfaces of the toilet, which may be a vitreous material. These built-up deposits can lead to undesirable odors and stains, as well as harbor germs and bacteria. It would be advantageous to provide a toilet having internal cleaning systems that provide improved cleanliness to address the aforementioned problems.

SUMMARY

At least one embodiment includes, a plume cleaning system for a toilet, the plume cleaning system including a toilet seat cover, a toilet seat, and a plume cleaner assembly adjacent to the toilet seat cover and the toilet seat and independently removable with respect to the toilet seat cover and with respect to the toilet seat. The plume cleaner assembly includes a plume cleaner, a plurality of apertures arranged with longitudinal axes, and a fan positioned to draw plume air through the plurality of apertures for treatment by the plume cleaner and expel the treated plume air out of the plume cleaner assembly in a direction at an angle to the longitudinal axes of the plurality of apertures. At least a portion of the plume cleaning assembly may be below the toilet seat.

At least one embodiment includes a rounded housing including the plurality of apertures. The rounded housing may have circular or oval cross section. At least one embodiment includes at least one radial channel configured to direct the plume air from a toilet bowl to the plurality of apertures. At least one embodiment includes a light source configured to irradiate the plume air in the at least one radial channel. At least one embodiment includes an output channel configured to direct the treated plume air to the fan. At least one embodiment includes a bulkhead having a shape corresponding to an opening of the toilet seat, the bulkhead supporting at least the plume cleaner. The plume cleaner assembly adjacent to the toilet seat cover includes a cavity configured to receive a light source that is mounted to the toilet sear cover. The plume cleaner assembly adjacent to the toilet seat cover includes a transparent portion to provide a light path from a light source to at least one radial channel.

At least one embodiment includes a cleaner dock coupled to the toilet seat cover and configured to removably attach the plume cleaner assembly to the toilet seat cover. The plume cleaner may include any one or a combination of an impactor module, electrostatic module, a hydroxyl module, and a multi-cyclone module.

At least one embodiment includes a method for mitigating a plume from a toilet including receiving data indicative of toilet seat usage, generating, in response to the data indicative of toilet seat usage, a mist configured to adhere to particles in the plume expelled from the toilet, and applying a conditioning to the mist. The data indicative of toilet seat usage may include a status of a predetermined time period. The data indicative of toilet seat usage may include motion sensor data or pressure sensor data.

At least one embodiment includes applying light from a light source to the mist. At least one embodiment includes displaying a status of a cleaning cycle in response to the mist generation.

At least one embodiment includes an apparatus for improving air quality in an environment of a toilet including a seat, attached to a bowl of the toilet and rotatable between a raised position and a closed position, wherein a space between the bowl and the seat includes a plume cleaning space, a lid including a plurality of divided cavities comprising a misting cavity, wherein the seat at least partially encloses the misting cavity in a lowered position, and a plume cleaning cavity aligned with the bowl; and at least one atomizer configured to generate a negative relative air pressure in the misting cavity, wherein the negative relative air pressure prevents airflow into the misting cavity from the plume cleaning cavity or an ambient environment.

At least one embodiment includes, a mister body configured to receive a flow of liquid and meter the flow of liquid and a horn configured to receive the metered liquid from the horn and a predetermined vibration to create standing waves that cause the metered liquid to atomize and exit the horn.

At least one embodiment includes a piezoelectric element configured to convert an electrical signal to the predetermined vibration. At least one embodiment includes an interdigital transducer configured to generate a surface acoustic wave that causes liquid to mist and exit the atomizer. At least one embodiment includes a power circuit configured to provide a radio frequency signal to the surface acoustic wave, and a driving circuit configured to control an actuating device to meter a flow of liquid into the atomizer. At least one embodiment includes a misting wand configured to provide a mist in a configurable predetermined direction. At least one embodiment includes a solution reservoir configured to deliver a solution to the at least one atomizer. At least one embodiment includes a feed line connected to each of the plurality of atomizers. At least one embodiment includes a solution reservoir configured to deliver a solution to the plurality of atomizers through the feed line. The plurality of divided cavities in the lid may include a seat cavity configured to at least partially surround the seat. At least one embodiment includes a cleaner dock coupled to the lid and configured to removably attach a plume cleaner assembly to a toilet seat cover to position the plume cleaner assembly in the plume cleaning cavity. At least one embodiment includes a light source coupled to the lid and facing the plume cleaner assembly. At least one embodiment includes a chamber between the misting cavity and the plume cleaning cavity.

At least one embodiment includes a plume cleaner including a removable assembly. At least one embodiment includes an impactor module, hydroxyl module, a multi-cyclone module, and/or an electrostatic module. The electrostatic module includes a plurality of fins. The electrostatic module includes a passive static charge.

At least one embodiment includes an apparatus for irradiation of a plume from a toilet including a toilet seat cover, a toilet seat, a serpentine plume path through a plume assembly between the toilet and the toilet seat cover or between the toilet and the toilet seat, the serpentine plume path configured to receive plume air from the toilet and guide the plume air through a plurality of turns, and a light source configured to irradiate the plume air of the serpentine plume path. The light may be an ultraviolet light. The serpentine plume path may include a first portion in a first direction and a second portion in a second direction, wherein the first portion and the second portion share a wall. The serpentine plume path may include a first path portion that is substantially vertical path toward a horizontal obstacle and a second path portion that is substantially horizontal and parallel to the horizontal obstacle. The serpentine plume path may include a third path portion around the horizontal obstacle and a forth path portion away from the horizontal obstacle. The serpentine plume path includes a coil. The serpentine plume path may include a series of chambers with staggered apertures between the series of chambers. At least one of the apertures includes a valve to flow the plume air.

At least one embodiment includes a plume cleaner assembly adjacent to the toilet seat cover and the toilet seat and independently removable with respect to the toilet seat cover and with respect to the toilet seat, the plume cleaner assembly comprising the serpentine plume path or the light source. The plume cleaner assembly includes an impactor module, an electrostatic module, a hydroxyl module, and/or a multi-cyclone module. The electrostatic module includes a plurality of fins, which may be have a passive static charge applied thereon.

At least one embodiment includes a mist generator configured to expel a mist into a bowl of the toilet. The mist generator includes a piezoelectric element and/or an atomizer.

At least one embodiment includes a toilet bowl, a toilet seat, a toilet seat cover configured to enclose a volume of air adjacent to the toilet seat and including the toilet bowl, and a serpentine plume path through a plume assembly positioning within the volume of air, the serpentine plume path configured to receive plume air from the toilet and guide the plume air through a plurality of turns. At least one embodiment includes a light source configured to irradiate the plume air of the serpentine plume path.

At least one embodiment includes an apparatus for sanitization of a plume from a toilet, the apparatus comprising an impactor including a collection surface, a plurality of apertures configured to receive aerosols from the toilet and guide the aerosols to the collection surface, and a sanitization device directed at the collection surface. One or more particles from the aerosols are deposited on the collection surface in response to a change in direction of the aerosols caused by the impactor. The sanitation device is an ultraviolet light. The impactor may be between the sanitization device and the toilet. The impactor maybe at least partially transparent. The impactor may include a catalyst.

At least one embodiment includes a toilet seat cover, a toilet seat, and a plume cleaner assembly adjacent to the toilet seat cover and the toilet seat and independently removable with respect to the toilet seat cover and with respect to the toilet seat. The plume cleaner assembly comprises the impactor. The plume cleaner assembly comprises the sanitization device.

At least one embodiment includes an apparatus for guiding a plume from a toilet, the apparatus comprising a first circular aperture, a second circular aperture having a diameter greater than a diameter of the first circular aperture, a first wall extending from the first circular aperture to the second circular aperture, a first pipe extending from the second circular aperture to a third circular aperture, a second pipe having a diameter less than the diameter of the second circular aperture and disposed in the first pipe a distance away from said second aperture, and a wall located outside of said first pipe and at least partially encircling the second pipe. A diameter of the third circular aperture may be the same as the diameter of the second circular aperture.

At least one embodiment includes an apparatus for cleaning a plume from a toilet, the apparatus including a housing, having an internal chamber, rotatably attached to the toilet, a photocatalytic filter contained in the housing, and an ultraviolet light source illuminating the photocatalytic filter. The photocatalytic filter may include a mesh, honeycomb, or bead structure. At least one embodiment includes a fan configured to draw a plume from the toilet across the photocatalytic filter, wherein the photocatalytic filter, is activated, at least in part, by the plume from the toilet. The photocatalytic filter is activated, at least in part, by the plume from the ultraviolet light.

At least one embodiment includes, an apparatus for cleaning a plume from a toilet, the apparatus comprising: a housing rotatably attached to a toilet, wherein the housing has an internal chamber, a first aperture located on a first side of the housing, a second aperture located on a second side of the housing, a fan, located in the housing, configured to draw air through the first aperture and expelling air through the second aperture, a device for imparting an electrostatic charge on air flowing through the first aperture, and a surface, having a charge opposite of the charge imparted on the air flowing through the first aperture.

At least one embodiment includes an apparatus for mist generation in a tank of a toilet, the apparatus comprising: a mister housing within the tank of the toilet, and a conditioning unit that generates mist and provides the mist through at least one channel of the toilet. The conditioning unit may include a piezoelectric element. The conditioning unit may include an atomizer. At least one embodiment includes a vent that provides a flow of air into the mister housing. At least one embodiment includes a tube connecting the conditioning unit to an overflow mechanism, wherein the conditioned flow flows through the overflow mechanism to the at least one channel of the toilet. The conditioning unit may include a horn and/or a fan.

At least one embodiment includes an apparatus for cleaning an air flow of a hand dryer, the apparatus comprising: a chemical reservoir configured to store and dispense a solution, a mister coupled to the chemical reservoir and configured to receive the solution and generate a mist from the solution, a catalytic foam configured to adsorb particles from the mist, and a light array configured to irradiate the mist or activate the catalytic foam.

At least one embodiment includes a fan configured to draw the mists through the catalytic foam. The fan further inflates a towel attached to the hand dryer. The towel inflates and is not removable from the hand dryer.

At least one embodiment includes an apparatus for improving air quality in an environment of a toilet, the apparatus comprising: a mist generator configured to convert mechanical energy and a liquid to a mist, an electrostatic collector including a collector inlet path and a collector outlet path, and a fan configured to draw in a cloud of air including at least a portion of the mist from the mist generator through a fan inlet and provide the cloud of air to a fan outlet to the electrostatic collector, wherein the electrostatic collector removes particles from the cloud. A recirculation path through the apparatus includes the collector inlet path, the collector outlet path, the fan inlet and the fan outlet. The particles removed by the electrostatic collector include at least one particle from the mist and at least one particle from a toilet plume. At least one embodiment includes a tank including the liquid. The liquid may include a chemical.

At least one embodiment includes a chamber coupled to the collector inlet path the fan outlet. The electrostatic collector may include a plurality of fins. The electrostatic collector may be permanently charged with a static charge. At least one embodiment includes a controller configured to operate the fan and the mist generator. The controller turns on the fan and the mist generator in a recirculation cycle. At least one embodiment includes a user input configured to trigger the recirculation cycle. At least one embodiment includes a sensor configured to collect data, wherein the controller trigger the recirculation cycle in response to the collected data. The sensor detects a user in a vicinity of the toilet, a toilet plume, and/or a state of a toilet seat of the toilet.

At least one embodiment includes a method including generating, at a mist generator, a mist from a liquid, drawing a cloud of air including at least a portion of the mist from the mist generator through a fan inlet, and providing the cloud of air to an electrostatic collector, wherein the electrostatic collector removes particles from the cloud. At least one embodiment includes collecting particles at the electrostatic collector from the cloud using a static charged electrode. The electrostatic collector may be permanently charged with a static charge. At least one embodiment includes generating, at a controller, a fan command to operate the fan. At least one embodiment includes generating, at the controller, a misting command to operate the mist generator. The fan command and the misting command may be part of a recirculation sequence. At least one embodiment includes receiving sensor data at the controller, wherein the recirculation sequence is triggered based on the sensor data.

BRIEF DESCRIPTION OF THE DRAWINGS

Exemplary embodiments are described herein with reference to the following drawings, according to an exemplary embodiment.

FIG. 1E illustrates an example electrostatic collection device for the sanitization system.
FIGS. 8A, 8B, 9A, and 9B illustrate another example impactor for the sanitization system.
FIG. 36 illustrates another example flow chart for the controller of FIG. 34.

DETAILED DESCRIPTION

The following embodiments includes systems, apparatus, and method for sanitization and/or disinfection of one or more surfaces and/or one or more spaces. These cleaning techniques may be applied to a toilet or another device found in the bathroom. For example, the following embodiments may be applied to a lavatory, a sink, a shower, a bathtub, or a bidet (e.g., floor standing bidet). Regarding the toilet, two specific areas that are targeted include management of the plume and sanitization of the surfaces of the toilet, or at least the surfaces that the human body comes in contact with. The plume is a cloud of microscopic particles or droplets dispersed into the air as a result of flushing the toilet. The plume may include bacteria, germs, or fecal matter. Every person who uses a toilet comes in contact with either the seat or lid. That person not only potentially spreads their germs to those surfaces but also has the risk of spreading the germs to others.

The plume may include particles of various sizes. The size of the particles in the plume may impact the potential travel distance when expelled by the toilet. Further, the size of the particles may impact how quickly the particles may settle on surfaces after they are expelled. For example, a particle with a 100 micron diameter may settle in a few seconds and a particle with a 1 micron diameter or smaller may remain airborne for hours. Viruses and bacteria may have diameters of 1 micron or less. Particles that remain airborne for longer times are more likely to be taken in by the human body. Particles that remain airborne for longer are times are more likely to still be airborne after one user of a bathroom has left and another has entered.

Figure 1A:
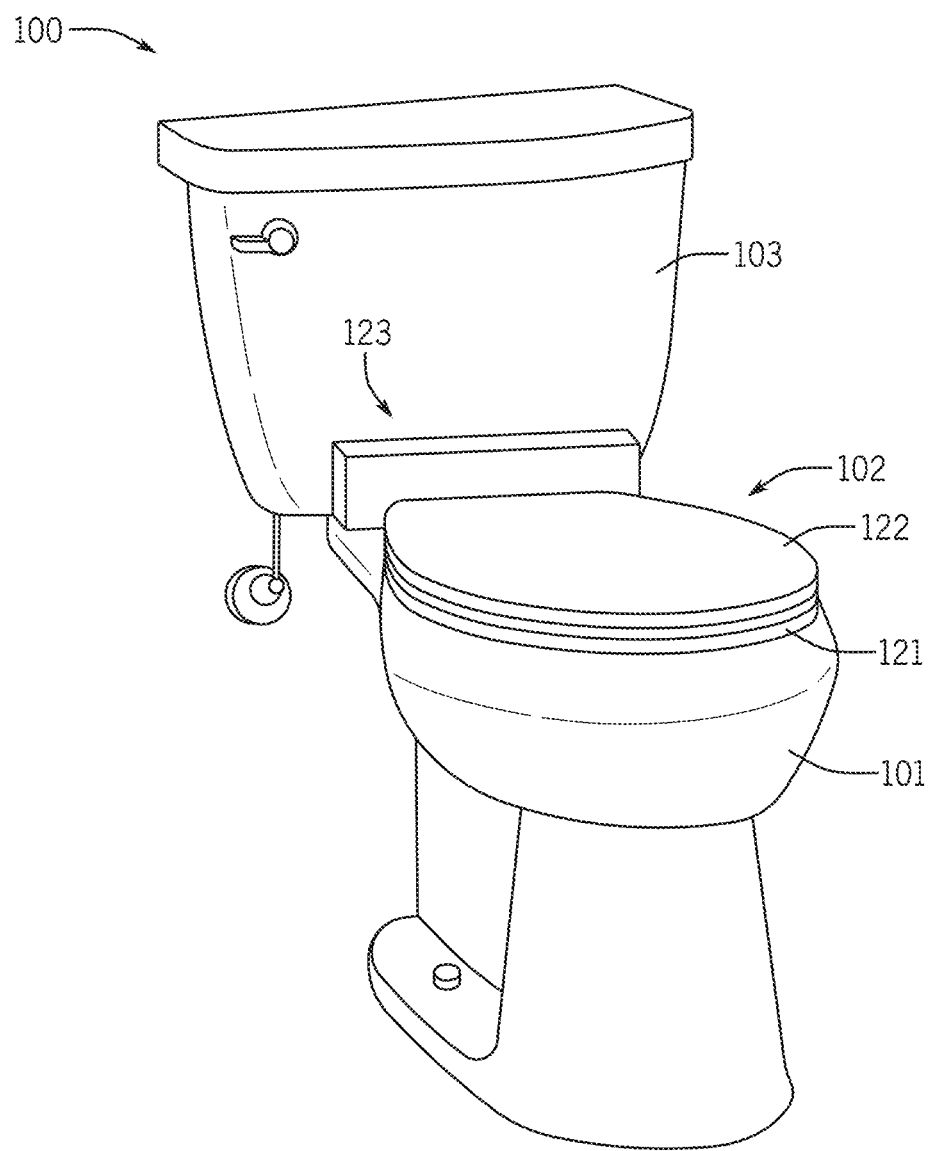
FIG. 1A illustrates a toilet.

FIG. 1A illustrates an exemplary embodiment of a toilet 100 that includes a bowl 101 (e.g., base, pedestal, etc.), a toilet seat assembly 102 coupled to an upper surface (e.g., a deck, a ledge, etc.) of the bowl 101, and a tank 103 for supplying water to the bowl 101. It is noted that the toilet seat assembly 102 and the embodiments disclosed herein may be employed with any type of toilet (e.g., one-piece toilets, two-piece toilets, skirted toilets, smart toilets, etc.) and that the toilet 100 shown in FIG. 1A is an example implementation. Further, the toilet 100 may be employed with any type of toilet seat assembly and/or toilet attachment assemblies (e.g., bidet assemblies, heated seats, smart devices, etc.). Also shown in FIG. 1A, the toilet seat assembly 102 includes a seat 121 configured to support a person, a lid 122 (e.g., cover, etc.) covering the seat 121, and a hinge 123 that rotatably couples the seat 121 and the lid 122 to the toilet 100 (e.g., the upper surface). A portion of the hinge 123 is mountable to the upper surface to secure the portion of the hinge 123 in place relative to the bowl 101 to allow independent rotation of the seat 121 and the lid 122 relative to the portion and the bowl 101. In addition, as discussed in more detail herein, the hinge 123 may also secure a plume cleaning system to the toilet 100, and the plume cleaning system may utilize a variety of sanitization, disinfecting, or other cleaning techniques to clean a plume of the toilet 100. In addition, or in the alternative, the plume cleaning system may couple to the lid 122 or the seat 121. The plume is a dispersion of microscopic particles or aerosols from the toilet 100. The plume may be forced out of the toilet bowl 101 due the normal flush cycle. That is, the addition of water (e.g., a flow of water) into the bowl may cause air flow, termed the plume, upward and out of the bowl 101.

Figure 1B:
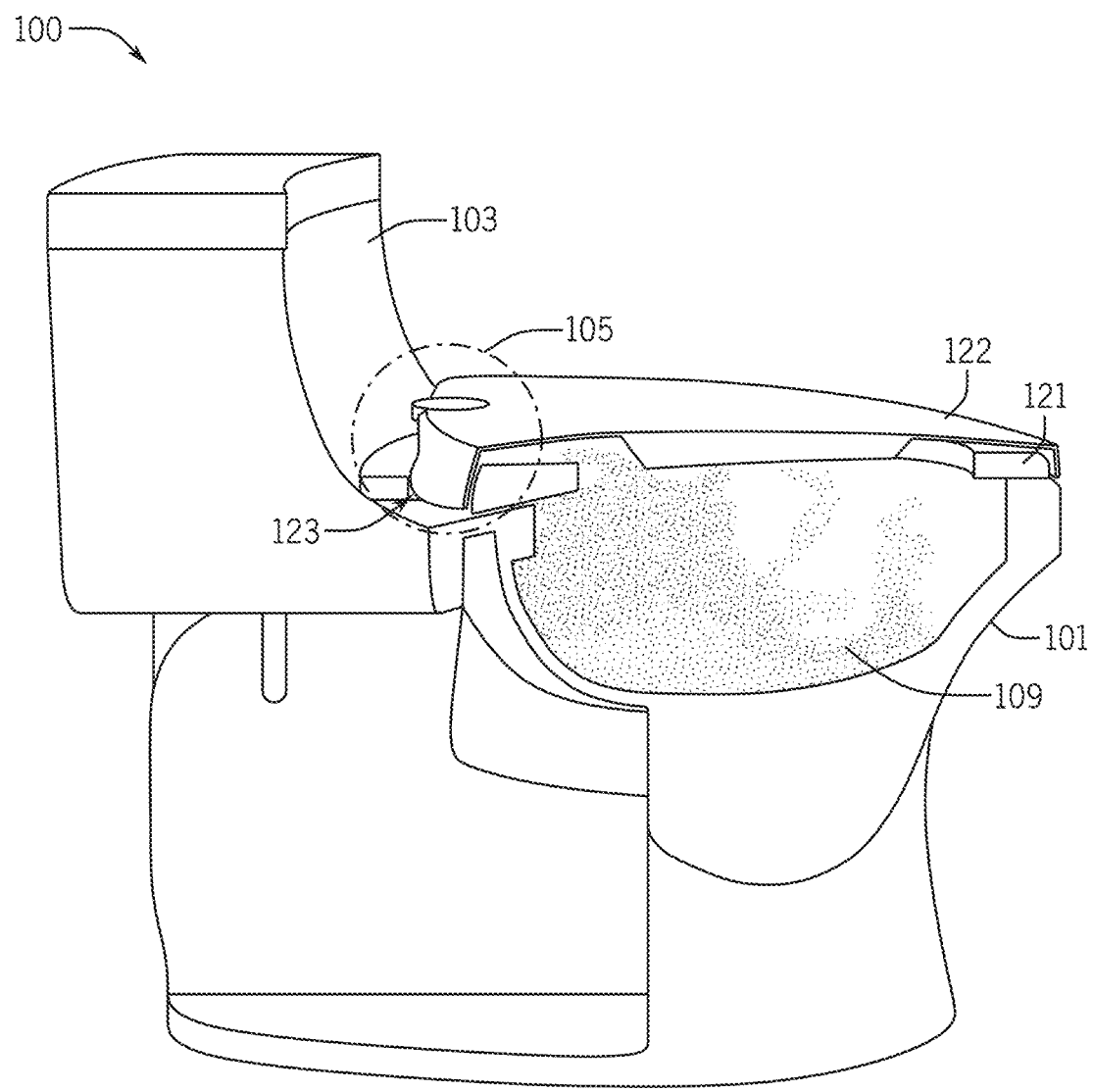
FIG. 1B illustrates a toilet including a sanitization system.
Figure 1C:
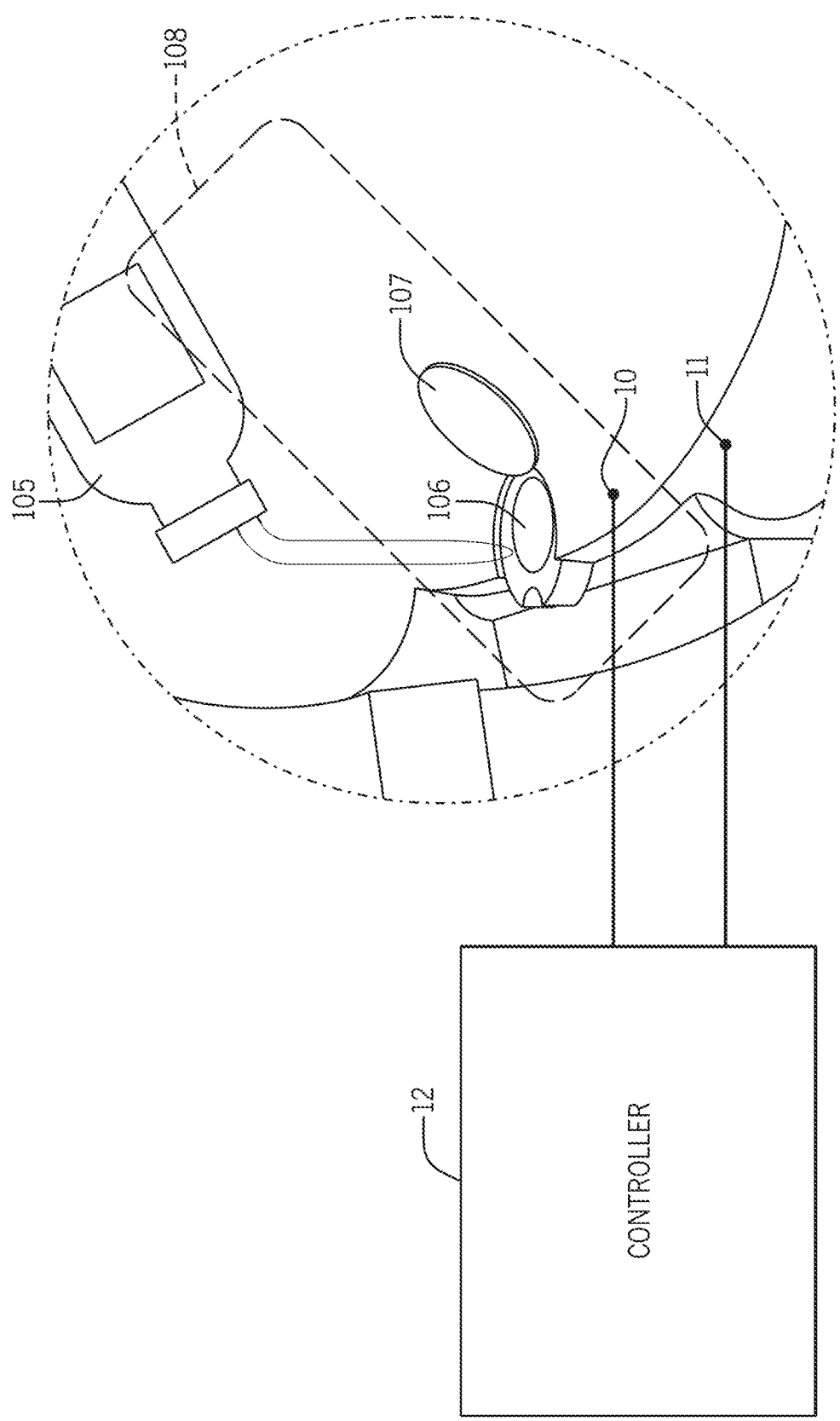
FIG. 1C illustrates an example fluid distribution for the sanitization system.

FIGS. 1B and 1C illustrate that the hinge may include a tank for storing disinfectant, sanitizing agent, or another solution. The tank includes an opening 106 configured to receive the disinfectant into the tank 108. The disinfectant may be hydrogen peroxide ($H_2O_2$). Hydrogen peroxide is antiviral and antibacterial. Hydrogen peroxide is an example antiseptic because hydrogen peroxide may kill bacteria cells by destroying the cell's walls. It is also more effective than chlorine bleach at reaching and killing mold on porous surfaces. To use as a disinfectant, hydrogen peroxide may be applied to the surface and simply allowed to air dry. Other solutions that may be stored in the tank 108 may include quaternary ammonium, tetraacetyl ethylenediamine, phenolic, isopropyl alcohol, sodium carbonate, peroxyhydrate; tetraacetyl ethylenediamine, ethanol, sodium hypochlorite, octanoic acid, or sodium chlorite. The solution stored in the tank may be selected from or include one or more ingredients selected from the "List N of Disinfectants maintained by the Centers for Disease Control" and available at https://cfpub.epa.gov/giwiz/disinfectants/index.cfm.

As one alternative to these chemical solutions, the tank 108 may include electrolyzed water. Electrolyzed water may be referred to as electrolyzed oxidizing water, electro-activated water or electro-chemically activated water solution. Electrolyzed water may be generated by the electrolysis of water (e.g., ordinary water or tap water) with dissolved sodium chloride therein. The electrolysis may produce hypochlorous acid and sodium hydroxide. The electrolysis may include apply a direct current (DC) power source connected to multiple electrodes plates constructed from electroconductive material such as metal.

Connected to the tank 108 or one or more other location of the toilet 100 is a misting distribution system that provides the disinfectant to the bowl 101. The distribution system may generate a mist or cloud 109. The mist may operate as a gas that expands in space to reach substantially every surface within the bowl 101. One example distribution system may be incorporated into the toilet seat assembly 102. The distribution system may include a filling and control portion 105. The filing and control portion 105, as better illustrated in FIG. 1C, may include a fill opening 106 that is opened or closed by fill cover 107. As discussed in more detail below, a user input 10 may include a button, switch, or keyboard for controlling the operation of the distribution system. The user input 10 may turn the distribution system on or off. The user input 10 may cause the distribution system to generate the mist or cloud 109. In addition or in the alternative, a sensor 11 may detect one or more characteristics of the ambient environment or the toilet. The sensor 11 may detect the existence of aerosols or particles in the vicinity of the toilet 100. The sensor 11 may detect an operation of the toilet 100 (e.g., flush cycle). A controller 12 may receive sensor data collected by the sensor 11, analyze the sensor data, and control the distribution system in responses to the analysis.

Figure 1D:
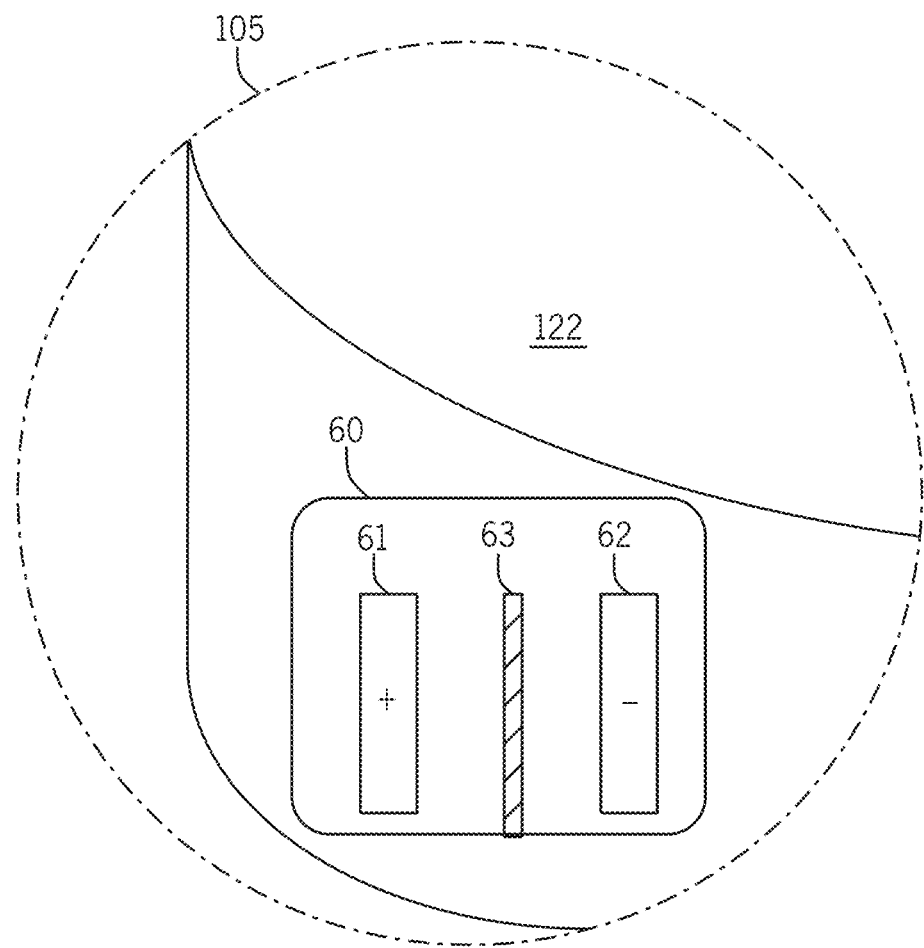
FIG. 1D illustrates an example electrolyzed water reactor for the sanitization system.

FIG. 1D illustrates an example electrolyzed water reactor 60 for the sanitization system. The electrolyzed water reactor 60 may perform electrolysis within tank 108 via a cathode 61 and anode 62. The tank 108 may include a separate housing that defines the reactor 60 and includes an anode compartment for the anode 62 and a cathode compartment for the cathode 61, which may be separated by a porous partition 63. In the anode compartment, a cleaning solution (alkaline) is produced, and in the cathode compartment, a sanitizing solution (acidic) is produced.

As a more specific example, at the cathode 61, hydrogen gas and hydroxide ions may be produced. At the anode 62, chloride ions may be oxidized into elemental chlorine. Near the cathode 61, the resulting alkaline solution is corrosive, and near the anode 62 the solution includes sodium hydroxide. A sanitizing agent may be produced when hypochlorous acid without elemental chlorine is formed at around neutral pH. A neutralizing agent (e.g., vinegar) may be added to reach a target pH range.

The controller turn on and off an electric current to the cathode 61 and/or the anode 62. The controller may provide a charge or bias to the cathode 61 to generate the electric current between the cathode 61 and the anode 62. The controller may operate a valve to add the neutralizing agent to the reactor 60 from a neutralizing agent compartment. The sanitizing solution may be an example disinfectant provided to the bowl 101.

Thus, in this examples, the disinfectant may be either generated at the toilet 100 (e.g., within the tank 108) or the disinfectant may be added to the tank 108 through refills at the filing and control portion 105 from a bottle or other container. User refills through the filing and control portion 105 simplify the apparatus required but require more intervention. Generation of the disinfectant (electrolyzed water) within the tank 108 requires more complex structure, including the reactor 60, but requires less user intervention.

FIG. 1E illustrates an example misting distribution system including a mist or fog generator 93. The misting distribution system may also include an electrostatic collection device 91 and a fan 92. The fog generator 93 may include an ultrasonic atomizer or transducer that converts high frequency sound waves into mechanical energy that is transferred into standing waves of the sanitizing liquid, causing a mist or fog to be emitted. The fog generator 93 may be coupled to the tank 108 to draw up liquid to create the mist or fog. The tank 108 may be coupled using a pump or a capillary tube.

The electrostatic collection device 91 may include a collector inlet path and a collector outlet path. The electrostatic collection device 91 may be formed of plastic and include a static charge (e.g., permanent static charge) on the surface of the plastic. The charge may be formed passively (e.g., through manufacturing or friction) or actively (e.g., power source). The electrostatic collect device 91 may include a plurality of fins having the charge. The fins may be arranged radially in a circle. Different fins may be positioned at different angles to the normal (e.g., vertical line or gravity). Small particles of dust and biological particles tend to form a charge, even if weak, on the surface of the particles. The electrostatic collection device 91 attracts and collects the particles. Air may travel into the electrostatic collection device 91 through the collector inlet path, be exposed to the static charge, and travel out of the electrostatic collection device 91 through the outlet path.

The combined mist and toilet plume are ingested by the fan 92 through the air intake 94 (fan inlet) of the fan and expelled by the fan 92 through the fan outlet. The combined mist and toilet plume circulate within a circulation chamber 95 and are provided to the electrostatic collection device 91. The plume of small particles are trapped by the electrostatic collection device 91 through the electrical charge on the that attracts the particles. The electrostatic collection device 91 provides the cleaned air (i.e., the combined mist and toilet plume with a substantial amount of particles removed) to the fog generator 93 as part of this recirculation path. The fog generator 93, which may be provided a flow of air from the fan 92, adds new mist particles to the cleaned air and provides the mist and air to the toilet bowl. Regardless of whether additional plume air is added (e.g., through flushing) the mist and air recirculation through this path to eliminate contaminants or other particles from the air.

One or more batteries may be included to power the fan 92 and/or the fog generator 93. The battery may be chargeable. The toilet seat assembly may include a charging port (e.g., universal serial bus or USB) for connecting the toilet seat assembly to a wall outlet or power cord. In one example, the electrostatic collection device 91 also includes an electrostatic rod or plate powered by the battery or the wall outlet.

In addition or in the alternative, connected to the toilet seat assembly 102 or one or more other locations of the toilet 100 is a modular plume cleaning system. The modular plume cleaning system incorporates a combination of multiple sanitization, disinfectant, or cleaning techniques. The modular plume cleaning system may include modules that are interchangeable and connect and disconnect from the toilet seat assembly 102. The sensor 11 may detect the existence of the plume or one or more characteristics of the plume. The sensor 11 may detect an operation of the toilet 100 (e.g., flush cycle). A controller 12 may receive sensor data collected by the sensor 11, analyze the sensor data, and control the distribution system in responses to the analysis.

Figure 2:
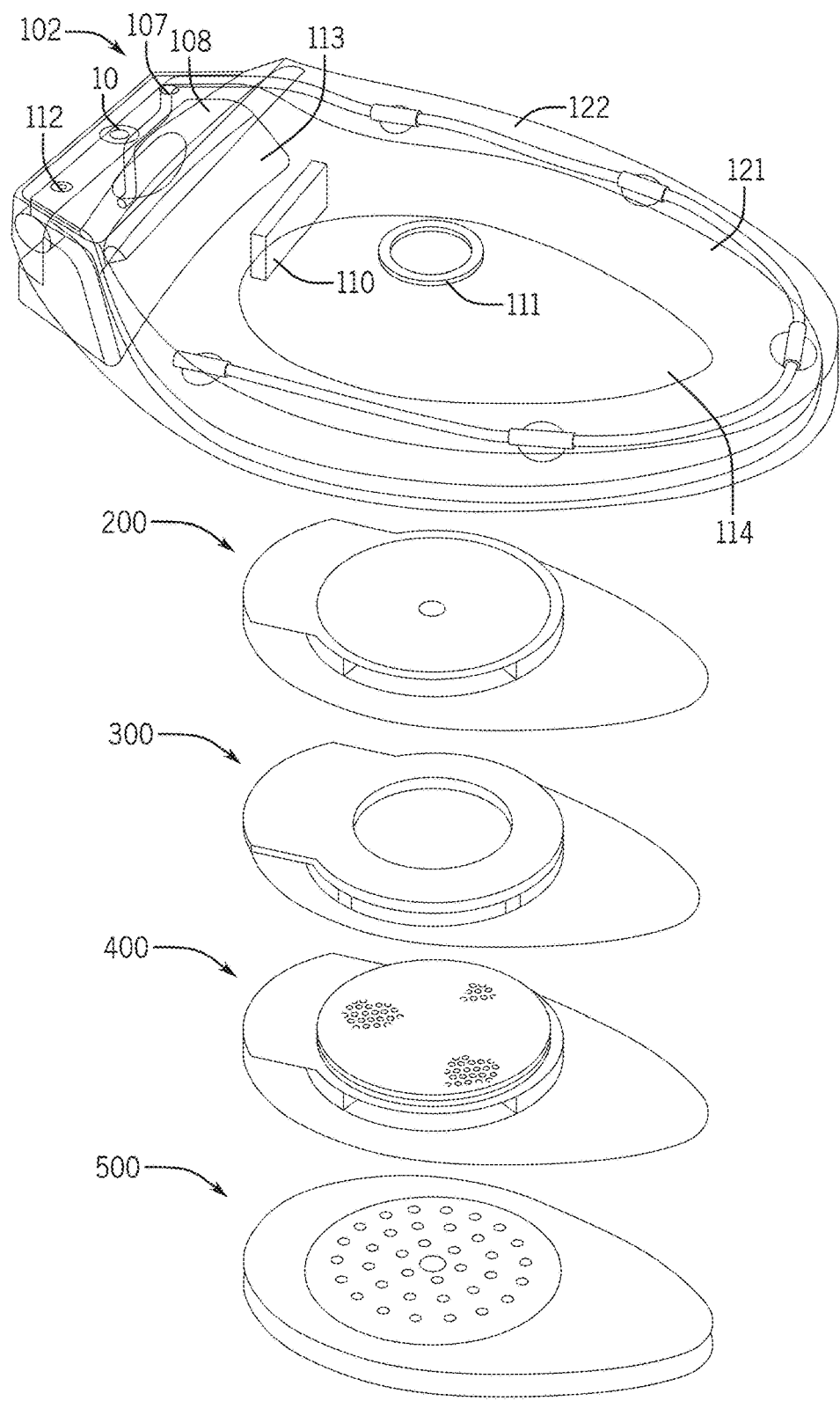
FIG. 2 illustrates a modular sanitization system for a toilet seat.

FIG. 2 illustrates a modular sanitization system for a toilet seat assembly 102. The toilet seat assembly 102 may include a fan 110, a module dock 111, a control panel indicator or light 112, a control panel input 10, a vent 113, and a bulkhead 114. The rear of the toilet seat assembly 102 may house the tank 108 for a cleaning solution or liquid. The tank 108 includes a fill opening with lid 107. In addition or in the alternative, the tank 108 may be secured to the toilet seat assembly 102 and/or capped by a tank cover 152 (illustrated in FIG. 5). Mounted on the rear housing, as shown in FIG. 2, or mounted elsewhere a control section may include the user input 10 and the light or indicator 112. Additional, different, or fewer components may be included.

The modular sanitization system of FIG. 2 includes an example plume cleaner assembly adjacent to the toilet seat cover 122 and the toilet seat 121 and independently removable with respect to the toilet seat cover 122 and with respect to the toilet seat 121. At least a portion of the plume cleaning assembly is below the toilet seat 121. That is, as discussed in more detail below, the plume cleaning assembly extends lower than the top edge of the toilet seat 121.

The plume cleaner assembly includes at least one removable module. Various modules may be used with the toilet seat 121. Examples pictured modules include an impactor module 200, an electrostatic module 300, a hydroxyl module 400, and a multi-cyclone module 500. The module may include one or more apertures or holes that provide a path for air from the interior of the toilet bowl 101 into the plume cleaner assembly. The apertures may have longitudinal axes arranged at a particular angle. The angle may be substantially in the direction of gravity. The modules may each include different examples of a reactor trap. The reactor trap traps particles from the plume, or from a mist expelled into the toilet bowl 101, or slows down the travel of these particles, so that they can be sanitized or otherwise cleaned, for example, by ultraviolet light.

The modules may be connected to the toilet seat 121 using the module dock 111. The modules may be connected to the toilet seat 121 and used to implement the modular sanitization system individually or in any combination. In some examples, the modules are stacked. The top module connected to the module dock 111. Below the top module another module is connected to the top module, and so on.

The modules may have a variety of shapes. The shape may be substantially symmetrical to the shape of the toilet, which is an oval or tear drop shape. The shape may be any type of rounded shape, for example having at least one cross section that is oval or circular. Other shapes for the modules may include square, rectangular, or circular. The module be shaped in order to fit in a particular direction or orientation with the lid 122. That is, the module may be asymmetrical. The module may include a bulkhead 114 that aligns with a portion of the lid 122 and guides the fit between the toilet and the module. The bulkhead 114 may refer to a frame for the module or a particular supporting member with the frame for aligning the module to the lid 122. The bulkhead 114 may have a shape corresponding to an opening of the toilet seat 121. The bulkhead supports the plume cleaner assembly.

The module dock 111 may include a snap fit connection with the modules and/or the modules may form snap fit connection with each other. The module dock 111 may include a depression configured to mate with a protrusion on the top of a module. The protrusion of the module may include a hook or stud that fits inside the depression. The hook or stud may be depressed (e.g., bended, biased) in order to align with the depression, which secures the connection and prevents the hook or stud from being easily removed from the depression. So that modules can be stacked, the bottom of the module may also include such a depression. Alternatives to a snap fit connection for the module dock 111 may include fasteners (e.g., screws or bolts), latches, clips or other hardware. The hardware for these connection devices may be formed of plastic or another rust resistant material.

The toilet seat 102 is connected to the lid 122 via hinge. The hinge includes a pin that fits through one or more knuckles of the toilet seat 121 and the lid 122 so that the toilet seat 121 may be rotated with respect to the lid 122. In one example, one or more of the modules include at least one knuckle or other hollow circular portion through which the pin can pass. In this way, the module may be installed to be independently rotatably connected to the lid 122 and to the toilet seat 121. In one example, the module is connected both by the hinge and the module dock 111.

The module dock 111 may also include an electrical connection or mechanical switch that indicates to the controller 12 the identity of the module. That is, the controller 12 may receive information on the type of module that has been connected to the module dock 111. In one example, the module dock 111 may include a set of mechanical switches in predetermined locations. In another example, the module dock 111 may include a set of electrical contracts in predetermined locations. One switch or contact is located in a position that lines up only with the impactor module 200, another switch or contact aligns with the electrostatic module 300, another switch or contact aligns with the hydroxyl module, and another switch or contact aligns with the multi-cyclone module 500. When a module is installed, the controller 12 receives a signal in response to the switch or contact and selects one or more commands or algorithms in response to the connected module.

In addition, to the tank 108, the rear housing may include at least one fan 110 and at least one corresponding vent 113. The fan 110 positioned to draw plume air through the plurality of apertures for treatment by the plume cleaner and expel the treated plume air out of the plume cleaner assembly in a direction at an angle to the longitudinal axes of the plurality of apertures. The fan 110 may draw the plume air through a serpentine plume path through the plume cleaner assembly between the toilet and the toilet seat cover or between the toilet and the toilet seat. The serpentine plume path is configured to receive plume air from the toilet and guide the plume air through multiple turns. As discussed in more detail in other embodiments, a light source may be configured to irradiate the plume air of the serpentine plume path.

The module dock 111 that coupled to the toilet seat cover and configured to removably attach one or more modules to the toilet seat cover. The modules may include any combination of an impactor module 200, an electrostatic module 300, a hydroxyl module 400, and a multi-cyclone module 500. The modules may be attached to the module dock 111 individually and interchangeably. Two or more modules may be attached to the module dock (e.g., in another shape not illustrated) or two or more modules may be stacked.

Each of the modules may include multiple channels for the air path. The modules may at least one radial channel configured to direct the plume air from the toilet bowl to apertures on the entry into an output channel configured to direct the treated plume air to the fan 110.

Each of the modules may include a light source or be positioned near a light source mounded on the lid 122. Thus, the plume cleaner assembly is positioned adjacent to the lid 122 and may include a cavity configured to receive the light source that is mounted to the lid 122. The plume cleaner assembly adjacent to the toilet seat cover includes a transparent portion to provide a light path from the light source to the at least one radial channel.

Figure 3A:
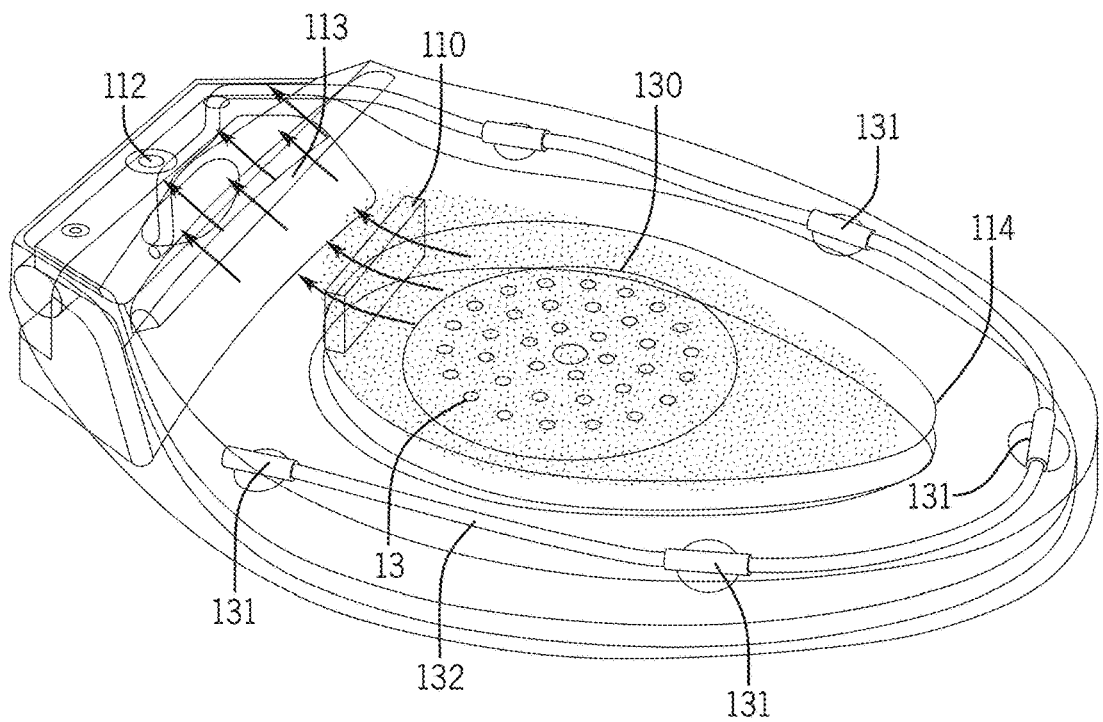
FIGS. 3A and 3B illustrate an air flow path through the sanitization system.
Figure 3B:
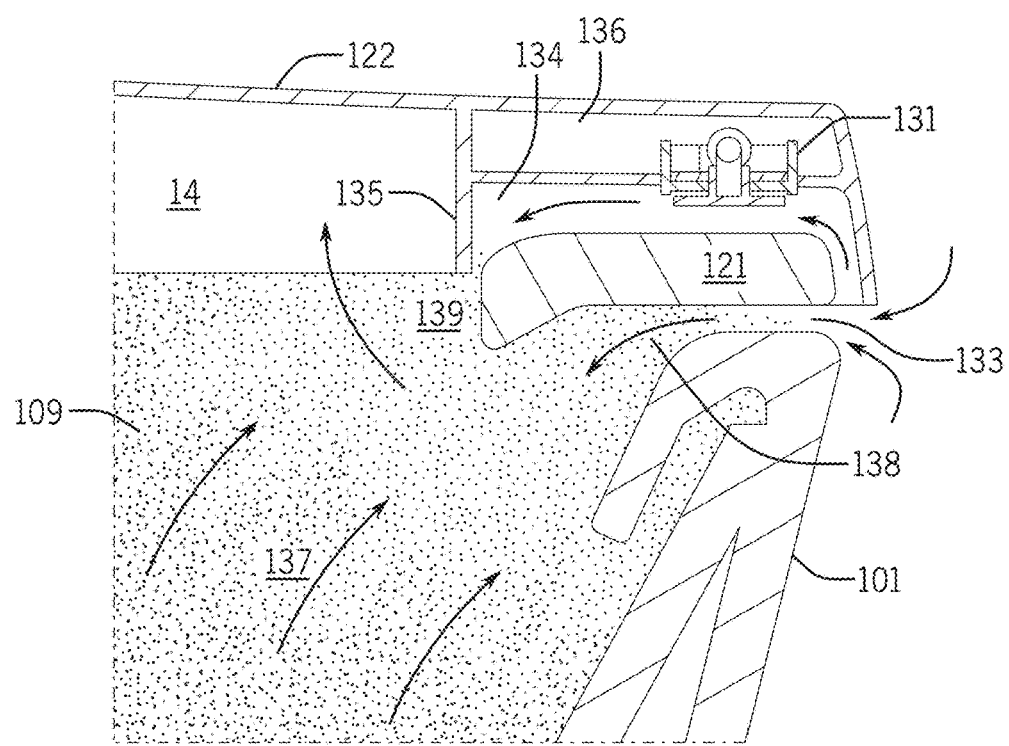

FIGS. 3A and 3B illustrate an air flow path through the sanitization system including a module 130 or combination of modules. The module 130 illustrated includes a catalyst reactor adjacent to air flow paths. The air flow path may draw air from the toilet bowl 101 that originates in a variety of locations. Some air may travel into the toilet bowl 101 from the internal channels of the toilet 100 such as the rim channels between the toilet bowl 101 and the tank 103. Some of the air may travel from the environment of the toilet. The air flow path passes through the toilet bowl 101 and passes through the plume cleaning assembly via a network of apertures 13. The fan 110 draws the air from the apertures 13 toward the vent 113.

FIG. 3B illustrates a negative pressure region that is generated around the toilet seat 121 and/or between the lid 122 and the toilet seat 121. The negative air pressure indicates that the flow of air is from outside of the toilet bowl 101 to the inside of the toilet bowl 101. The negative air pressure is maintained by pulling air by the fan 110 out of the toilet bowl 101 toward the vent 113.

The flow of air around the toilet seat 121 may include an upper path and a lower path. The flow of air may extend from outside of the bowl 101 through opening 133 to the upper path at misting cavity 134 over the toilet seat 121 and through opening 135 to the interior of the toilet bowl 101 at a low pressure region 139. The flow of air may extend from outside of the bowl 101 through the opening 133 then under the toilet seat 121 as shown by arrow 138.

Thus, even if a toilet plume is on a trajectory (e.g., shown by arrow 137) that would normally escape the toilet bowl 101 and/or deposit particles on the toilet seat 102, the negative air pressure prevents the trajectory from escaping the toilet bowl 101 or reaching any surfaces that the user may come in contact with.

The lid 122 may define several compartments or spaces that are partially enclosed or substantially enclosed. The lid 122 may include a module space 14 for the module. The module space 14 may extend below at least a portion of the toilet seat 102. For example, the module space 14 extends below the top of the toilet seat 102 near opening 135. The lid 122 may include an enclosed space, fluid distribution system cavity 136, for the misting system, which is discussed in more detail herein. The lid 122 may include a partially enclosed seat space, or misting cavity 134. Within the misting cavity 134 a pressure is maintained so that air is flowing from outside of the toilet bowl 101 to inside of the toilet bowl 101. The flow of air may be very close to zero. Stated another way, the pressure in misting cavity 134 prevents the reverse flow of air out of the toilet bowl 101.

The cavities may be defined according to the relative position of the toilet seat 121 and the bowl 101. The space between the bowl 101 and the toilet seat 121 where the module or plume cleaning assembly is located when the toilet seat 121 is in the lowered position is a plume cleaning space including multiple cavities. The lid 122 may further define fluid distribution system cavity 136 and the misting cavity 134, and the toilet seat 121 at least partially encloses the misting cavity 134 in the lowered position. The module space 14 may also be a plume cleaning cavity aligned with the bowl and filled with the mist from at least one atomizer configured to generate a negative relative air pressure in the misting cavity, wherein the negative relative air pressure prevents airflow into the misting cavity from the plume cleaning cavity or an ambient environment.

Figure 4A:
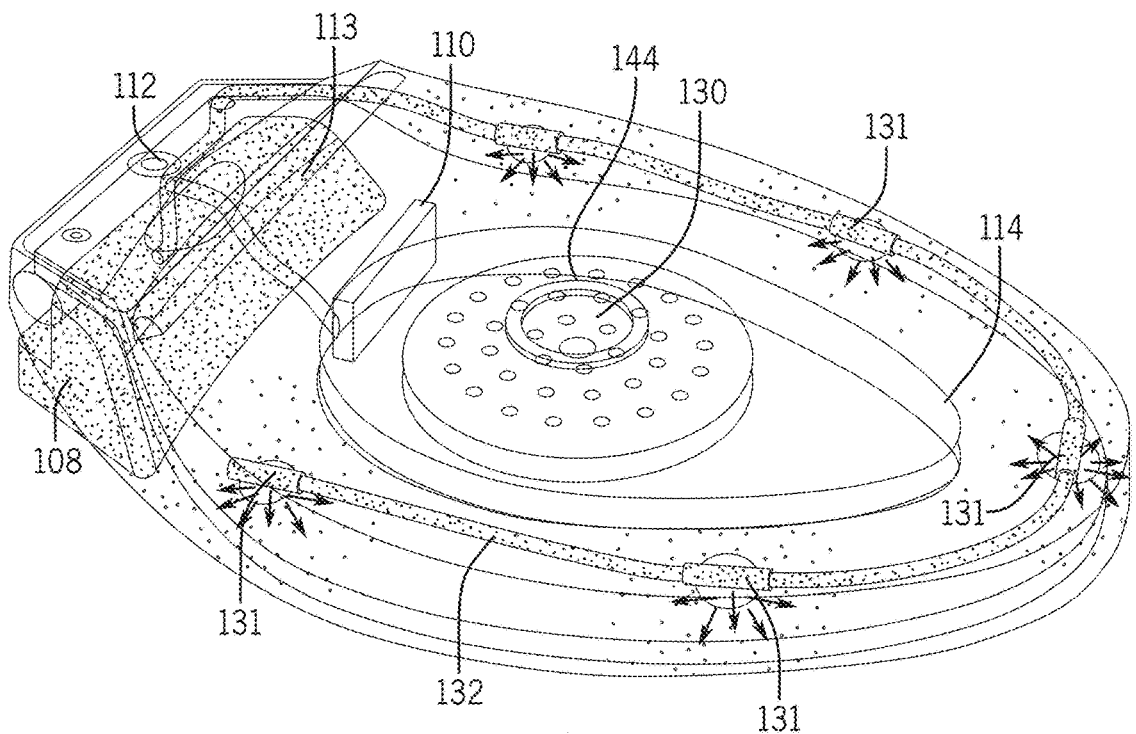
FIGS. 4A and 4B illustrate a liquid path through the sanitization system.
Figure 4B:
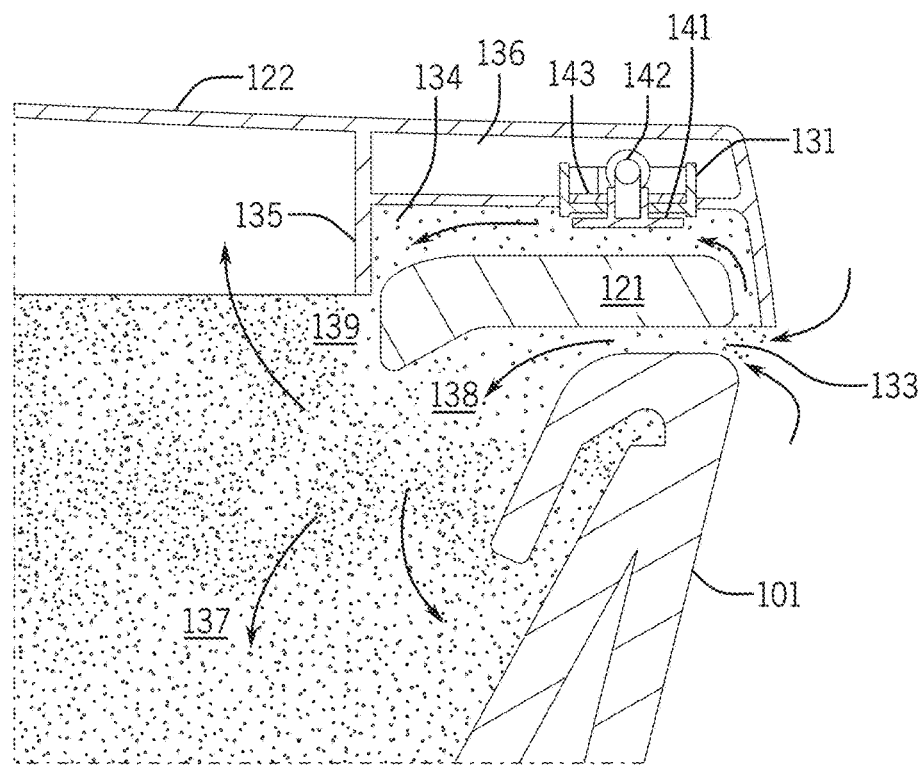

FIGS. 4A and 4B illustrate a liquid path through the sanitization system. The path may originate at tank 108 and extend through feed line 132 to a plurality of misters 131. The feed line 132 may extend through the space 136. The feed line 132 may be supported by one or more brackets in the space 136. A pump 149 (illustrated in FIG. 5) may pump the liquid from the tank 108 through the feed line 132. The pump 149 may be electrical having one or more moving parts driven by a motor. The moving part may be an impeller, piston and diaphragm, vane or other component.

The compartmentalization of the lid helps manage air flow above the seat surfaces, isolating them so that they get the greatest concentration of chemistry. The air flow helps retain the chemistry inside the lid, helping to dry the surfaces while directing the mist into the bowl.

The particles of the plume occur at various sizes, and the modules above may be designed to control the flow and sanitization of these particles. The misters 131, however, allow the plume to be controlled so that particles off the plume adhere to the mist. The mist can be controlled. The mist can be controlled in timing, in volume, and in particle size.

For particle size, the misters 131 may be configured to generate mist particles have a specific size (e.g., less than 40 microns, or between 10 and 20 microns). The mist may be a dry fog that does not wet the surfaces of the toilet or make the surfaces feel wet or damp. The smaller particles tend to repel each other because of a weak electrostatic charge on the surfaces. Instead, the smaller particles may coalesce into larger droplets and remain suspended in the air.

Examples from the mister 131 may include the atomizer illustrated in FIG. 4B. The mister 131 includes a horn 141, a mister body 142, a piezoelectric element 143. The mister body 142 is configured to receive a flow of liquid and meter the flow of liquid.

The flow of liquid may be received locally from the tank 108 as a solution reservoir configured to deliver a solution to the at least one atomizer. The horn 141 is configured to receive the metered liquid from the horn and a predetermined vibration to create standing waves that cause the metered liquid to atomize and exit the horn. The horn 141 may cause cavitation inside the individual drops of metered liquid. The piezoelectric element 143 or crystal is configured to convert an electrical signal to the predetermined vibration.

The ultrasonic horn may include a tip with a shape of the tip that determines the spray. The tip could be shaped to provide a 180 degree spray in one example and a 45 degree spray in another example. The tip may be configurable. The spray may be selected depending on the position of a particular mister, the model of toilet, or a user selection.

The horn 141 may be oriented differently to create different atomization patterns. Depending how the inside of the horn 141 is coated by the metered liquid, different patterns in the mist may be produced.

In addition, the horn 141 may be oriented downward in a way that efficiently uses the metered liquid. For example, the solution in the tank 108 may be in limited supply, or at least, it may be desirable for the solution to last for a long period of time. To reduce the amount of solution that is used, a single drop may be provided by the pump to the horn 141. The drop held in surface tension off the surface of the horn 141 to cause the cavitation to occur. The horn 141 produces mist from the single drop until the drop is depleted.

Another example of the mister 131 may include an interdigital transducer configured to generate a surface acoustic wave that causes liquid to mist and exit the atomizer. A power circuit is configured to provide a radio frequency signal to the surface acoustic wave and a driving circuit configured to control an actuating device to meter a flow of liquid into the atomizer.

Another example of the mister 131 may include a misting wand configured to provide a mist in a configurable predetermined direction.

The controller 12 is configured to control the mister 131. A programming logic controller (PLC) may set a driving interval and driving frequency to the piezoelectric element 143. The PLC may also set a maximum voltage or maximum power provided to the piezoelectric element 143.

As an initial example that may be combined with any of these examples, the controller 12 may include a timer. The sanitization system may be activated at a specific time interval (e.g., once an hour, every four hours, or once a day). The user may select the specific time interview.

Any or all parts of the sanitization system, including the mister 131, the fan 110, and/or any of the module may be activated or deactivated by the controller 12 according to the operation of the toilet. The sensor 11 may detect whether the toilet seat assembly 102 is open or closed. The sensor 11 may detect the operation of the toilet. The sensor 11 may detect ambient conditions.

The sensor 11 may detect whether the toilet seat assembly 102 is open or closed using an optical sensor that detects whether the module is facing the inside of the toilet bowl 101 or the water. The sensor 11 may detect whether the toilet seat assembly 102 is open or closed using a tilt sensor or inertial sensor. The sensor 11 may detect whether the toilet seat assembly 102 is open or closed using a mechanical switch that is depressed when the toilet seat assembly 102 is down. Magnetic, gravity, or other types of sensors may be used. The controller 12 may prevent the sanitization system from being activated when the toilet seat assembly 102 is up, or otherwise, trigger the sanitization system when the toilet seat assembly has been placed down.

The controller 12 may elect a cleaning sequences based on data from the sensor 11. For example, a weight sensor in the seat may provide based on the user or type of use. A deep clean may be provided after some usages and a quick clean provided after other usages.

Figure 5:
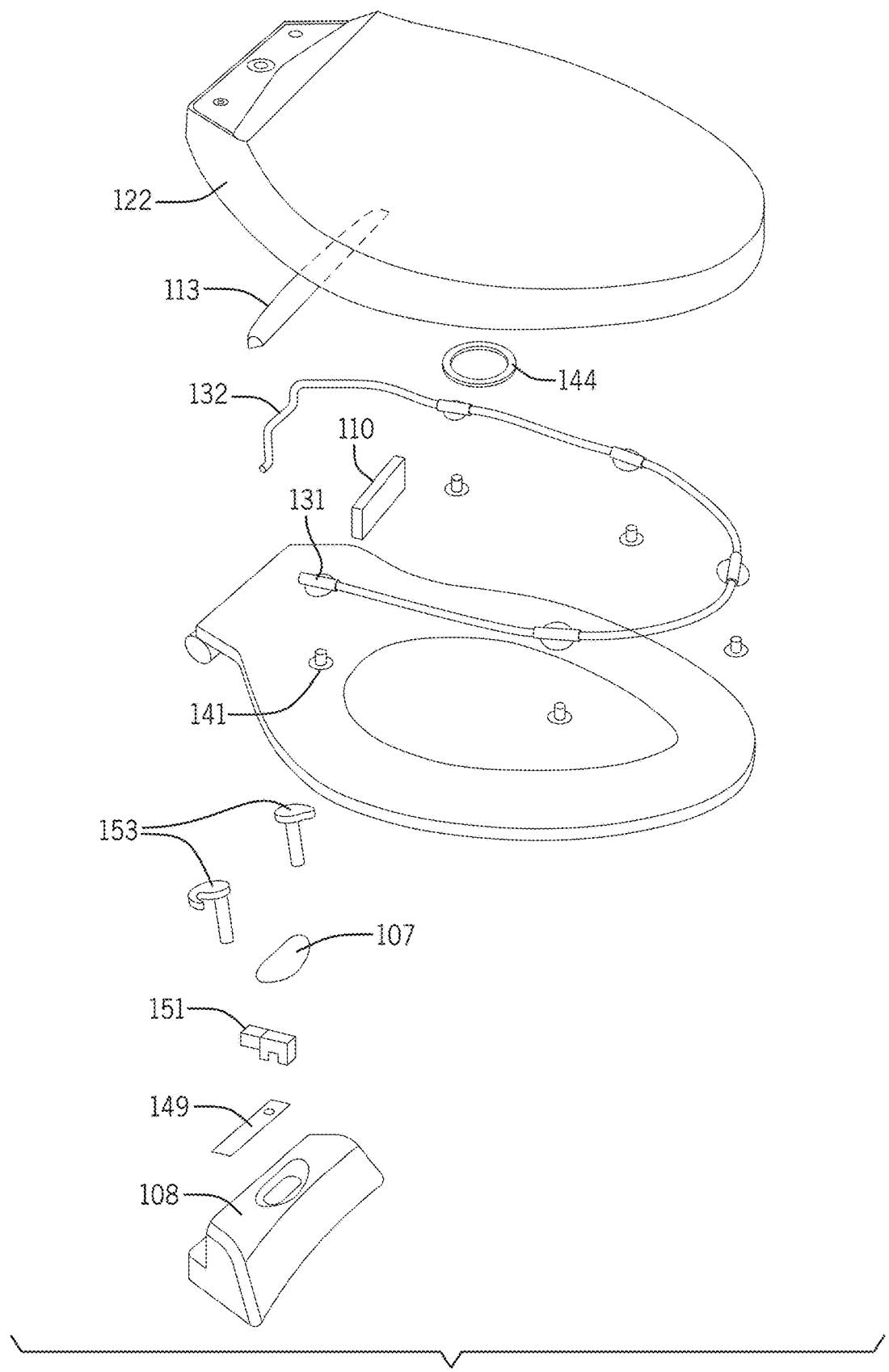
FIG. 5 illustrates an exploded view of the misting system for the toilet seat.

FIG. 5 illustrates an exploded view of the sanitization system in FIGS. 3A-B and 4A-B, including air flow and misting for the toilet seat as described previously. Additional components may include one or more cam locks 153 for securing the toilet seat and sanitization system to the toilet.

Figure 6A:
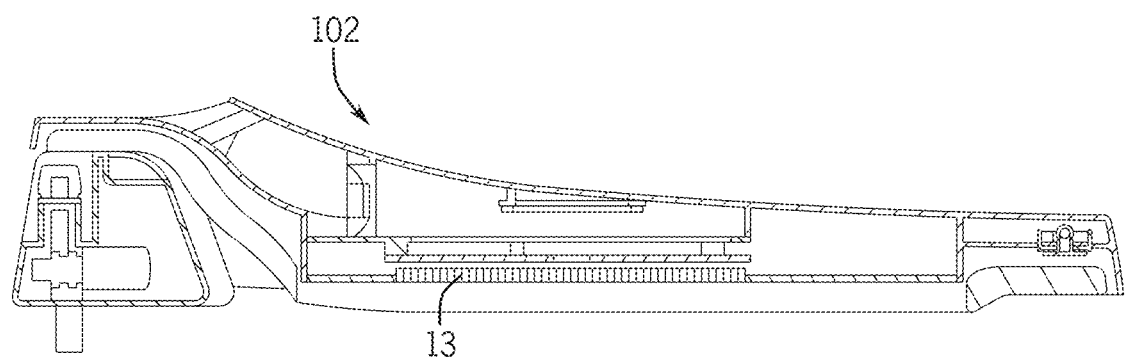
FIGS. 6A and 6B illustrate an example impactor module for the sanitization system.
Figure 6B:
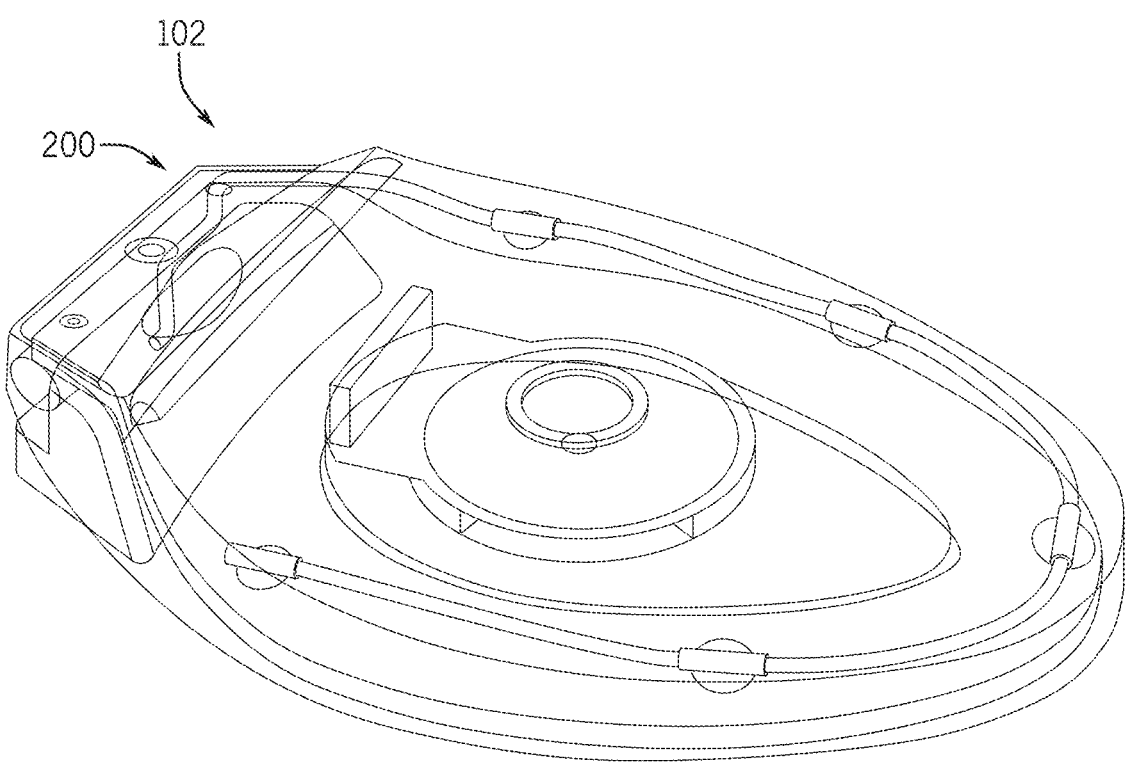
Figure 7A:
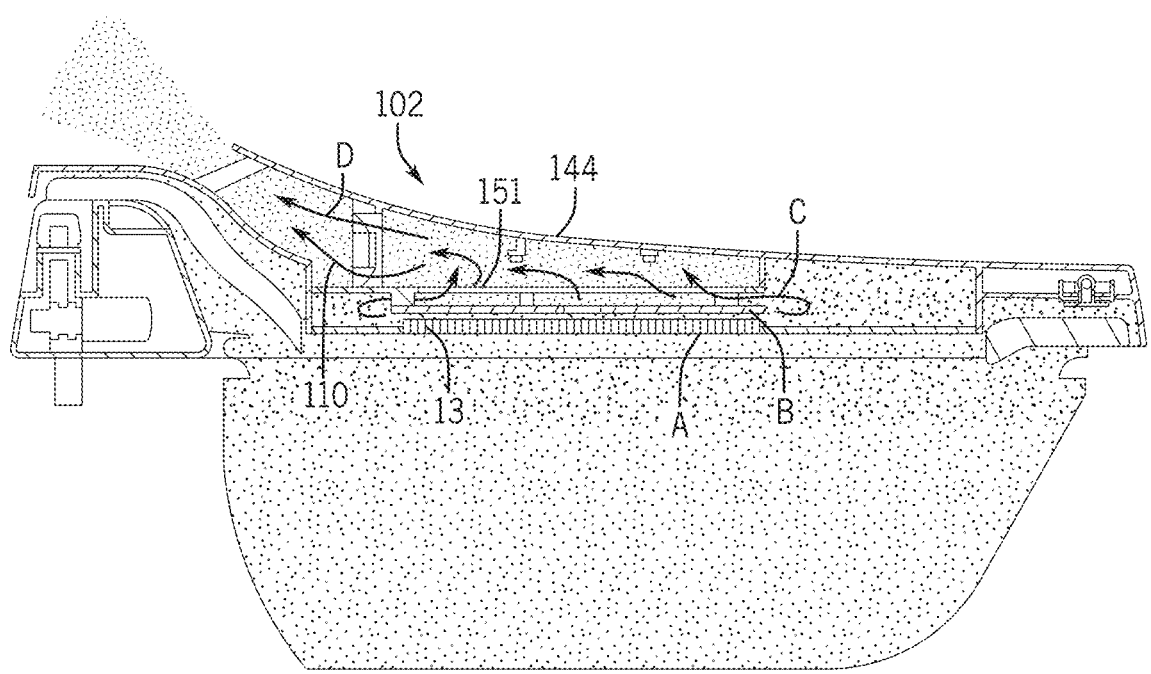
FIGS. 7A and 7B illustrate an example impactor module for the sanitization system.
Figure 7B:
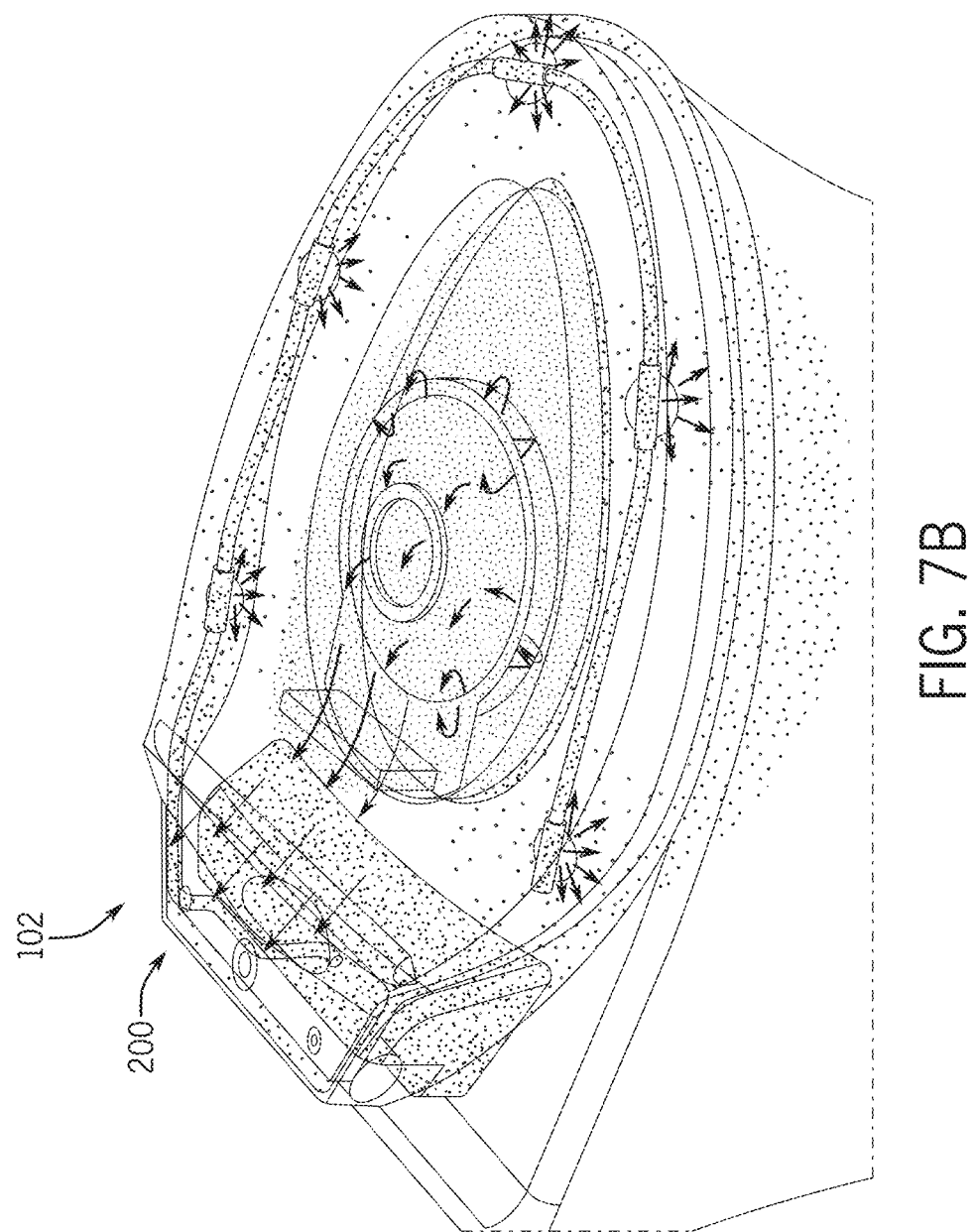
Figure 9A:
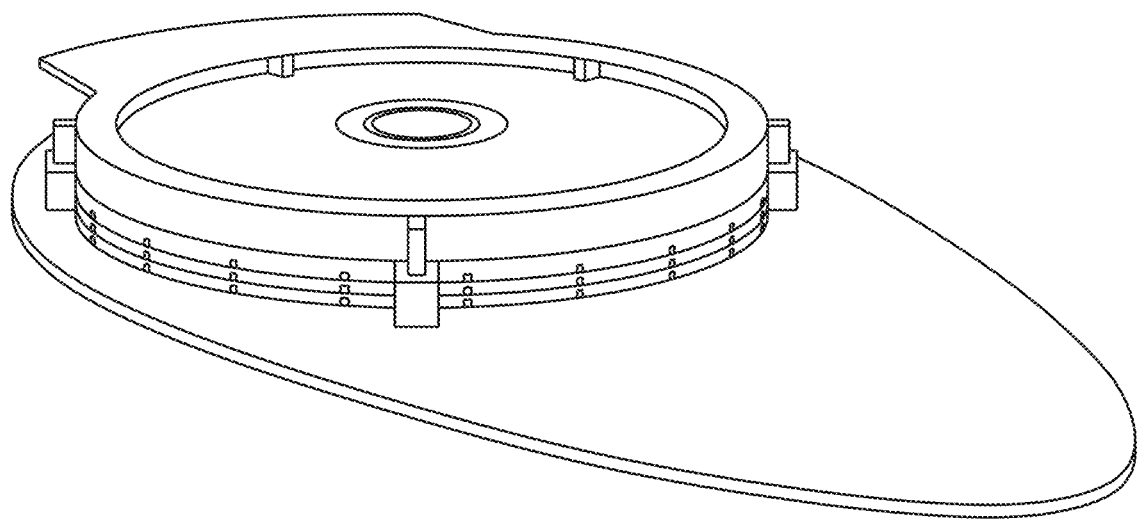
Figure 9B:
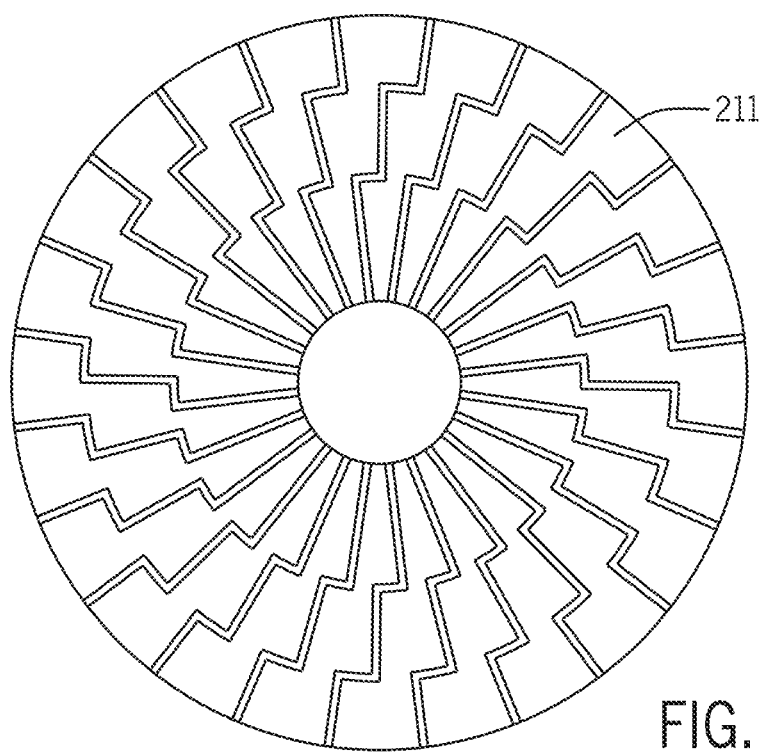

FIGS. 6A and 6B illustrate an example impactor module for the sanitization system. FIGS. 7A and 7B illustrate an example impactor module 200 for the sanitization system. The impactor module 200 may include an impactor plate 151 and apertures 13. Additional, different, or fewer components may be included.

As air is channeled through the apertures 13, the air is accelerated. The air may be accelerated because the spatial volume of the air is lower in the apertures 13 than before the apertures 13. The accelerated air collides with the impactor plate 151. The collision causes any (e.g., a substantial portion thereof) suspended particles (e.g., aerosols, viruses, bacteria, or contaminants) to be deposited on the impactor plate 151. The light source 144 irradiates the impactor plate 151 and sanitizes or eliminates the deposited particles.

The impactor plate 151 stops or slows particles in the toilet plume so that the particles spend more time in the irradiation light of light source 144. Another, technique used to increase the time spent in the irradiation light of light source 144 is a serpentine path for the air flow.

A serpentine plume path may be defined as a path that changes direction at least two time. A serpentine path does not take the shorted path between two points but rather increases the path so as the increase the time the particles are in the irradiation light of light source 144. The plume assembly between the toilet 100 and the toilet seat cover 122 or between the toilet 100 and the toilet seat 121 includes the serpentine plume path to receive plume air from the toilet and guide the plume air through a plurality of turns.

One example serpentine path extends through vertical channels, as shown by arrow A, toward the impactor plate 151. Then the impact with the impactor plate 151 causes the air flow to turn to move radially (horizontal direction), as shown by arrow B. Then the path travels around the impactor plate 151, as the air is drawn by fan 110. Finally, the serpentine path extends to the vent, as shown by arrow D. The serpentine plume path includes a first portion in a first direction (e.g., arrow B) and a second portion in a second direction (e.g., arrow C). The first portion and the second portion share a wall (e.g., the impactor plate 151).

FIGS. 8A, 8B, 9A, and 9B illustrate another example impactor 220 for the sanitization system. In one example, the impactor 220 may include a plurality of discs 210 (e.g., FIG. 8B illustrates a stack of discs 210a, 210b, and 210c). In some examples, the impactor 220 includes a light source and in other examples the light source is omitted.

Each disc may include a plurality of channels or apertures. The air flow may flow through one of the discs then be forced through a horizontal path to the channels of the next disc. In this way, the series of discs create a serpentine path. The air may be forced vertically through one disc, then horizontally between discs.

The impactor 220 may include dividers 212 within discs or between discs that divide spaces with the impactor 220 into chambers 211. The chambers 211 may have a variety of shapes. The dividers 212 divide the air path so that air flowing up through a disc is forced into another direction. The serpentine plume path includes a first path portion that is substantially vertical path toward a horizontal obstacle provided by the disc 210 and a second path portion that is substantially horizontal and parallel to the horizontal obstacle provided by a vertical obstacle such as the divider 212.

The dividers 212 may have spaces in the radial direction that allows flow of air between chambers 211. Thus, the serpentine plume path may include a third path portion around the horizontal obstacle and a forth path portion away from the horizontal obstacle.

The chambers 211 may be connected by openings that are arranged to create a series of chambers 211 with staggered apertures between the series of chambers 211. For example, rather than all adjacent chambers including openings, only certain chambers 211 are connected to provide a particular serpentine path through the discs.

An additional example embodiments for the serpentine path may include rounded or coiled paths. A coiled path provides a circular path for the serpentine path.

An additional example embodiments for the serpentine path may include one or more valves between chambers 211 in order to slow the flow of air. The valves may be a porous material such as foam. The valves may further increase the time that air spends in the serpentine path and in the path of irradiating light.

Figure 10A:
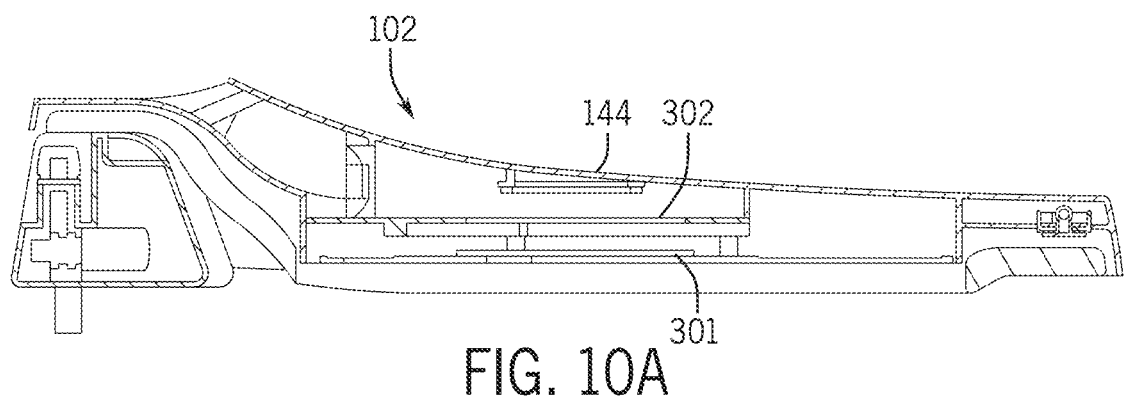
FIGS. 10A and 10B illustrate an example charging module for the sanitization system.
Figure 10B:
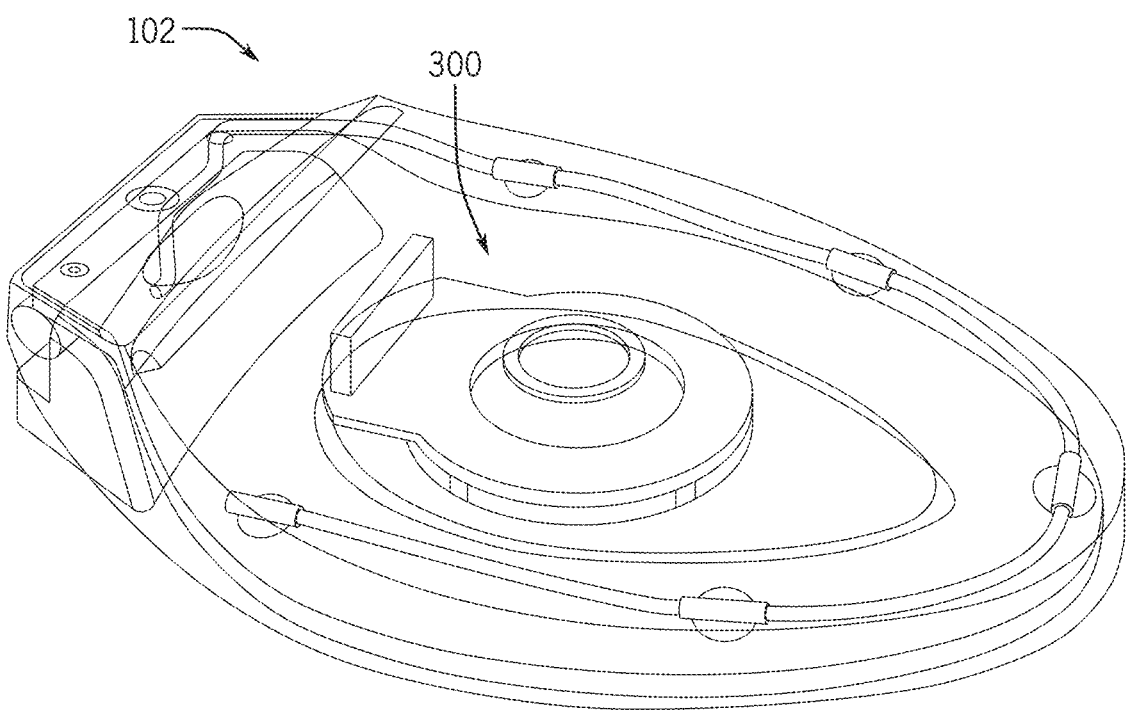
Figure 11A:
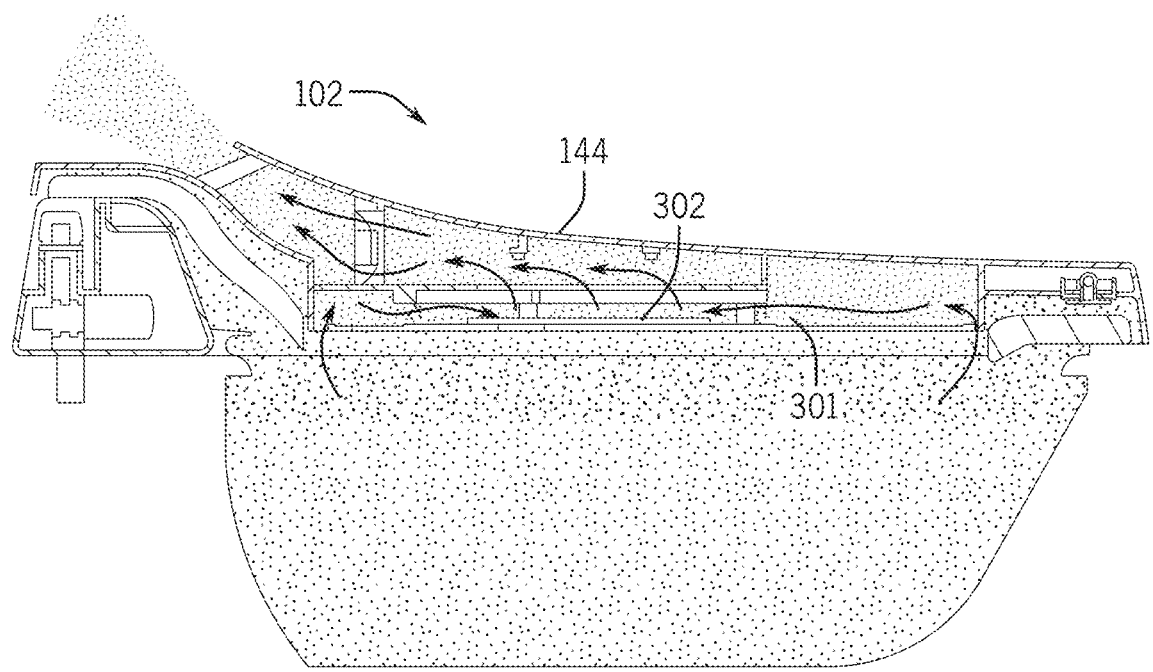
FIGS. 11A and 11B illustrate an example charging module for the sanitization system.
Figure 11B:
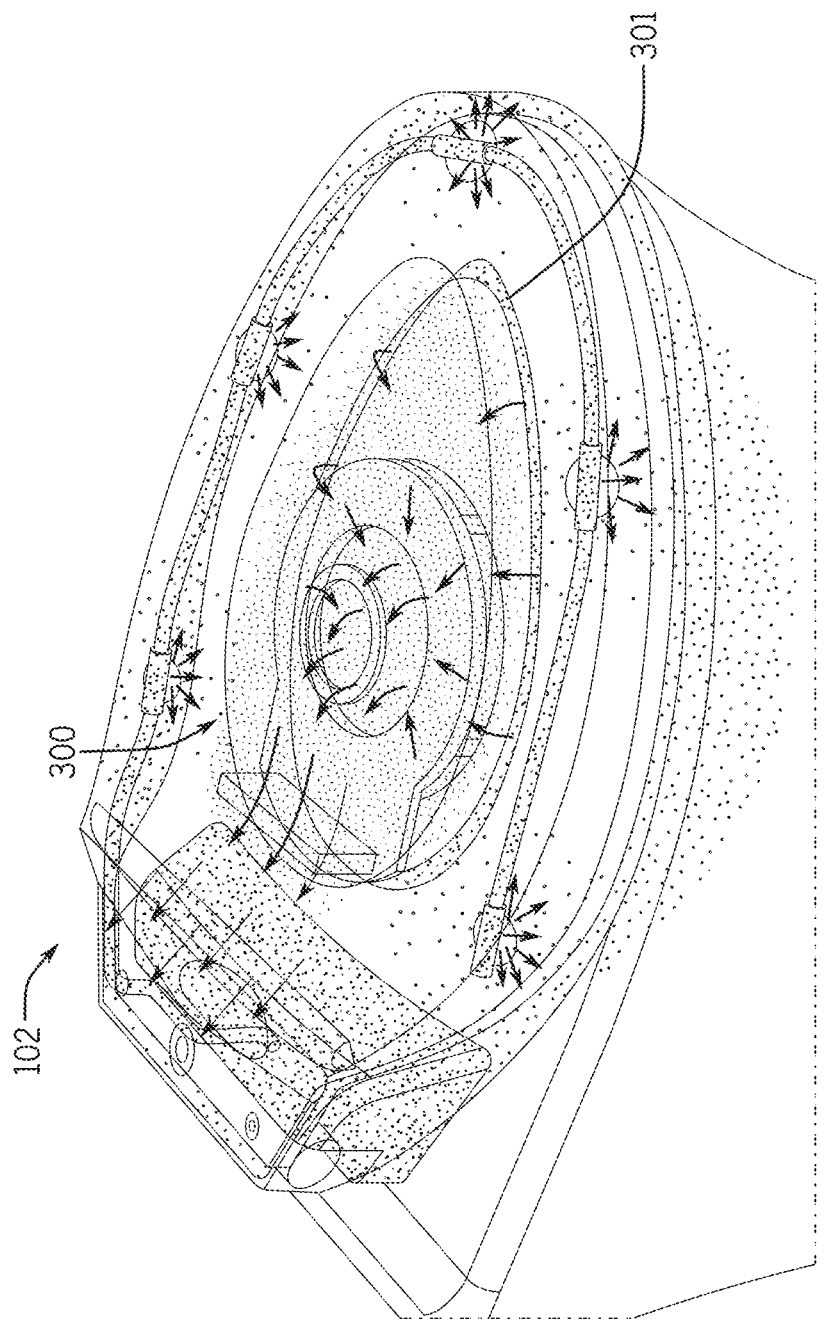

FIGS. 10A and 10B illustrate an example charging module 300 for the sanitization system. FIGS. 11A and 11B illustrate an example charging module 300 for the sanitization system. The charging module 300 may include a charger 301 and a collection plate 302. In some examples, the charging module 300 charges the plume air naturally expelled from the toilet 100. In some examples, the charging module 300 charges the mist from the misting system that is merged with the plume air.

As air/mist is pulled from the bowl 101 through the sanitization system by the fan 110. The air/mist initially passes over a charger 301. The charger 301 may include a device that imparts an electrostatic charge on the particles within the plume. The charger 301 ionizes the air around the plume or within the plume using a high voltage that causes the air to breakdown and become conductive. The corona occurs when the potential gradient of the electric field around the charger 301 is greater than the dielectric strength of the air or the plume.

The charger 301 may be a corona wire with a small diameter wire (e.g., less than 100 microns). FIG. 11B illustrates that the corona wire 301 travels along the perimeter of the charging module 300 (e.g., in an oval or teardrop shape). The corona wire may be an example of a two conductor charger. The charger 301 may include a brush. The brush may an example of a single conductor charger.

The charger 301 may include a capacitance plate (i.e., the corona wire may be omitted). The capacitance plate may be formed from a conductive sheet bonded to a dielectric material. The conductive sheet may be foil. The dielectric material may be plastic. A control bias may be selectively applied to the conductive sheet. For example, a power source may be connected to the conductive sheet and turned on and off by the controller 12. The controller 12 may apply a high voltage to the conductive sheet in periodic time intervals or in response to the flush cycle.

In some examples, the misting system that generates the mist or dry fog sets one or parameters of the mist in order to facilitate the corona charging. For example, the misting system may set a particle diameter for the mist (e.g., 10, 20, 50 or 100 microns). The particle size may be a maximum particle size or an average particle size. The misting system may impart a charge to the mist. While the small fog/mist particles may already have a charge, the charger 301 also imparts a charge onto any dust or microbes present as well. The charger 301 may impart a particular polarity (e.g., negative) on the mist.

The negatively charged particles may then be drawn toward the collection surface, which is positively charged.

The surface may be positively charged through adsorption of ions or another technique. The collection surface is within an internal chamber in the sanitization system and bathed in light (e.g., ultraviolet) from the light source 144. The light acts to directly disinfect the particles drawn toward the positively charged collection plate 302.

As discussed in more detail, the charger 300 may also include a photo-catalyst applied to the collection surface. The light source 144 may also activate the photo-catalyst to enhance the effectiveness of the disinfection system. The light source 144 may simultaneously activate the photo-catalyst and disinfect the particles attracted to the collection plate 302.

In addition, the collection plate 302 may be self-cleaning and may be easily removed for maintenance or cleaning. The collection plate 302 may be attached to the charging module 300 with a clip or other quick connection.

Figure 12A:
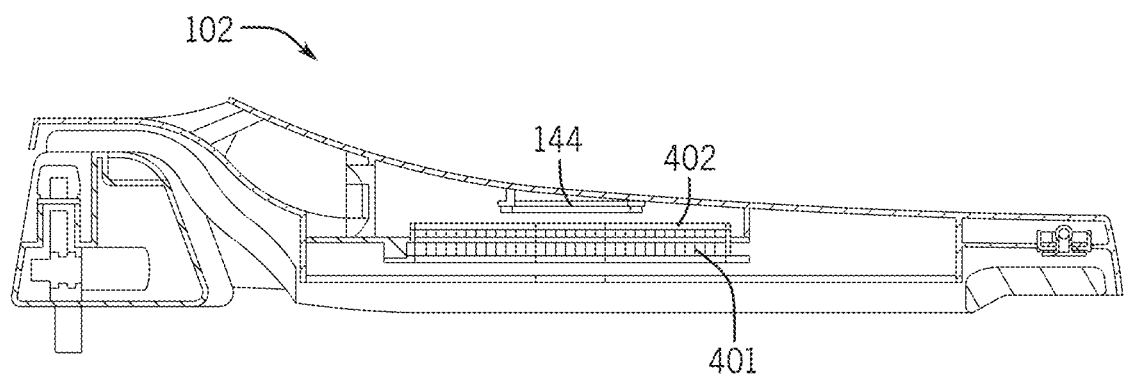
FIGS. 12A and 12B illustrate an example hydroxyl module for the sanitization system.
Figure 12B:
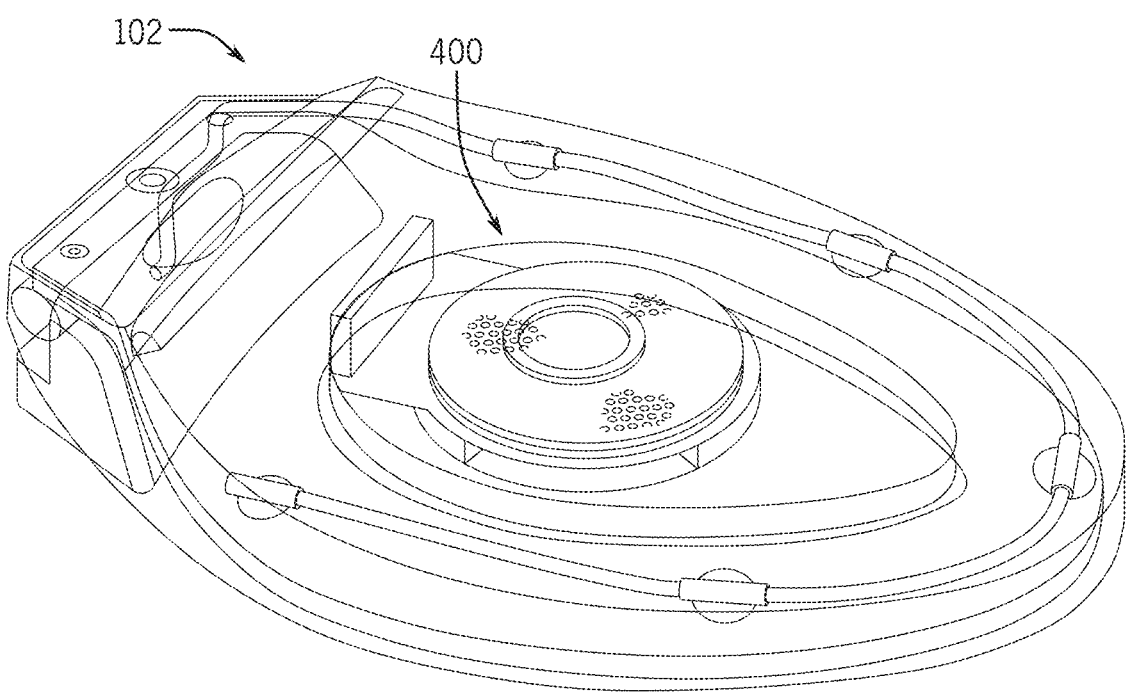
Figure 13A:
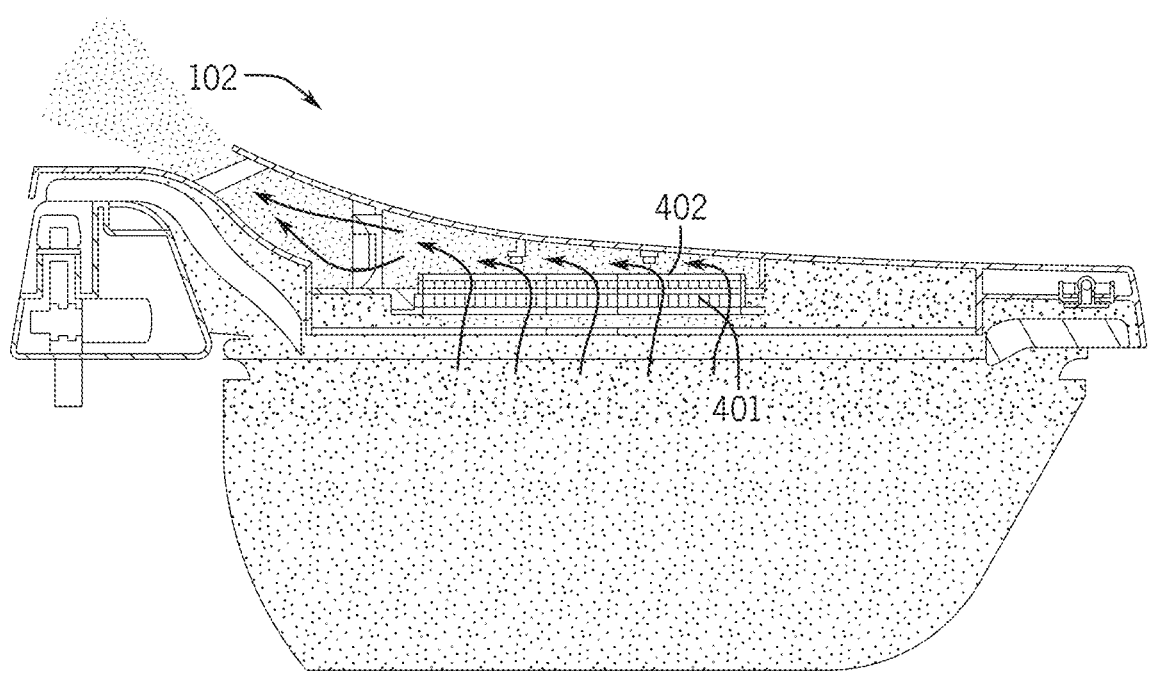
FIGS. 13A and 13B illustrate an example hydroxyl module for the sanitization system.
Figure 13B:
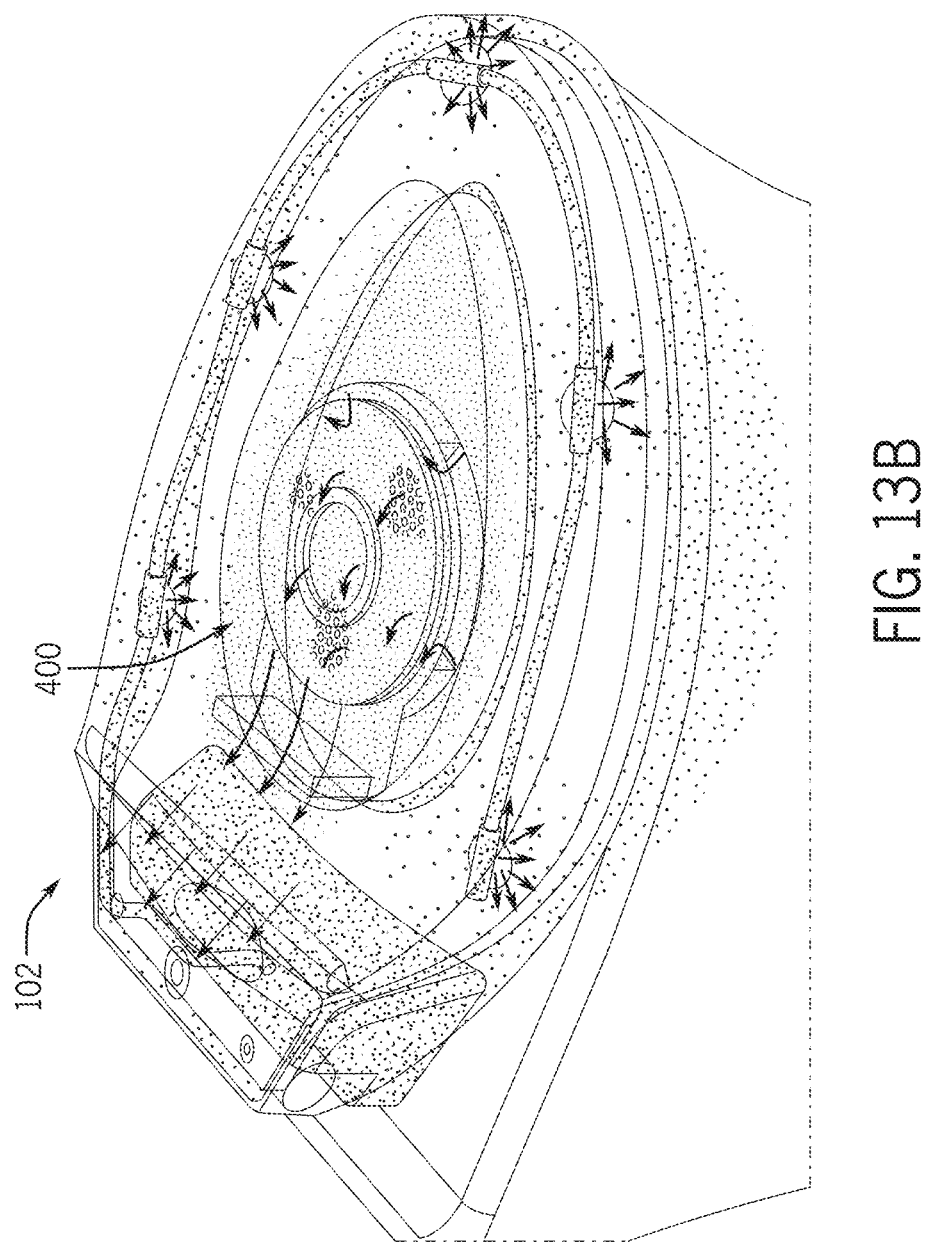

FIGS. 12A and 12B illustrate an example hydroxyl module 400 for the sanitization system. FIGS. 13A and 13B illustrate an example hydroxyl module 400 for the sanitization system. The hydroxyl module 400 may include a base structure 402 for a photocatalytic filter including multiple cells 401. Additional, different, or fewer components may be included.

The cells 401 of the photocatalytic filter may have a variety of shapes. The cells 401 may be spherical such as beads. The cells 401 may be honeycomb shape (e.g., hexagonal prism).

The base structure 402 may be a reactor chamber that encloses the cells 401. The base structure 402 may be shaped as a container (e.g., cage) where the cells 401 are loosely housed and may move around with the base structure 401. The base structure 402 may securely mount the cells 401 (e.g., honeycomb structure).

The cells 401 may be hollow so that the air flow passes through the cells 401. In this cases the air flow is forced to be within a predetermined distance of the surface of the cell 401. The size of the passage through the cells 401 may selected to be small enough to initiate sufficient reaction with the catalyst. However, the size of the passage through the cells 401 may selected to be large enough to prevent substantial back pressure on the fan 110.

The cells 401 may be formed of glass or another material with a surface that can be applied with a catalyst. The catalyst may include the anatase form of titanium dioxide applied as a coating to the cells 401.

The light source 144 may irradiate the cells 401 to activate the catalyst on the cells 401. The catalyst acts in response to proximity of particles with the cells 401. As the plume is released from the toilet 100, some particles of the plume pass within a predetermined distance to the cells 401, causing a reaction with the catalyst. The reaction may produce hydroxyls or peroxides. The reaction may break down anything adhered to the particles in the plume. Viruses or bacterial may be killed or eliminated by the reaction. In addition, volatile compounds associated with smells may be broken down by the reaction.

The hydroxyl module 400 may also cause a reaction with the mist from the misting system. The particles from the mist may be adhered to particles from within the toilet 100 or from the plume. When the mist flows into the cells 401, or near the cells 401, the hydroxyl module 400 cause a reaction to take place with these particles.

Figure 14A:
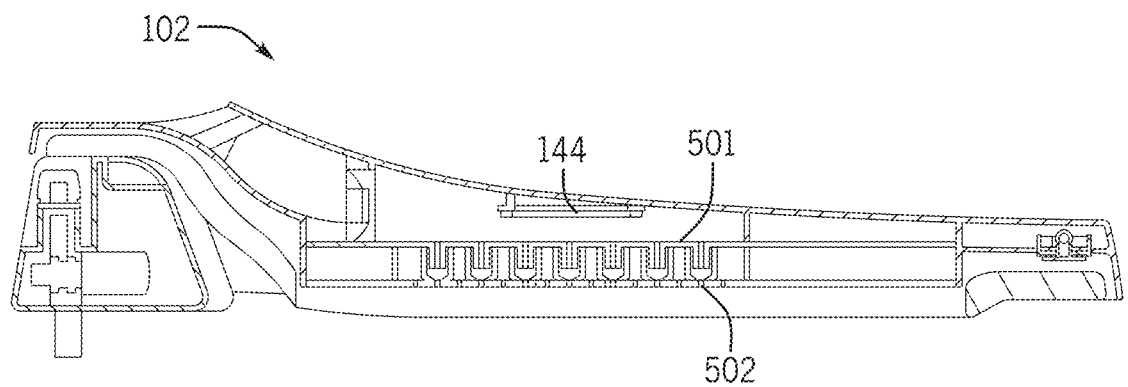
FIGS. 14A and 14B illustrate an example cyclone module for the sanitization system.
Figure 14B:
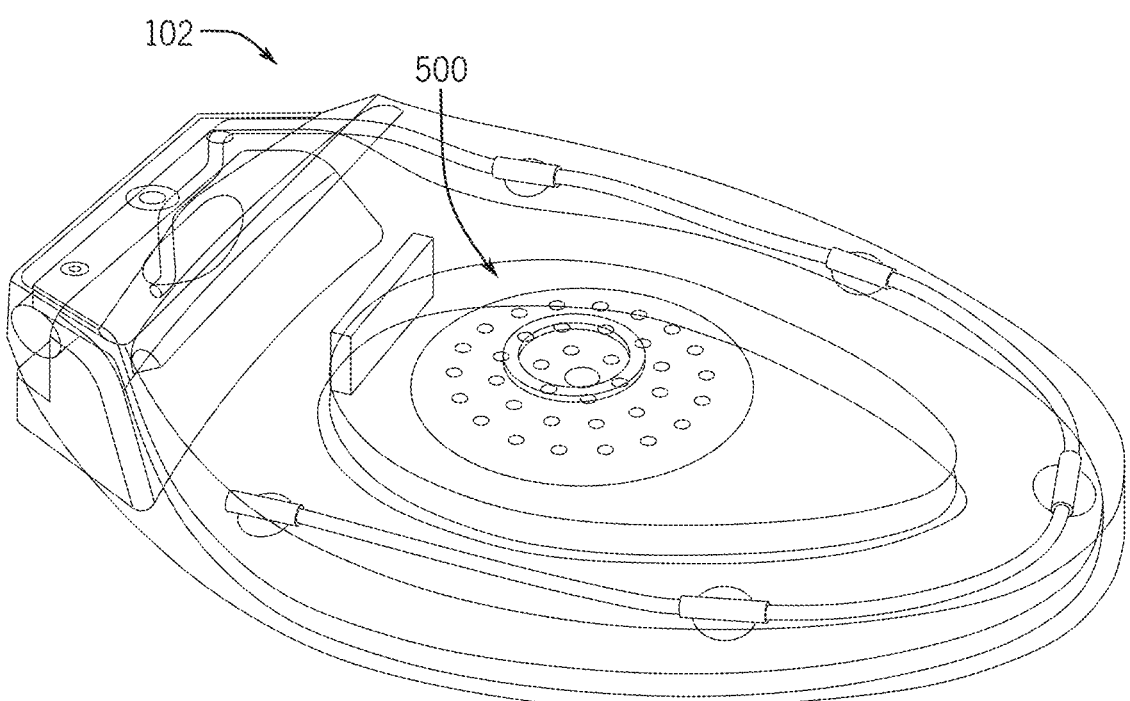
Figure 15A:
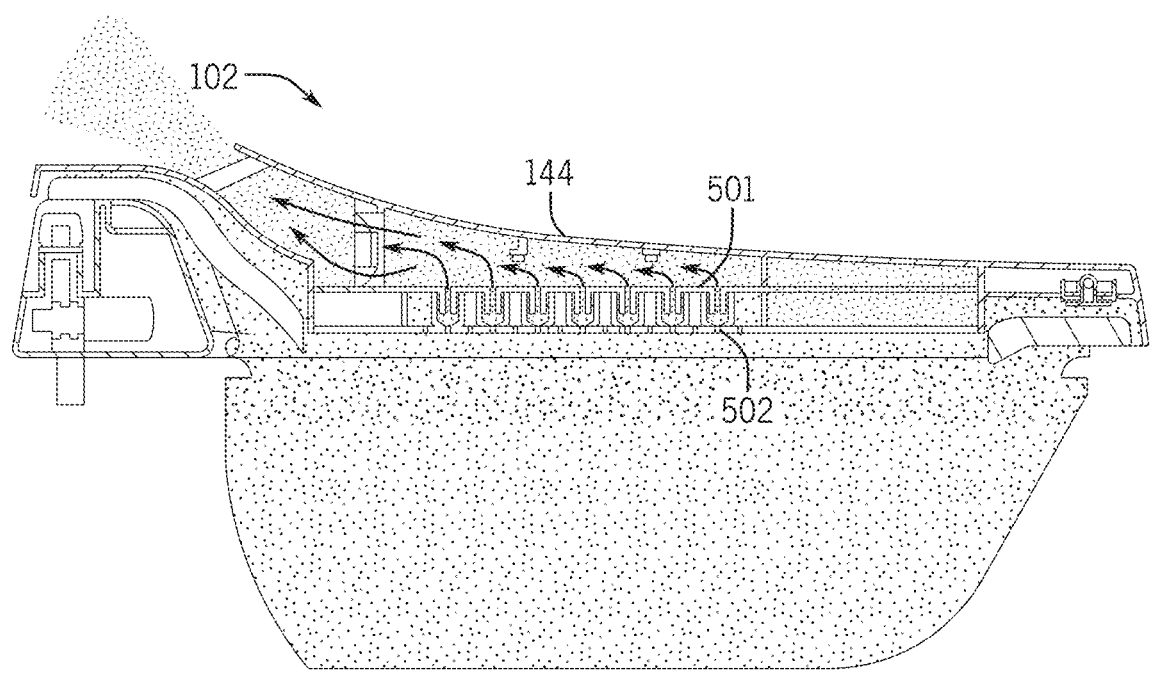
FIGS. 15A and 15B illustrate an example cyclone module for the sanitization system.
Figure 15B:
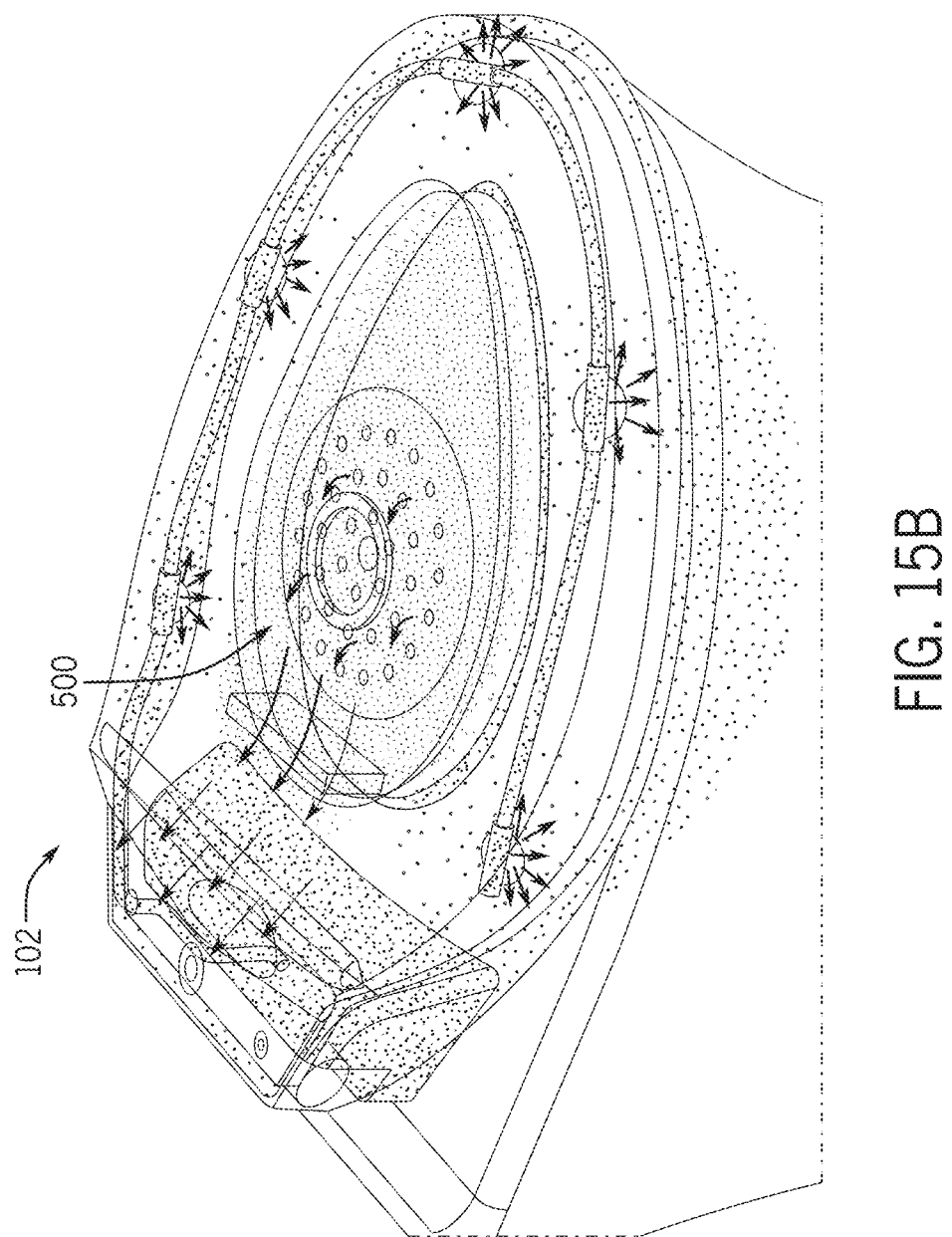

FIGS. 14A and 14B illustrate an example cyclone module 500 for the sanitization system. FIGS. 15A and 15B illustrate an example cyclone module 500 for the sanitization system. The cyclone module 500 may include a plurality of cyclones 501 each having a passage 502 therethrough. Additional, different, or fewer components may be included.

The cyclone module 500 is configured to remove the aerosols from the plume or the mist using centrifugal force. The cyclone module 500 may include many cyclones 501, which are individually relatively small in order to cause a lower overall pressure drop in the process of applying the centrifugal force to separate the aerosols from the plume or the mist.

Figure 16:
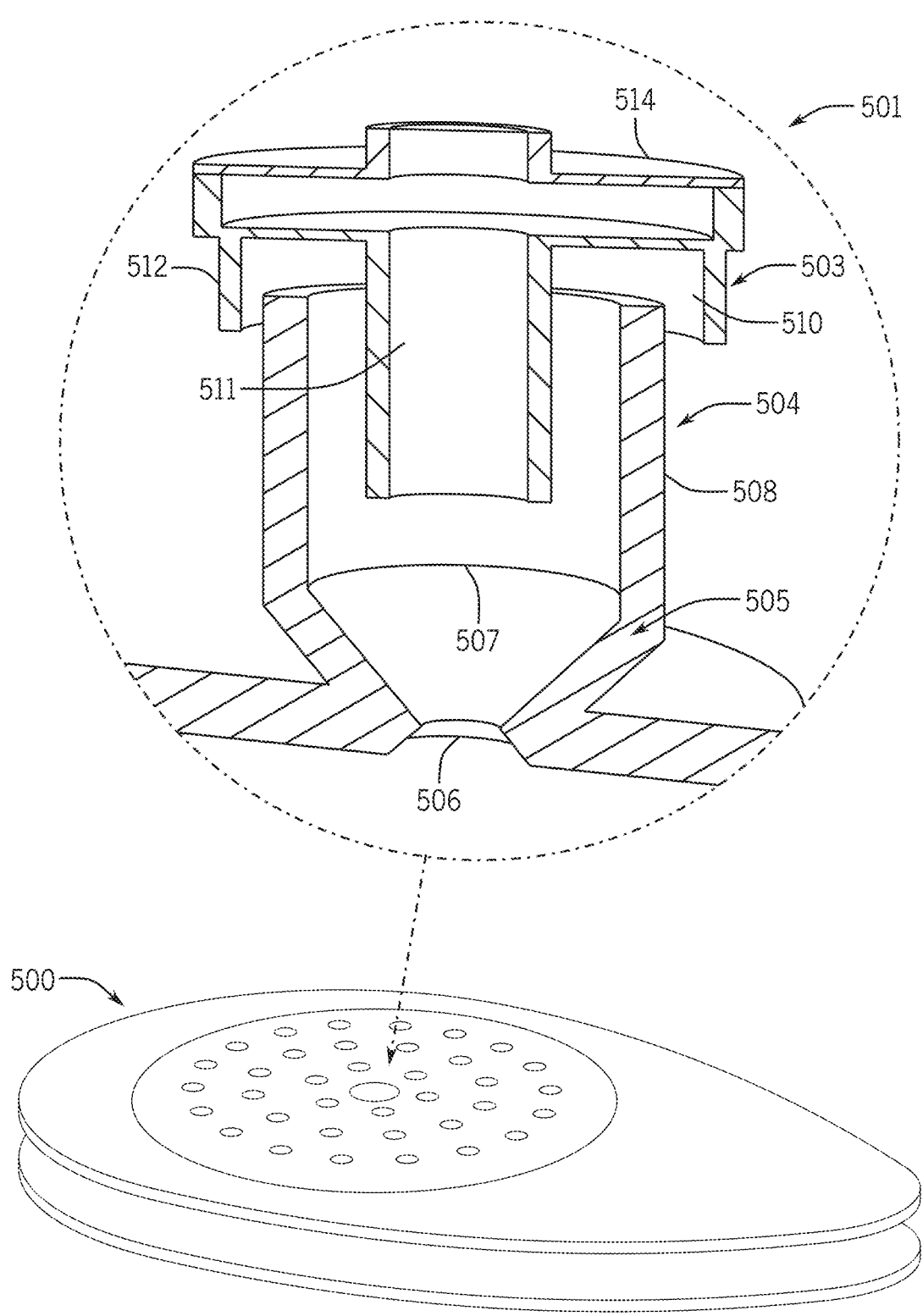
FIG. 16 illustrates a detailed view of a cyclone.

FIG. 16 illustrates an example cyclone 501 in more detail. The cyclone may include a cap portion 503, a longitudinal portion 504, and a tapered portion 505 that together form the passage 502 through the cyclone 501.

The tapered portion 505 may connect a first circular aperture 506 to a second circular aperture 507 having a diameter greater than a diameter of the first circular aperture 506. A first wall extends from the first circular aperture 506 to the second circular aperture 507. A first pipe 508 extends from the second circular aperture 507 to a third circular aperture 510. A second pipe 511 having a diameter less than the diameter of the second circular aperture 507 and disposed in the first pipe 508 a distance away from the second aperture 507. A wall 512 is located outside of the first pipe 508 and at least partially encircling the second pipe 511. A perimeter of cap 514 is secured to the wall 512. The second pipe 511 pass through the cap 514. In one example, a diameter of the third circular aperture 510 is the same as the diameter of the second circular aperture 507.

The first circular aperture 506 accelerates the flow of air in the cyclone 501. The higher rotational speed impart centrifugal force on the particles suspended in the air pushing the partings against the pipe 508. The second pipe 511 acts to separate the particles from the air because the air travels through the second pipe 511 and the particles are pushed through the third circular aperture 510.

The cyclones 501 may be formed from a transparent material such as plastic or glass. The wall of the cyclones 501 may be coated with a catalyst (e.g., photocatalyst) so that the particles separated from the air flow that are against the walls of the cyclone react with the catalyst. All of the surfaces inside the cyclone may be constantly irradiated by the light source 144, activating the oxidation process. The cyclones 501 allow an extended resident time for the air/mist in the presence of the ultraviolet light and catalyst increasing the effectiveness of the ultraviolet light and system overall. As a result the sanitization system is self-cleaning and requires little maintenance.

Figure 17A:
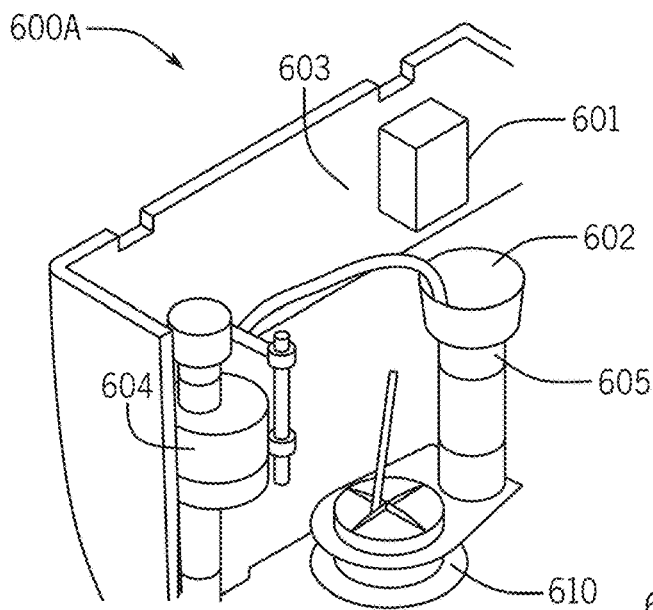
FIGS. 17A, 17B, and 17C illustrate various flush system for a toilet that incorporates the sanitization system.
Figure 17B:
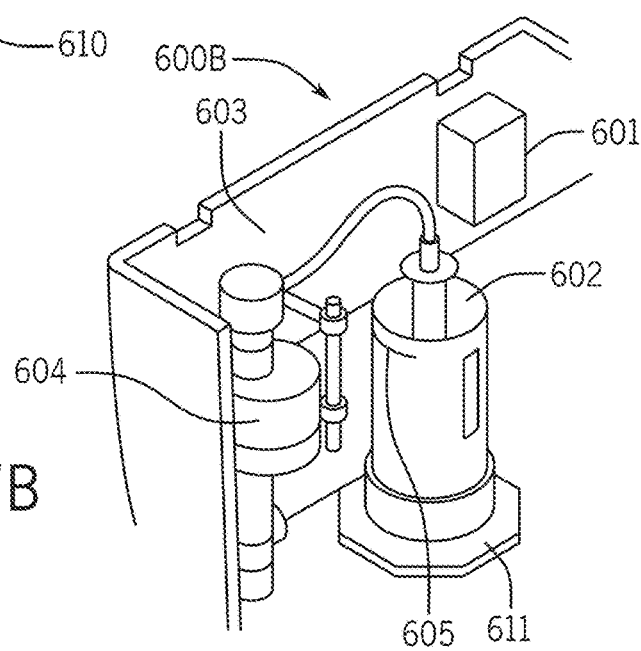
Figure 17C:
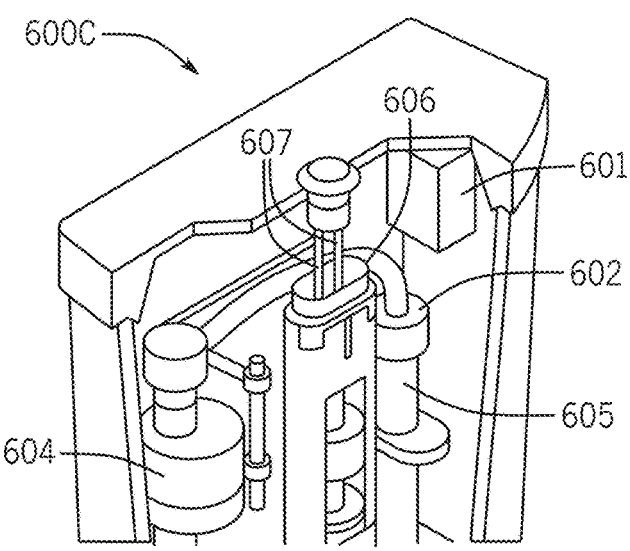

FIGS. 17A, 17B, and 17C illustrate examples of toilet types that may be integrated with a tank sanitization system. In any of these examples, a flush cycle may be siphonic flush where the water is released to the siphon jet to initiate the flush or a wash down flush where the water is released to a rim passage to initiate the flush.

FIG. 17A illustrates a flapper system 600A in which a flapper 610 that seals the tank from releasing water until the flush cycle is initiated. The flapper 610 is hinged and opens slowly to break the seat. A float 604 may define a waterline 605. A rim feed hose 603 may provide water to the rim passage through the overflow tube 602.

FIG. 17B illustrates a canister system 600B in which a canister 611 seals the tank from releasing water until the flush cycle is initiated. The canister 611 includes a flush valve supported by a cylindrical canister coupled to the valve. When the flush is initiated, the canister lifts up to release water. Rather, then a slow hinged opening on one side of the valve as in the case of the flapper 610, the entire opening of the flush valve is opened at one to allow a larger amount of water down into the valve at once, increasing flushing power. Waterline 605 is also defined by float 604. The rim feed hose 603 may provide water to the rim passage through the overflow tube 602 and then through the canister 611.

FIG. 17C is a dual flush canister system 600C may provide multiple types of flush, such as a full flush and a half flush. The rods 607 may operate plunger 606 differently to cause the multiple types of flushes. Waterline 605 is also defined by float 604. The rim feed hose 603 may provide water to the rim passage through the overflow tube 602 which is separated from the plunger 606.

In any of these examples, a sanitization system 601 may be mounted to the interior of the tank at a predetermined relationship to the overflow tube 602 that leads to one or more rim channels of the toilet 100. The sanitization system 601 may generate a fluid that travels through the overflow tube 602 and into the toilet bowl 101. The fluid may travel through the flush valve. The fluid may be a liquid, a mist or a fog. The fluid may include hydrogen peroxide ($H_2O_2$). The fluid may be lighter than water but heavier than air. Thus, the force of gravity allows the fluid to travel through the overflow tube 602 and/or flush valve into the toilet bowl 101. The fluid may fill the toilet bowl 101 from the bottom up.

As an initial matter, the fluid may clean the interior channels of the toilet 100 and the toilet bowl 101. The fluid manages the odors (e.g., volatile compounds), reduces mold in the rim channels, and cleans the inside of the toilet bowl.

In addition, the fluid may interact with any of embodiments of the plume cleaning assembly in order to clean the plume and other aerosols found within the toilet bowl 101.

Figure 18:
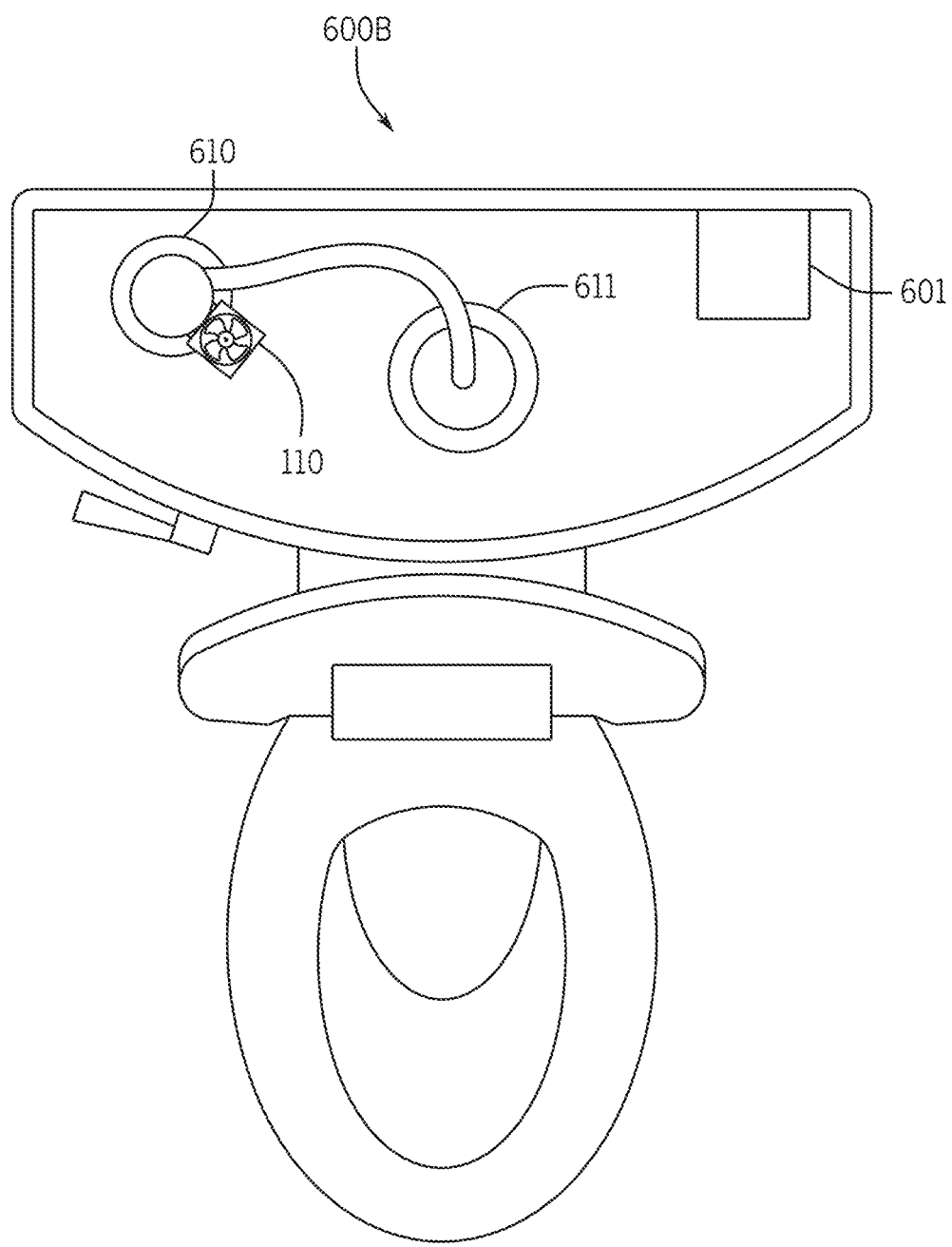
FIG. 18 illustrates a sanitization system in a tank of a toilet.

FIG. 18 illustrates a sanitization system in a tank of a toilet including canister system 600B. The sanitization system 601 may include a fogging device. In some examples, a fan 110 may direct the fog or mist toward the overflow tube 602. To help the transfer of the fog from the tank to the bowl, the tank lid may be sealed tightly (e.g., with an additional sealing mechanisms). In addition, the concentration of the fog in the bowl may be regulated by adjusting one or more other seals. Example seals may be between the rim and the toilet seat and/or between the toilet seat and the lid. The sanitization system 601 includes a mister housing within the tank of the toilet and a conditioning unit that generates mist and provides the mist through at least one channel of the toilet.

Figure 19A:
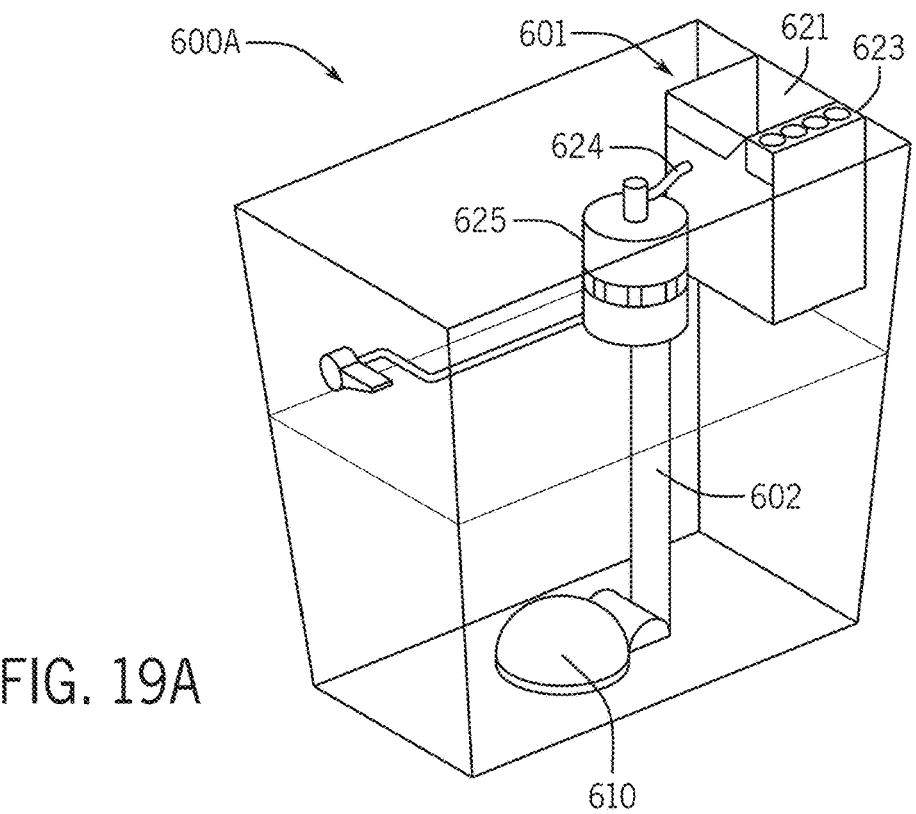
FIGS. 19A and 19B illustrates example implementation of the sanitization system with a flapper flush system.
Figure 19B:
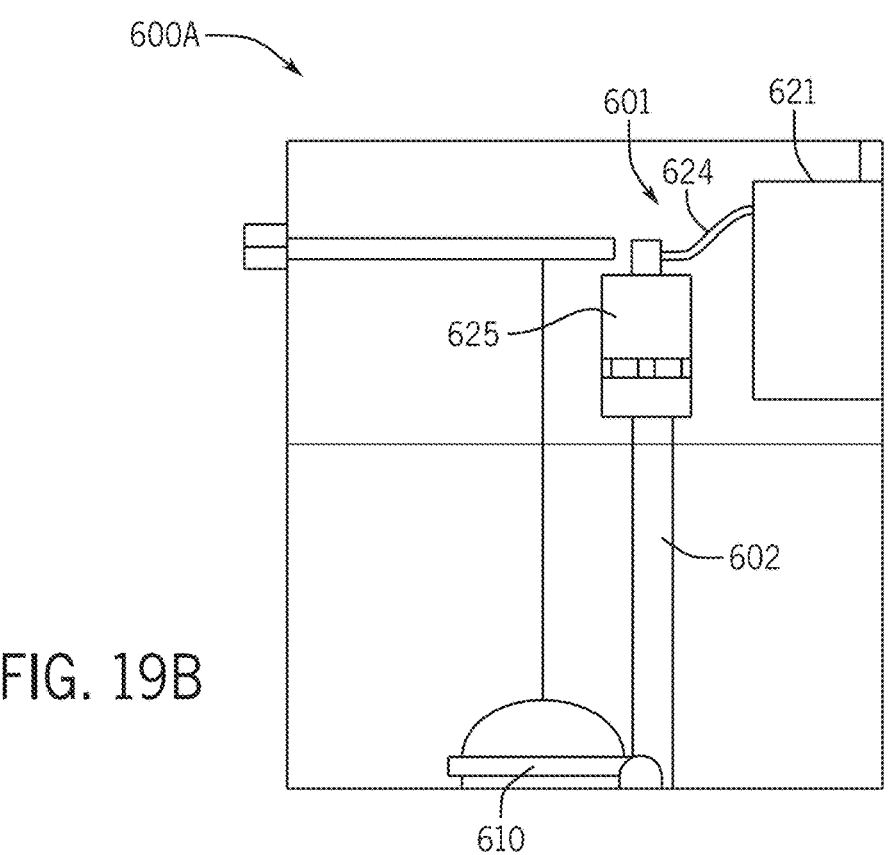

FIGS. 19A and 19B illustrates example implementation of the sanitization system 601 with a flapper flush system. The sanitization system 601 may include a reservoir 621, a battery 623, a connection tube 624, and a mister 625. The mister 625 includes components enclosed within the mister housing. Alternatively or additionally, the reservoir 621 and housing including the reservoir 621 and the battery 623 may be the mister housing. The reservoir 621 may store a fluid for generation of the mist. The battery 623 may power a pump (not shown) for delivering the fluid through the connection tube 624 to the mister 625. The connection tube 624 may be secured to a cap 632 of the reservoir 621. The connection tube 624 connects the conditioning unit or mister 625 to the overflow mechanism 602. The conditioned flow flows through the overflow mechanism 602 to the at least one channel of the toilet 100.

In addition to the transport of fluid, from the connection tube 624 may be associated with a power cable (e.g., the connection tube 624 may be coupled to the power cable) for providing power to the mister 625.

Figure 20:
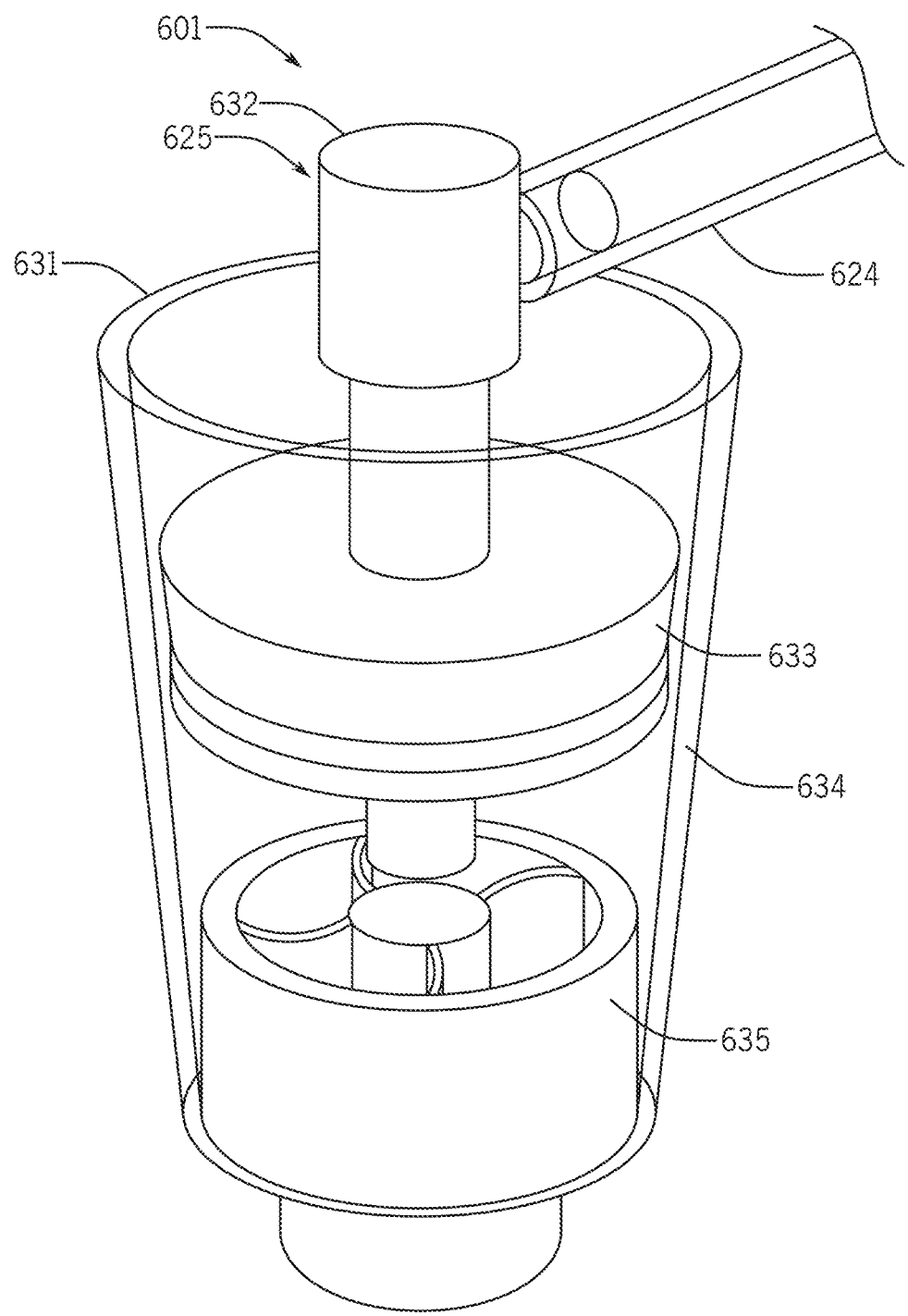
FIG. 20 illustrates a piezo mister for the sanitization system.

FIG. 20 illustrates an example piezo mister 625 for the sanitization system. The fluid feed from the connection tube 624 is provided to a housing 631 including a piezoelectric element 633, a horn 634, and a push fan 635. The piezoelectric element 633 may generate an ultrasonic vibration that breaks of the liquid having particles of approximately a predetermined size (e.g. tens of microns). The horn 634 in an ejection nozzle that propels the particles into a mist. The push fan 635 provides a flow to the fluid including the particles.

Figure 21A:
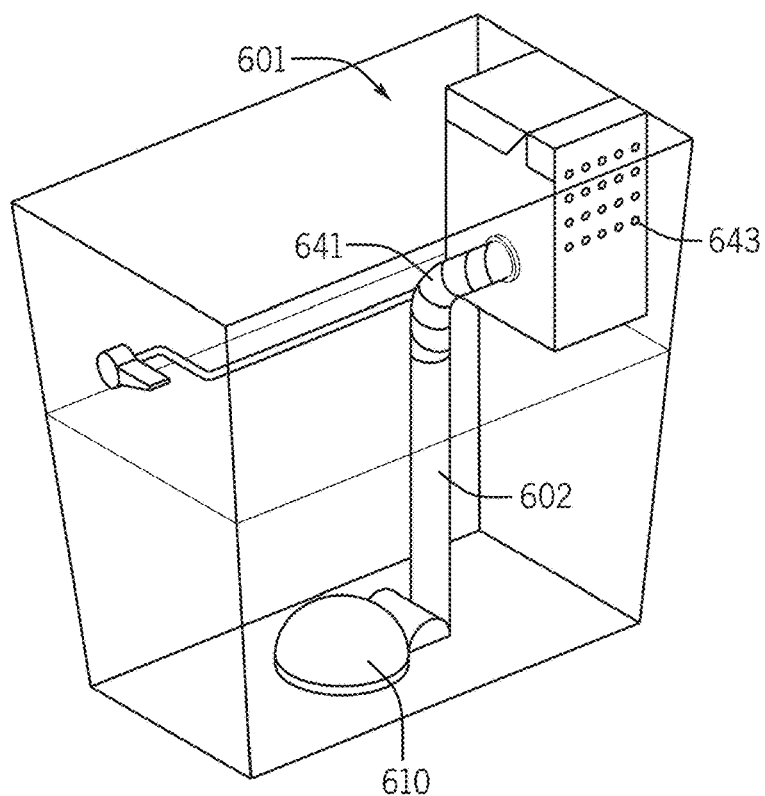
FIGS. 21A and 21B illustrates example implementation of the sanitization system with a flapper flush system.
Figure 21B:
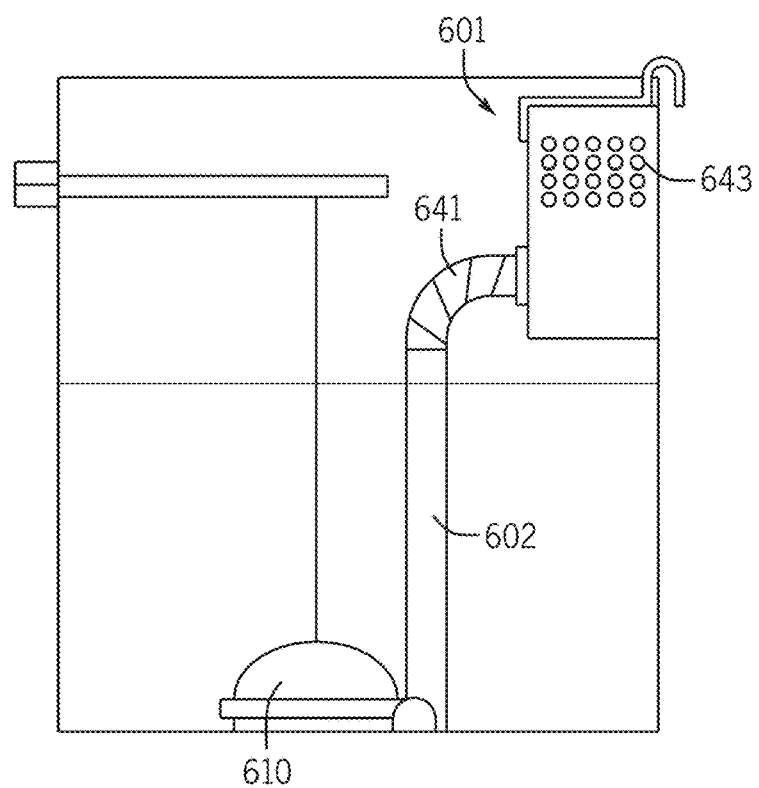

FIGS. 21A and 21B illustrates example implementation of the sanitization system 601 with a flapper flush system 610. This embodiment may include an expandable hose 641 to connect the sanitization system 601 with the overflow tube 602. This embodiment may include a vent 643 (one or more vent holes) for allowing air into the sanitization system 601 for production of the mist.

Figure 22A:
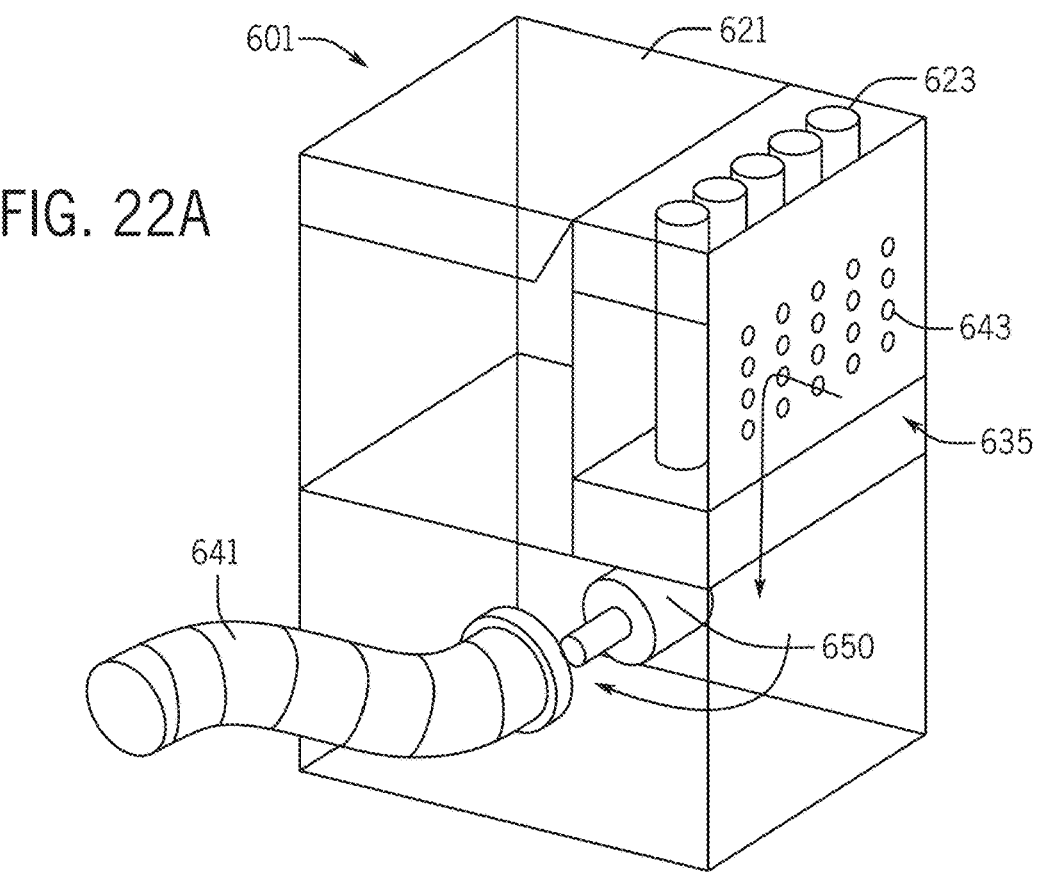
FIGS. 22A and 22B illustrates an example sanitization system with an electrolysis reactor.
Figure 22B:
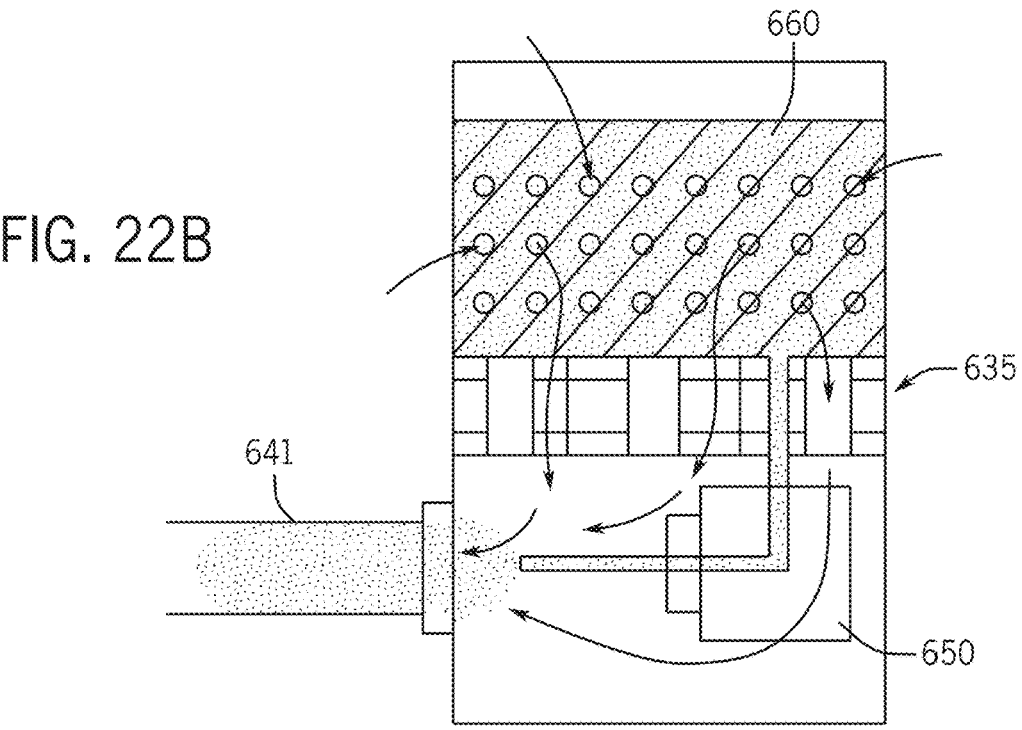

FIGS. 22A and 22B illustrates an atomizer 650 for the sanitization system. The atomizer 650 may be gravity fed as air flows down under gravity, with optional assistance from fan 635. The air may flow through a filter such as charcoal bed 660. The atomizer 650 is a device for emitting the liquid (e.g., hydrogen peroxide) as a fine spray.

Figure 23A:
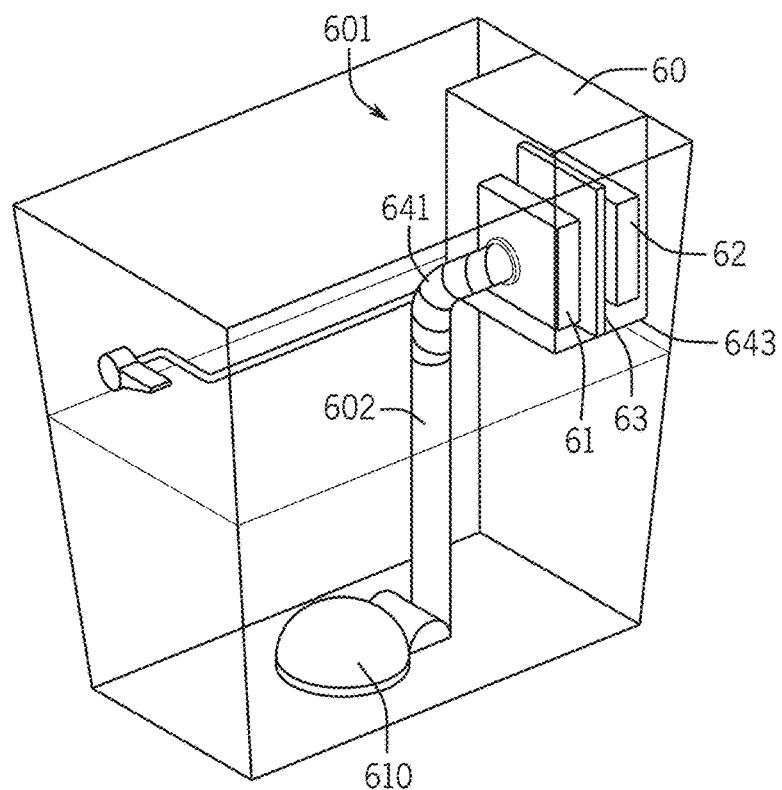
FIGS. 23A and 23B illustrates an atomizer for the sanitization system.
Figure 23B:
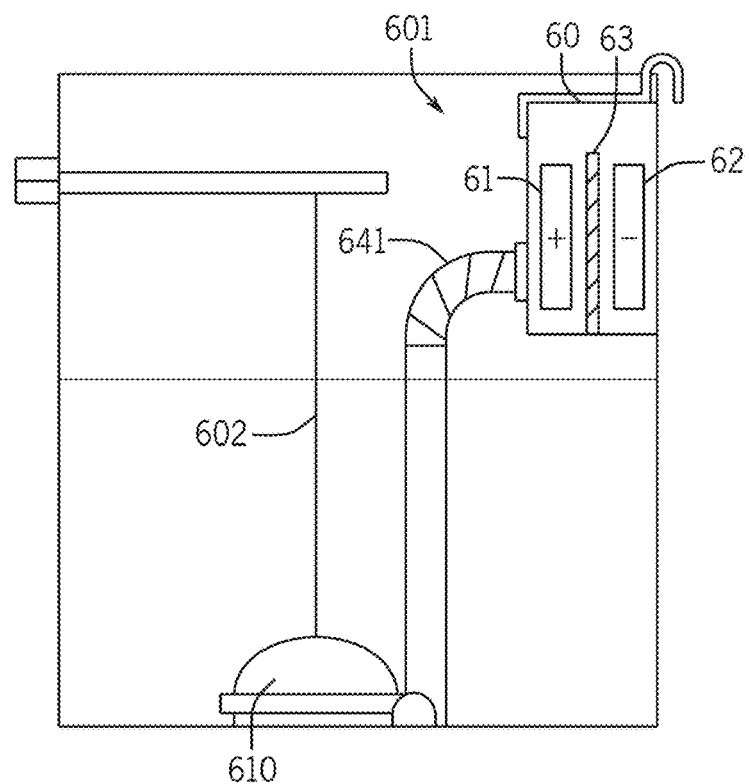

FIGS. 23A and 23B illustrate another embodiment in which the fluid from the sanitization system 601 may be electrolyzed water. As discussed in examples herein, an electrolyzed water reactor 60 may perform electrolysis within sanitization system 601 via a cathode 61 and anode 62. The tank 108 may include a separate housing that defines the reactor 60 and includes an anode compartment for the anode 62 and a cathode compartment for the cathode 61, which may be separated by a porous partition 63. In the anode compartment, a cleaning solution (alkaline) is produced, and in the cathode compartment, a sanitizing solution (acidic) is produced.

Figure 24:
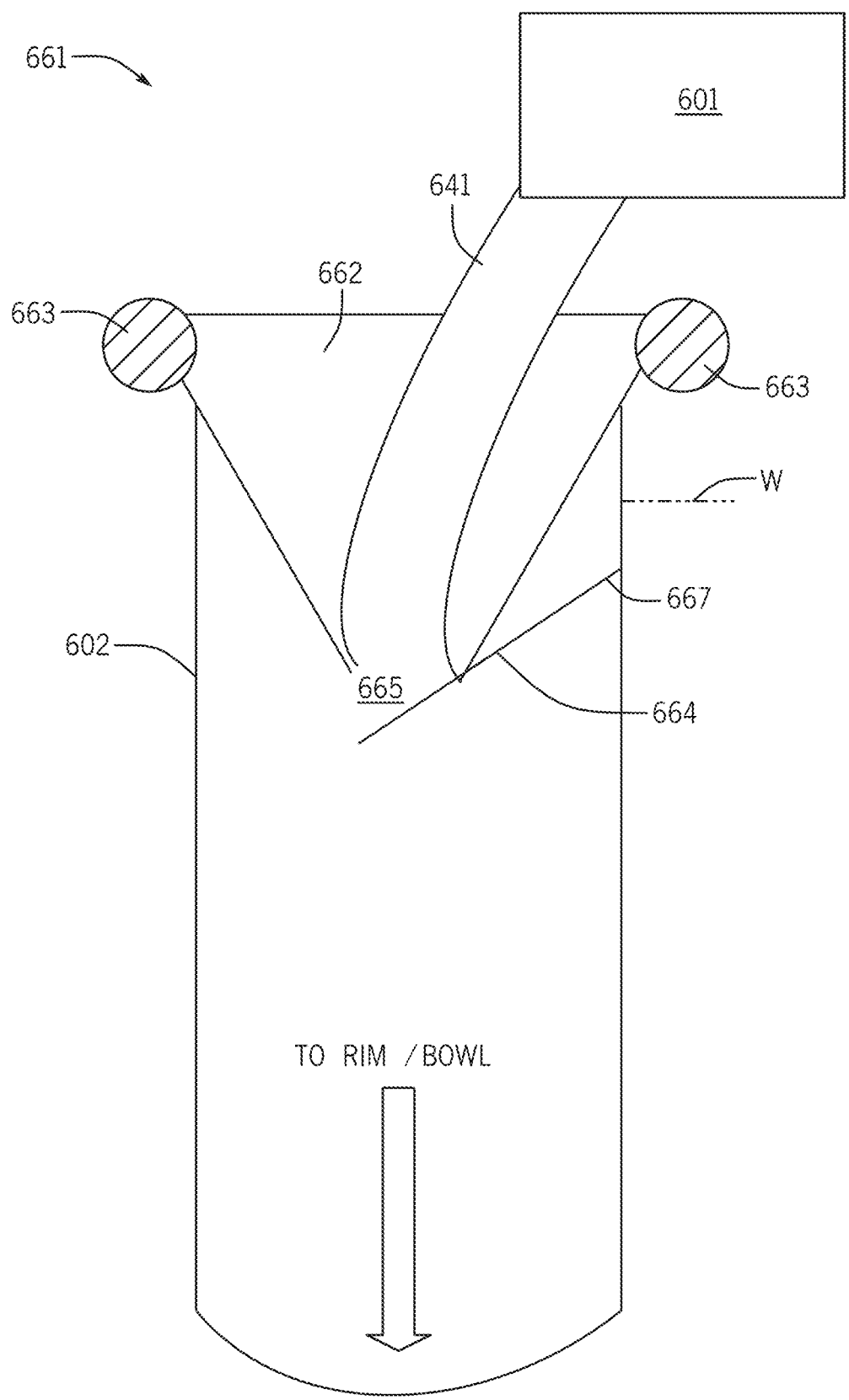
FIGS. 24 and 25 illustrate an example float valve system for the sanitization system.
Figure 25:
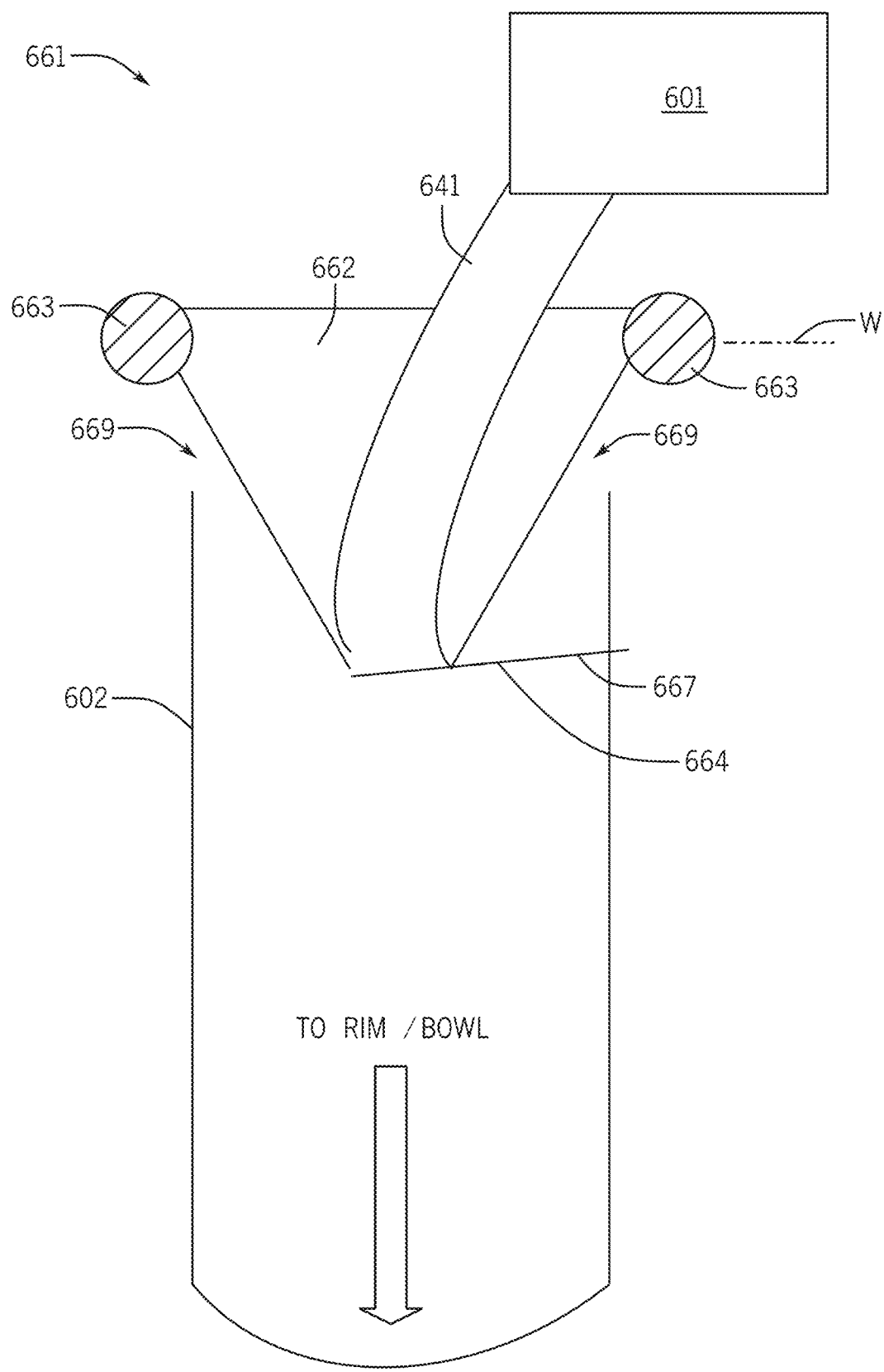
Figure 26:
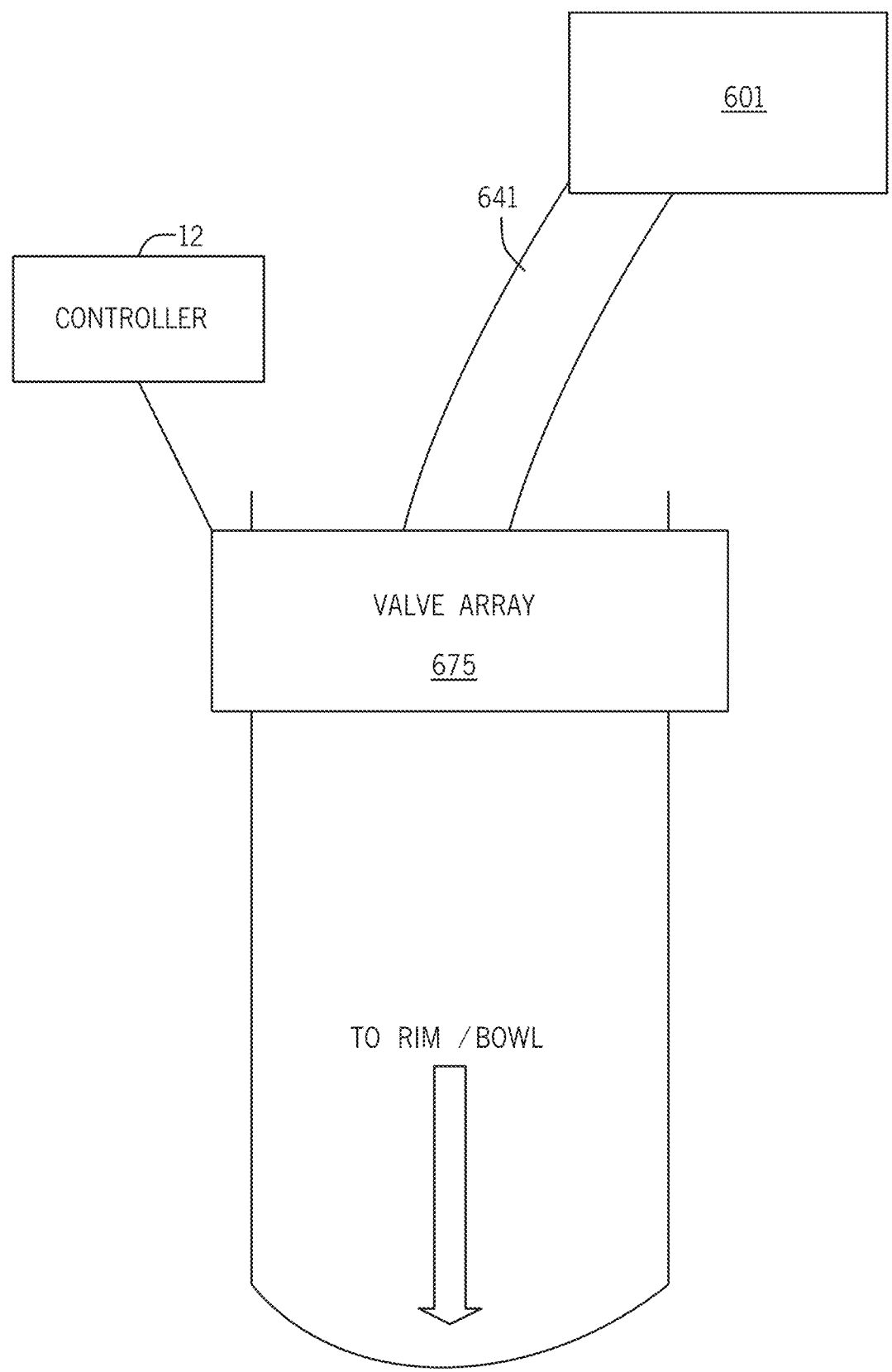
FIG. 26 illustrates an example electronic valve system for the sanitization system.

FIGS. 24-26 illustrate example valve systems for the overflow tube 602 and the sanitization system 601. In FIG. 24, the overflow tube 602 is closed to the overflow of water from the tank and the sanitization system 601 is opened to the overflow tube 602. In FIG. 25, the overflow tube 602 is opened to the overflow of water from the tank and the sanitization system 601 is closed to the overflow tube 602. The valve systems may be controlled by the water level W in the tank. FIG. 26 illustrates an example where an electronic controller controls the valve systems.

FIG. 24 illustrate the overflow tube 602 connected to the sanitization system 601 via a hose 641 and a valve system 661. The valve system 661 may include an overflow valve member 662, one or more floats 663, and a sanitization fluid valve 664.

When the water in the tank is below a predetermined level, the overflow valve member 662 closes the overflow tube 602 and the sanitization fluid valve 664 is opened to allow the sanitization fluid to flow from the sanitization system 601 through the opening 665 into the overflow tube 602 to one or more channels of the toilet and into the rim apertures and finally into the bowl of the toilet. The sanitization fluid valve 664 may be biased to be open by a spring or gravity. The sanitization fluid valve 664 may be coupled to the overflow valve member 662 so that when the overflow valve member 662 opens, the sanitization fluid valve 664 closes the opening 665. The sanitization fluid valve 664 may be pivotable at pivot 667 to open and close the opening 665 between the hose 641 and the overflow tube 602.

As water fills the tank surrounding the overflow tube 602, a buoyant upward force on the one or more floats 663 lifts the one or more floats 663, which are coupled to the overflow valve member 662. As the floats 663 are pushed up, openings 669 are revealed to allow water to flow into the overflow tube 602. At the same time, or nearly the same time, as the overflow valve member 662 moves upward, the sanitization fluid valve 664 may be pulled closed by the overflow valve member 662 to close the opening 665.

FIG. 26 illustrates the controller 12 in communication with a valve array 675. The valve array 675 may include at least one valve that opens the sanitization system 601 to the overflow tube 602 and at least one valve that opens the overflow in the water tank to the overflow tube 602. The controller 12 may generate valve commands for individual valves of the valve array 675.

The controller 12 may cause the overflow tube 602 to be open by default. In response to a cleaning cycle, the controller 12 may close a valve corresponding to the overflow tube 602 and open a valve corresponding to the sanitization system 601 to allow the sanitization fluid to flow through the overflow tube 602 to the rim apertures of the toilet bowl.

Figure 27A:
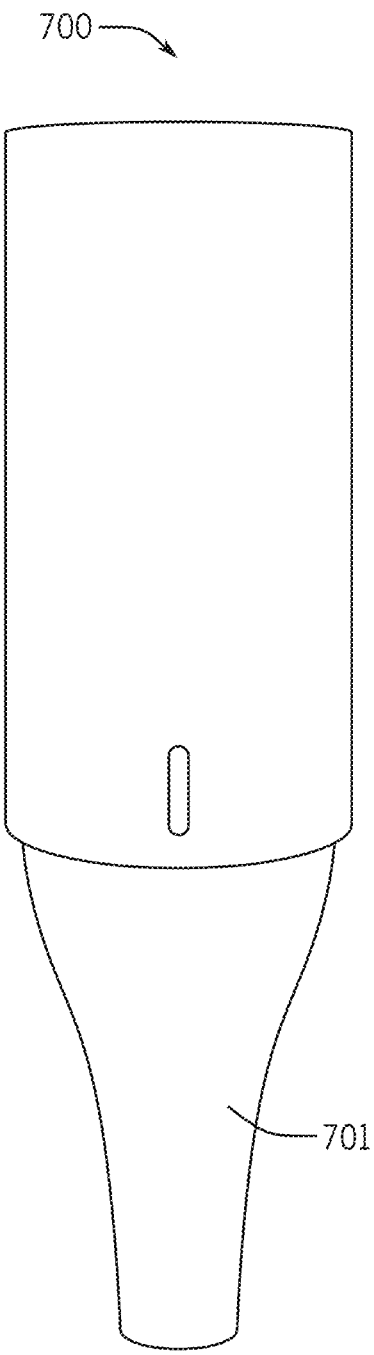
FIGS. 27A and 27B illustrates a first embodiment of a sanitization system for a dryer.
Figure 27B:
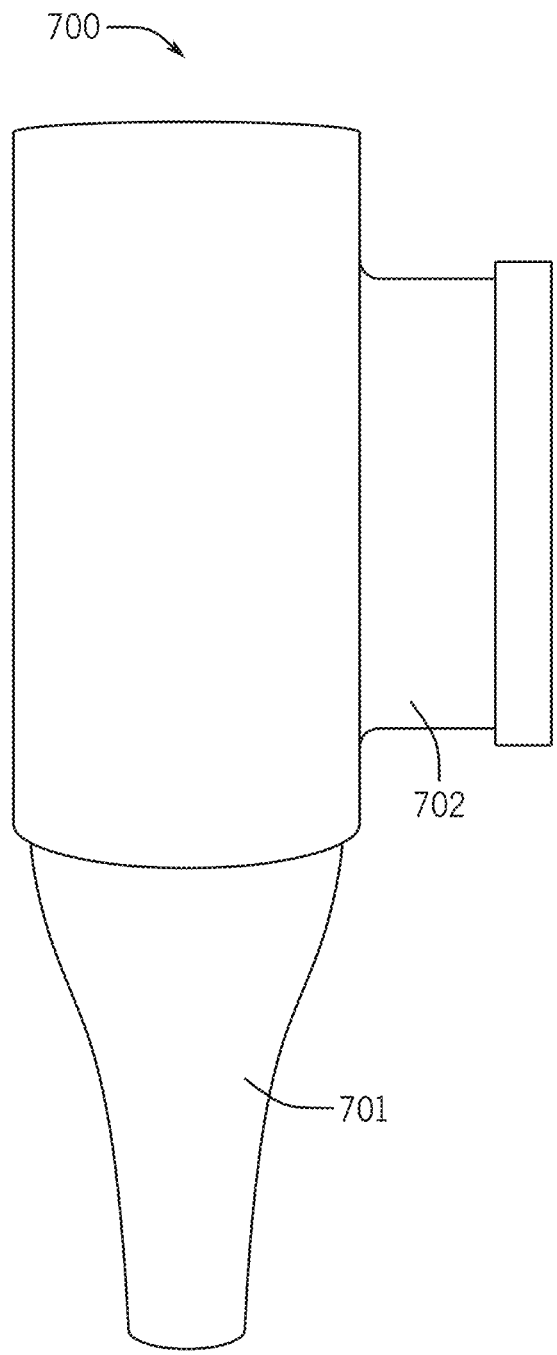

FIGS. 27A and 27B illustrates a first embodiment of a sanitization system for a dryer 700. FIG. 27A is a front view, and FIG. 27B is a side view of the dryer 700. The dryer 700 may be wall mounted by support 702 and provide a sanitized towel 701 for drying hands or other objects. The towel 701 may be sanitized, irradiated, or otherwise cleaned to remove biological material. In addition to the following description, it should be understood that any of the modules (e.g., an impactor module 200, an electrostatic module 300, a hydroxyl module 400, and a multi-cyclone module 500) may be provided individually or in combination within the dryer 700.

Figure 28:
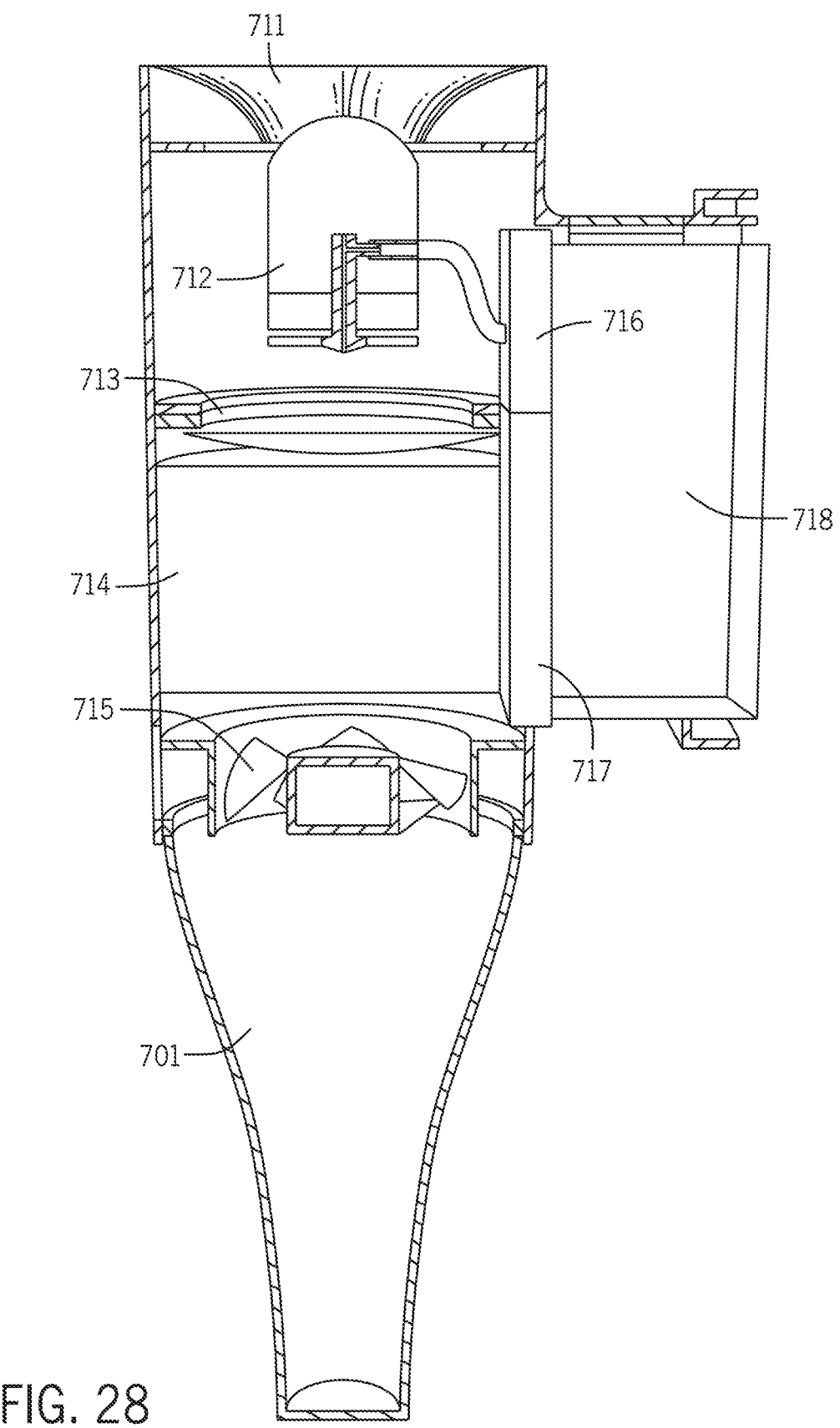
FIG. 28 illustrates a detailed view of the first embodiment of the sanitization system.
Figure 29A:
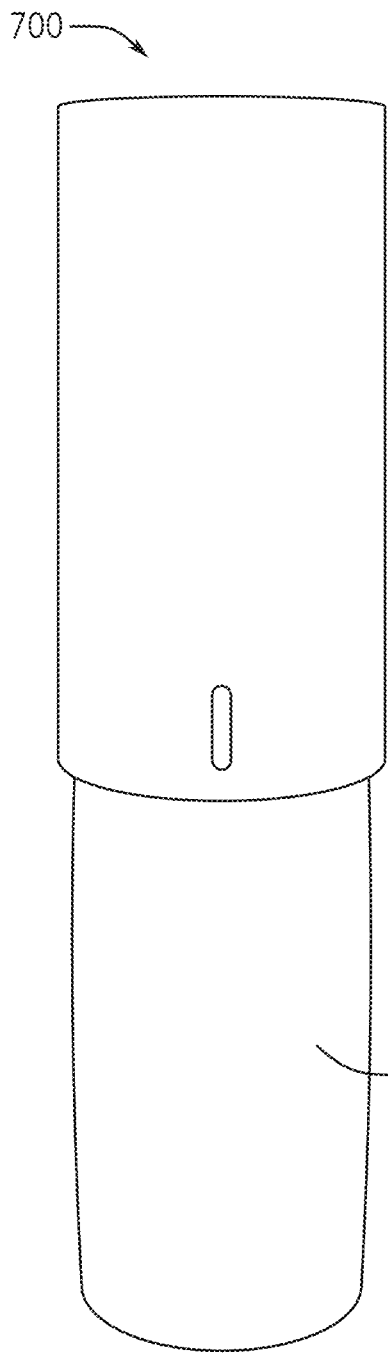
FIGS. 29A and 29B illustrates a second embodiment of a sanitization system for a dryer.
Figure 29B:
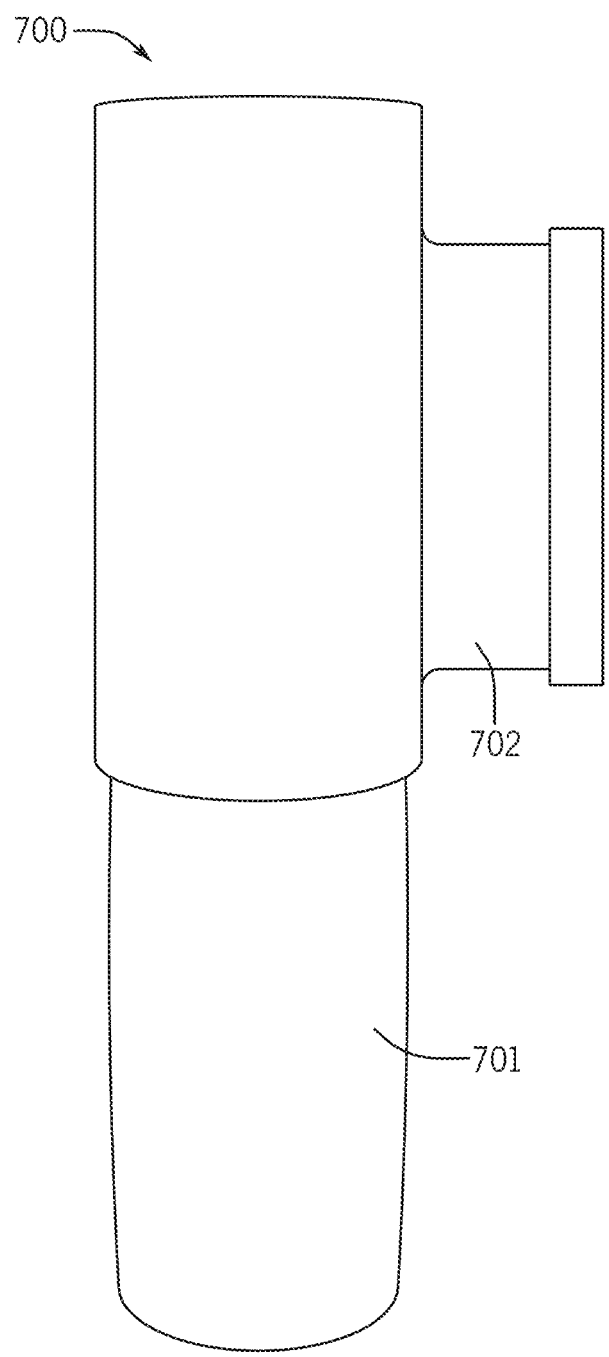

FIG. 28 illustrates a detailed view of the first embodiment of the sanitization system for the dryer 700. The dryer 700 includes an intake 711, a mister (e.g., piezo mister) 712, a light source 713, a foam 714, a fan 715, a pump 716, a controller 717, a reservoir 718, and the towel 701. The intake takes in air from the ambient environment. The controller 717 may be implemented by the control system described herein.

The mister 712 may be supplied with a chemical and/or a solution (e.g., hydrogen peroxide or electrolyzed water) from the reservoir 718 via the pump 716. The mister 712 may be an atomizer (e.g., FIG. 4B) including a horn and piezoelectric element that receives a flow of liquid and meter the flow of liquid and generates a mist through vibration. The mister 712 may include an interdigital transducer configured to generate a surface acoustic wave that causes liquid to mist and exit the atomizer and a power circuit is configured to provide a radio frequency signal to the surface acoustic wave and a driving circuit configured to control an actuating device to meter a flow of liquid into the atomizer. The mister 712 may include a misting wand configured to provide a mist in a configurable predetermined direction.

The light source 713 may be an ultraviolet light that irradiates the mist. The light source 713 may include one or more LED lights. The mist is provided to the open cell catalytic foam 714. The foam 714 slows the mist or flow of air to spend more time irradiated by the light source 713. The particles in the mist also adhere to the foam 714. The light source 713 activates the catalyst in the foam 714 to further oxidize any particles in the foam 714. Through these reactions, hydroxyl and peroxides may be produced, and included in the air flow blown through the towel 701.

The fan 715 generates the air flow to draw air through the foam 714 and the mist generated by the mister 712 into the towel 701. The towel 701 may be in the shape of a sock or a wind sock. The towel 701 may have an open end that is secured to the dryer 700. The other end of the towel 701 may be closed but the towel 701 is semiporous so that some air escapes. The flow of air inflates the towel 701. In some examples, the towel 701 has an opening that is smaller on the bottom end, which is comparable to a windsock. The towel 701 may be formed of a microfiber.

The control board (controller 717) may generate command signals for the mister 712, the fan 715, the light source 713 and the pump 716. All systems may be on when the dryer 700 is on, which may be triggered by a motion sensor. A particular sequence of commands may be provided by the controller 717 to active the light source 713, fan 715, pump 716, etc. at certain times.

Figure 30A:
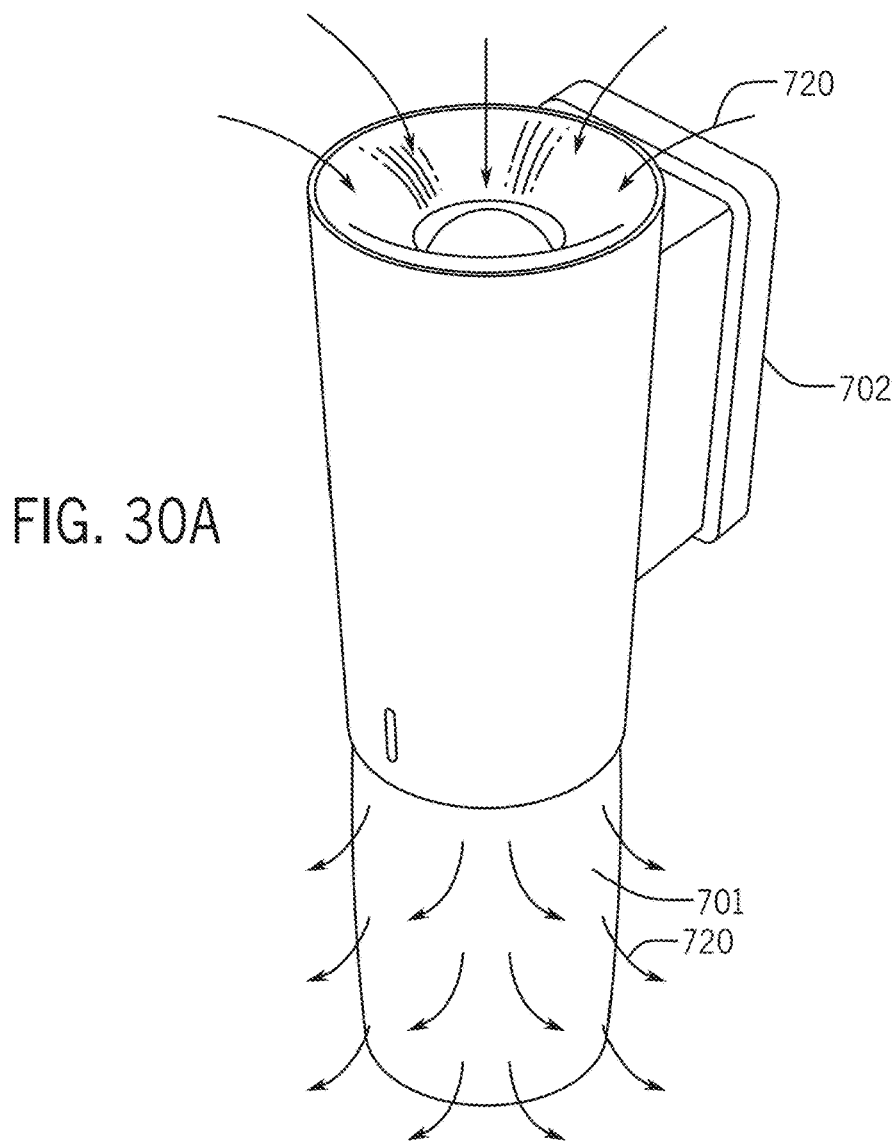
FIG. 30A illustrates an air flow for the second embodiment of the sanitization system.
Figure 30B:
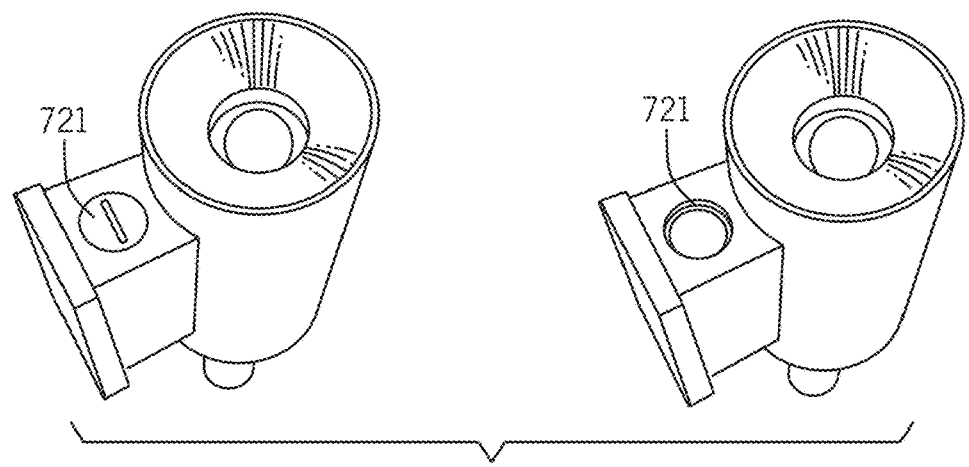
FIG. 30B illustrates a chemical hatch for the second embodiment of the sanitization system.

FIGS. 27A-B illustrate an embodiment with a cone shaped towel 701. FIGS. 29A-B and 30A-B illustrate an embodiment with a cylindrical shaped towel 701. FIG. 30A illustrates a flow 720 through the dryer 700 in a substantially vertical direction to inflate the towel 701. FIG. 30B illustrates the cover or hatch 721 for adding a chemical solution or electrolyzed water to the dryer 700.

Figure 31:
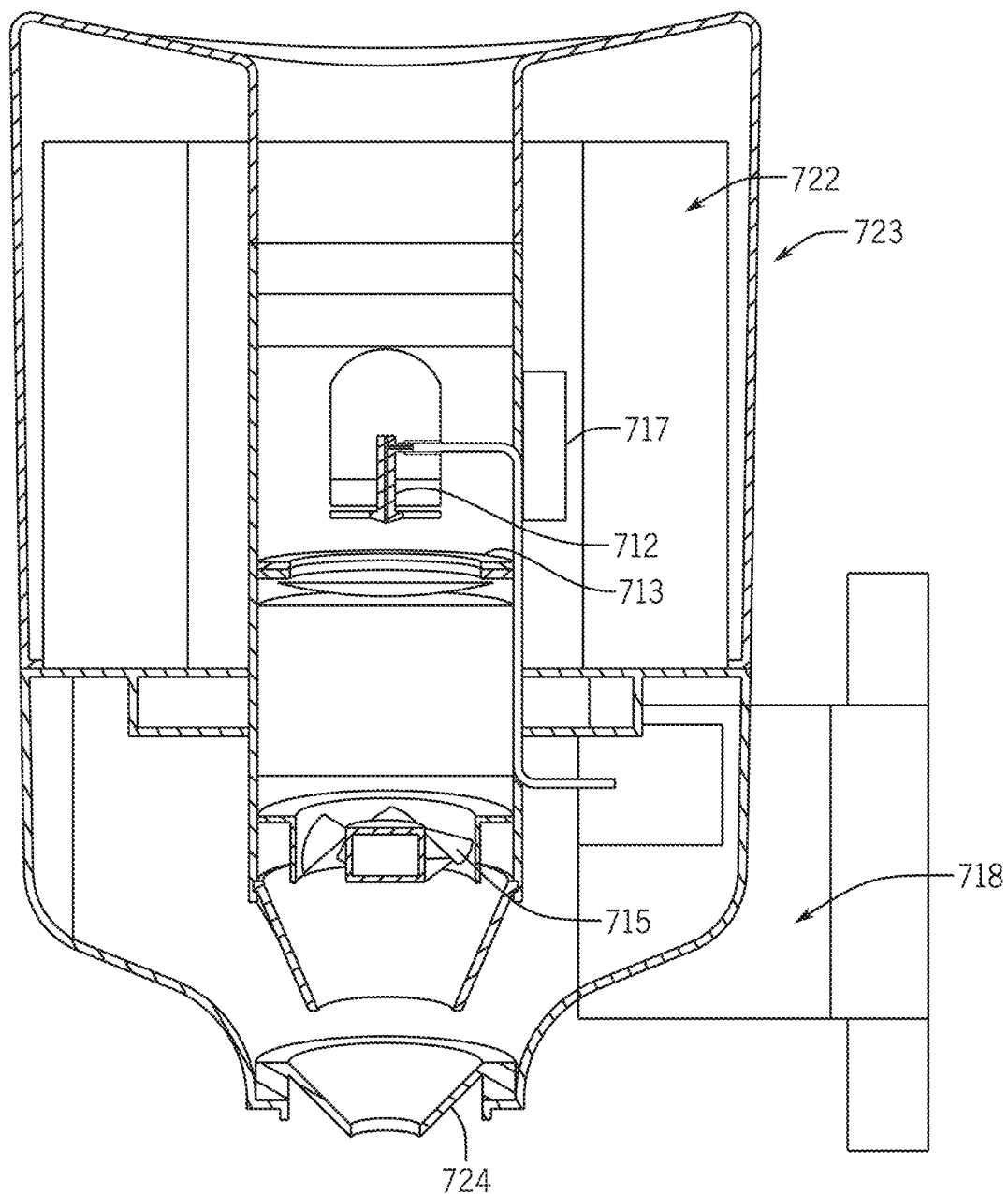
FIG. 31 illustrates a detailed view of the second embodiment of the sanitization system.
Figure 32A:
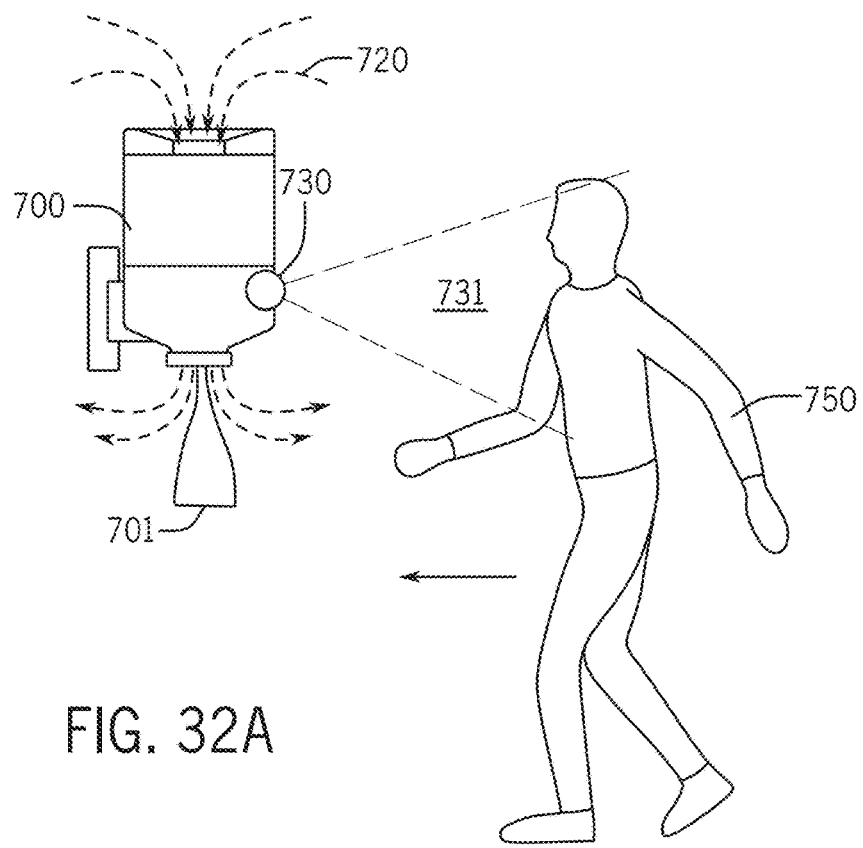
FIGS. 32A, 32B, 33A, and 33B illustrates the operation of the first and second embodiments of the dryer.
Figure 32B:
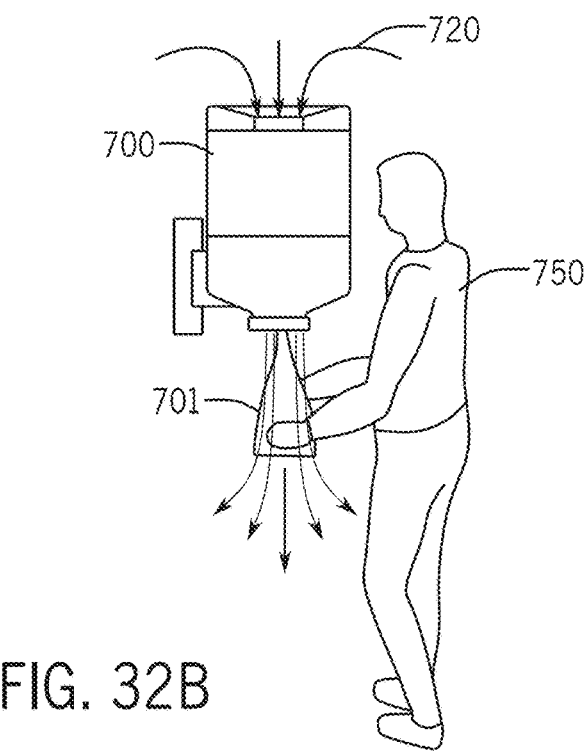
Figure 33A:
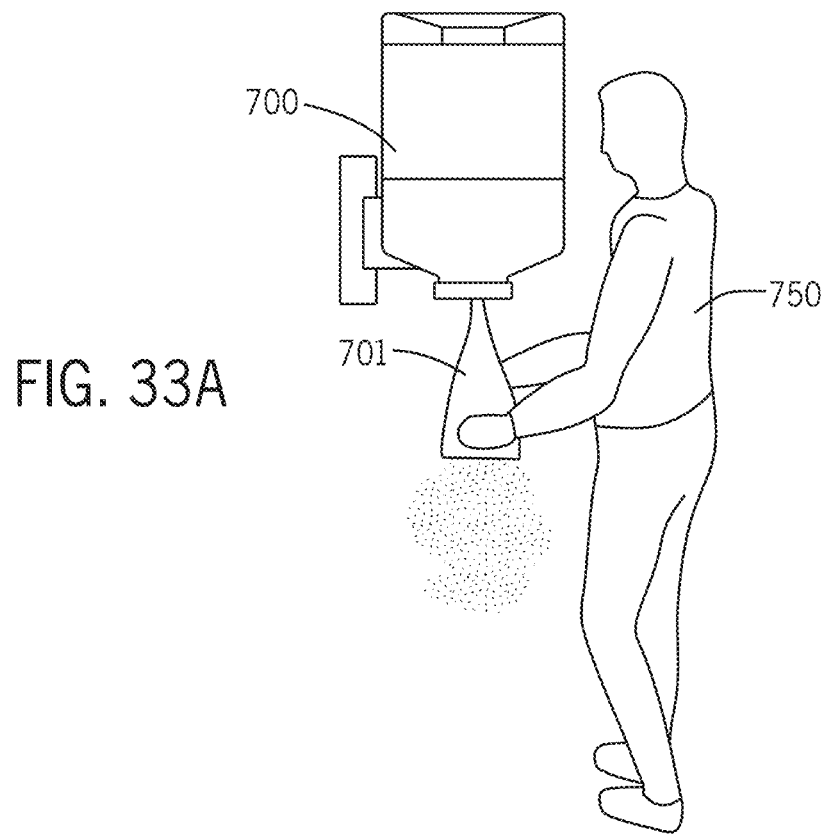
Figure 33B:
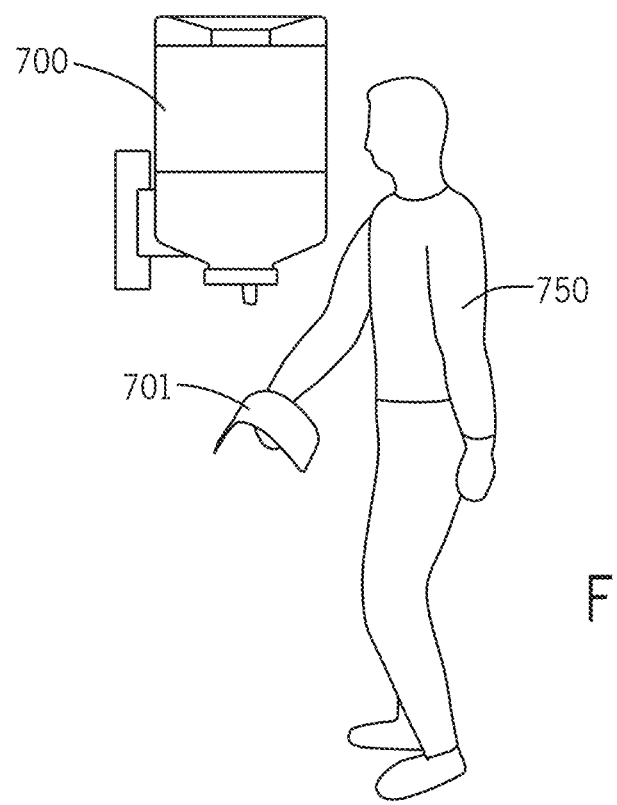

As shown in more detail in FIG. 31, the embodiment of FIGS. 30A and 30B may include a sanitization system for a dryer 700 a disposable towel dispenser including towels 722. The towel dispenser may be shaped in a cylindrical tube 723 that surrounds at least a part of a mandrel nozzle 724.

The mister 712, light source 713, and fan 715 may operate in a similar manner as described above. The pump 716 and controller 717 may also be included. In this case, the air flow allows the towel dispenser to advance another segment of disposable towel to the end of the dryer 700. The air flow inflates the towel segment. The user can use the inflated, sanitized towel the remove the towel for disposal. The next time that the fan is activated another towel segment will move into place.

FIGS. 32A, 32B, 33A, and 33B illustrates the operation of the first and second embodiments of the dryer 700 by a user 750. When the user 750 enters a field of view 731 of a sensor 730 (e.g., optical sensor or other presence or motion sensor), the controller 717 may trigger operation of the mister 712, the light source 713, and the fan 715. The towel 701 is inflated and sanitized. The user dries the user's hands on the towel 701. The towel 701 may be removed (e.g., along a perforation) by the user 750.

Figure 34:
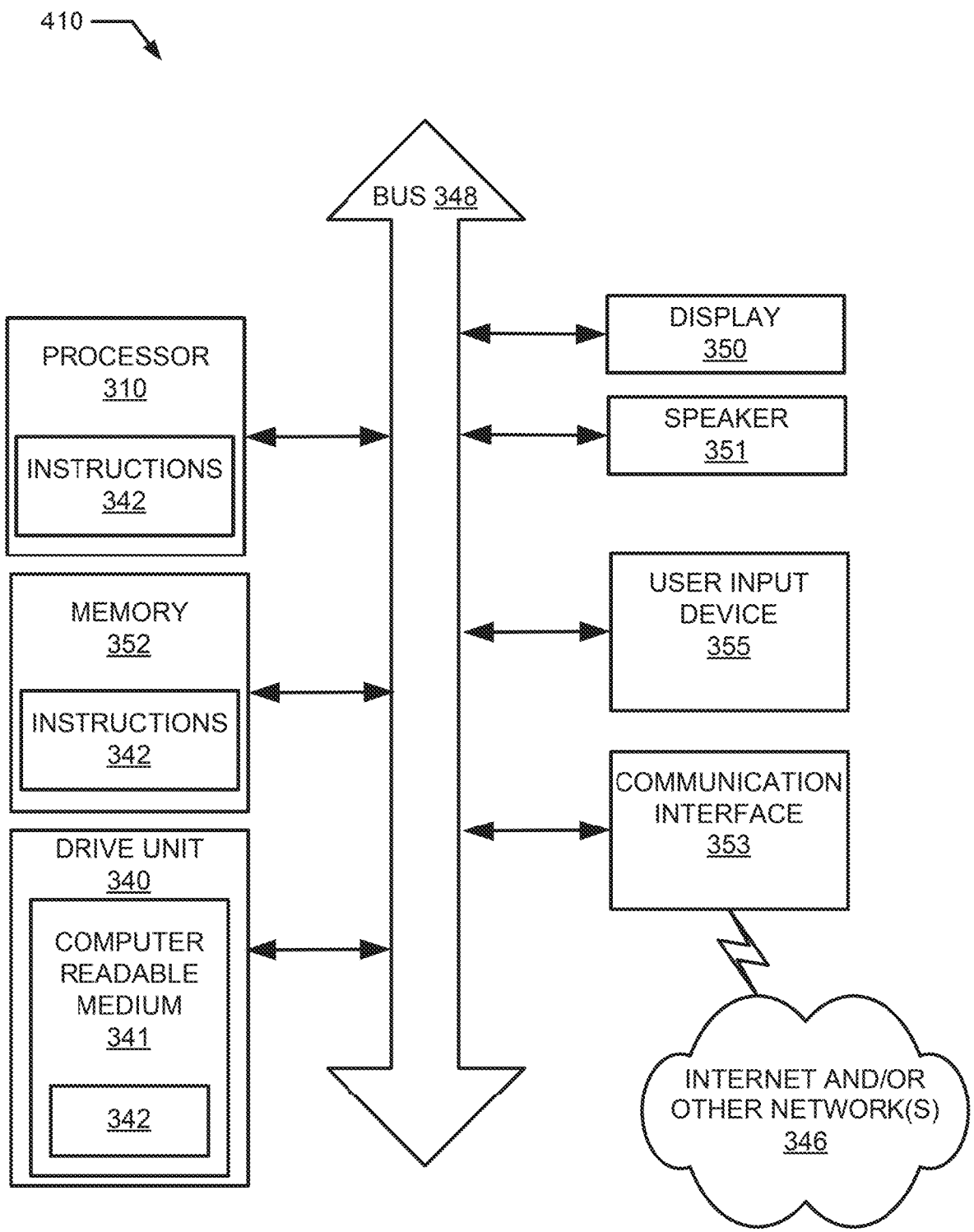
FIG. 34 illustrates an example controller for the sanitization system.

FIG. 34 illustrates an example controller for the sanitization system. The control system 410 may implement any of the controllers described herein included controller 10 and controller 717. The control system 410 may include a processor 310, a memory 352, and a communication interface 353 for interfacing with devices or to the internet and/or other networks 346. In addition to the communication interface 353, a sensor interface may be configured to receive data from the sensors described herein or data from any source for analyzing user inputs, user gestures or position, air and/or water properties or the operation of the appliances described herein. The components of the control system 410 may communicate using bus 348. The control system 410 may be connected to a workstation or another external device (e.g., control panel) and/or a database for receiving user inputs, system characteristics, and any of the values described herein.

Optionally, the control system 410 may include an input device 355 and/or a sensing circuit in communication with any of the sensors. The sensing circuit receives sensor measurements from as described above. The input device 355 may include the switch 150, a touchscreen coupled to or integrated with the mirror, a keyboard, a microphone for voice inputs, a camera for gesture inputs, and/or another mechanism.

Optionally, the control system 410 may include a drive unit 340 for receiving and reading non-transitory computer media 341 having instructions 342. Additional, different, or fewer components may be included. The processor 310 is configured to perform instructions 342 stored in memory 352 for executing the algorithms described herein. A display 350 may be supported by the mirror frame. The display 350 may be combined with the user input device 355.

Figure 35:
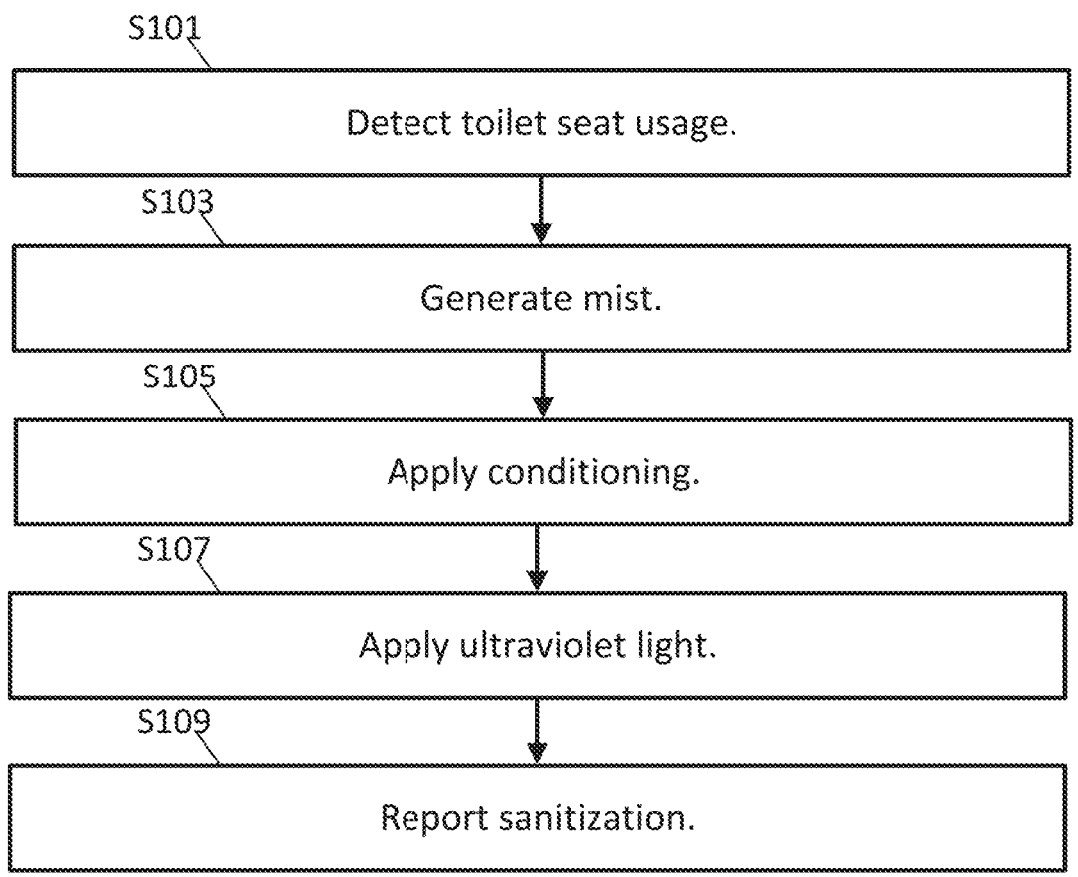
FIG. 35 illustrates an example flow chart for the controller of FIG. 34.

FIG. 35 illustrates a flow chart for the control system 410. The acts of the flow chart may be performed by any combination of the control system 410, the network device or the server. Portions of one or more acts may be performed by the appliance. Additional, different of fewer acts may be included.

At act S101, the controller 410 (e.g., through processor 310) receives data to indicate toilet seat usage. The data could be a timer or sensor data. The sensor may be a pressure sensor that indicates that a user has sat down (e.g., increase in pressure) at the toilet seat or that the user has stood up (e.g., decrease in pressure) after a predetermined time indicative of a usage of the toilet seat. The sensor data may be a user input (e.g., motion sensor or gesture sensor).

At act S103, the controller 410 (e.g., through processor 310) causes the mister to generate a mist configured to adhere to particles in a plume expelled from the toilet. The mist may be diffused or otherwise propelled into the toilet bowl.

At act S105, the controller 410 (e.g., through processor 310) applies conditioning to the mist according to any of the modules described herein including electrostatic charging, catalyst, cyclones, or impactors. At act S107, the controller 410 (e.g., through processor 310) triggers or continues to apply light from a light source (e.g., ultraviolet).

At act S109, the controller 410 (e.g., through processor 310) reports the sanitization or cleaning process, for example, through display 350, speaker 351, or communication interface 353. The display 350 may indicate a status that a cleaning cycle is being performed or has been performed. The status may be displayed in response to the mist generation or another stage of the cleaning cycle.

FIG. 36 illustrates a flow chart for the control system 410. The acts of the flow chart may be performed by any combination of the control system 410, the network device or the server. Portions of one or more acts may be performed by the appliance. Additional, different of fewer acts may be included.

At act S201, the controller 410 (e.g., through processor 310) generates a misting command. The misting command may instruct a mist generator to turn on or enter an active misting mode. The mist generator may include a transducer or piezo electric element that produces a mist cloud from liquid having a sanitization property. The liquid may include a cleaning compound or a chemical having the sanitization property.

At act S203, the controller 410 (e.g., through processor 310) generates a fan command. The fan command may instruct a fan to turn on or enter an active air circulation mode. The fan and the misting generator may be supported by an air cleaner housing, which may be integrated within a toilet seat assembly. The fan may include a blade or impellor configure to draw in air from a fan inlet and expel air from a fan outlet. The air may include a cloud of particles including at least a portion of the mist from the mist generator.

The controller 410 may generate the misting command (act S201) and the fan command (act S203) in either order, in a predetermined sequence, which may have predetermined time interval delays between the misting command and the fan command, and in response to a variety of triggers.

One example trigger is a time period or a schedule. The controller 410 initiates the misting command when a predetermined time has passed since the last misting command. Example time periods may include 10 minutes, 1 hour, or 2 hours. The schedule for the misting commands may be user configurable. The controller may subsequently initiate the fan command, for example after a second time period, to recirculate the mist and or drive the mist to the electrostatic charger.

One example trigger is a flush cycle. The flush cycle may be initiated by a user input to flush the toilet or by sensor data detecting presence near the toilet, the absence of such presence, or any other sensors described herein. In one example, in response to the flush, the controller 410 initiates the misting command to fill the bowl with the mist cloud and subsequently initiates the fan command to recirculate the mist and or drive the mist to the electrostatic charger.

At act S205, the cloud of air is provided to an electrostatic collector. The electrostatic collector removes particles from the cloud. The cloud out of air may be provided, in part, by an internal passage in the air cleaner assembly.

At act S207, particles are collected at the electrostatic collector. The electrostatic collector may be passive, including an electrical charge provided by the materials that form the electrostatic collector or imparted in the manufacturing thereof. That is, the electrostatic collector may be permanently charged with a static charge. In another example, the controller 410 may provide an electrical chart to the electrostatic collector.

At act S209, the cloud is recirculated from the electrostatic collector to the mist generator. The cloud may be recirculated via another air passage that leads from the electrostatic collector back to the mist generator. However, the recirculation path may include the toilet bowl. That is, the electrostatic collected may expel the air cloud to the bowl, which is collected by the inlet of the fan. The controller 410 may receive sensor data and trigger the recirculation sequence based on the sensor data.

Processor 310 may be a general purpose or specific purpose processor, an application specific integrated circuit (ASIC), one or more programmable logic controllers (PLCs), one or more field programmable gate arrays (FPGAs), a group of processing components, or other suitable processing components. Processor 310 is configured to execute computer code or instructions stored in memory 352 or received from other computer readable media (e.g., embedded flash memory, local hard disk storage, local ROM, network storage, a remote server, etc.). The processor 310 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions. Memory 352 may include database components, object code components, script components, or any other type of information structure for supporting the various activities and information structures described in the present disclosure. Memory 352 may be communicably connected to processor 310 via a processing circuit and may include computer code for executing (e.g., by processor 310) one or more processes described herein. For example, memory 298 may include graphics, web pages, HTML files, XML files, script code, shower configuration files, or other resources for use in generating graphical user interfaces for display and/or for use in interpreting user interface inputs to make command, control, or communication decisions.

In addition to ingress ports and egress ports, the communication interface 353 may include any operable connection. An operable connection may be one in which signals, physical communications, and/or logical communications may be sent and/or received. An operable connection may include a physical interface, an electrical interface, and/or a data interface. The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

What is claimed is:

1. A plume cleaning system for a toilet, the plume cleaning system comprising:
   a toilet seat cover;
   a toilet seat;
   a plume cleaner assembly adjacent to the toilet seat cover and the toilet seat and independently removable with respect to the toilet seat cover and with respect to the toilet seat, the plume cleaner assembly comprising:
   a plume cleaner;
   a plurality of apertures arranged with longitudinal axes; and
   a fan positioned to draw plume air through the plurality of apertures for treatment by the plume cleaner and expel the treated plume air out of the plume cleaner assembly in a direction at an angle to the longitudinal axes of the plurality of apertures.

2. The plume cleaning system of claim 1, wherein at least a portion of the plume cleaning assembly is below the toilet seat.

3. The plume cleaning system of claim 1, the plume cleaner further comprising:
   a rounded housing including the plurality of apertures.

4. The plume cleaning system of claim 3, wherein the rounded housing has circular or oval cross section.

5. The plume cleaning system of claim 1, the plume cleaner further comprising:
   at least one radial channel configured to direct the plume air from a toilet bowl to the plurality of apertures.

6. The plume cleaning system of claim 5, further comprising:
   a light source configured to irradiate the plume air in the at least one radial channel.

7. The plume cleaning system of claim 1, the plume cleaner further comprising:
   an output channel configured to direct the treated plume air to the fan.

8. The plume cleaning system of claim 1, the plume cleaner further comprising:
   a bulkhead having a shape corresponding to an opening of the toilet seat, the bulkhead supporting at least the plume cleaner.

9. The plume cleaning system of claim 8, wherein the plume cleaner assembly adjacent to the toilet seat cover includes a cavity configured to receive a light source that is mounted to the toilet sear cover.

10. The plume cleaning system of claim 8, wherein the plume cleaner assembly adjacent to the toilet seat cover includes a transparent portion to provide a light path from a light source to at least one radial channel.

11. The plume cleaning system of claim 1, further comprising:
    a cleaner dock coupled to the toilet seat cover and configured to removably attach the plume cleaner assembly to the toilet seat cover.

12. The plume cleaning system of claim 1, wherein the plume cleaner includes an impactor module.

13. The plume cleaning system of claim 1, wherein the plume cleaner includes an electrostatic module.

14. The plume cleaning system of claim 1, wherein the plume cleaner includes a hydroxyl module.

15. The plume cleaning system of claim 1, wherein the plume cleaner includes a multi-cyclone module.

16. A plume cleaner assembly comprising:
a plume cleaner;
a removable module including a plurality of apertures arranged with longitudinal axes; and
a fan positioned to draw plume air through the plurality of apertures for treatment by the plume cleaner and expel the treated plume air out of the plume cleaner assembly in a direction at an angle to the longitudinal axes of the plurality of apertures.

17. An apparatus comprising:
a toilet seat;
a plume cleaner assembly adjacent to the toilet seat cover and the toilet seat and independently removable with respect to the toilet seat cover and with respect to the toilet seat, the plume cleaner assembly comprising:
a plume cleaner;
a plurality of apertures arranged with longitudinal axes;
at least one radial channel configured to direct the plume air from a toilet bowl to the plurality of apertures; and
a fan positioned to draw plume air through the plurality of apertures and the at least one radial channel for treatment by the plume cleaner and expel the treated plume air out of the plume cleaner assembly in a direction at an angle to the longitudinal axes of the plurality of apertures.

* * * * *